United States Patent
Conner et al.

(10) Patent No.: US 7,528,160 B2
(45) Date of Patent: May 5, 2009

(54) FUSED HETEROCYCLIC DERIVATIVES AS PPAR MODULATORS

(75) Inventors: Scott Eugene Conner, Indianapolis, IN (US); James Allen Knobelsdorf, Fishers, IN (US); Nathan Bryan Mantlo, Brownsburg, IN (US); Daniel Ray Mayhugh, Carmel, IN (US); Xiaodong Wang, Carmel, IN (US); Guoxin Zhu, Indianapolis, IN (US); Jeffrey Michael Schkeryantz, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 240 days.

(21) Appl. No.: 10/541,502

(22) PCT Filed: Dec. 31, 2003

(86) PCT No.: PCT/US03/41690

§ 371 (c)(1),
(2), (4) Date: Dec. 23, 2005

(87) PCT Pub. No.: WO2004/063190

PCT Pub. Date: Jul. 29, 2004

(65) Prior Publication Data

US 2006/0217374 A1    Sep. 28, 2006

Related U.S. Application Data

(60) Provisional application No. 60/438,541, filed on Jan. 6, 2003.

(51) Int. Cl.
  *A61K 31/427*    (2006.01)
  *C07D 277/24*    (2006.01)

(52) U.S. Cl. .................................. 514/365; 548/203
(58) Field of Classification Search ................. 548/203, 548/374; 514/365, 374
  See application file for complete search history.

(56) References Cited

FOREIGN PATENT DOCUMENTS

| WO | WO 02/30895 A1 | 4/2002 |
|---|---|---|
| WO | WO 02/060434 A2 | 8/2002 |
| WO | WO 02/096904 A1 | 12/2002 |
| WO | WO 02/102780 A1 | 12/2002 |
| WO | WO 03/074051 A1 | 9/2003 |

OTHER PUBLICATIONS

Morissette et al. Advanced Drug Delivery Reviews 2004, 56, 275-300.*
Rami, H.K., et al., "Synthetic Ligands for PPARγ—Review of Patent Literature 1994-1999," *Expert Opinion on Therapeutic Patents*, Ashley Publications, GB, vol. 10, No. 5, 2000, pp. 623-634.

* cited by examiner

*Primary Examiner*—Rebecca L Anderson
*Assistant Examiner*—Jason Nolan
(74) *Attorney, Agent, or Firm*—Hamilton, Brook, Smith & Reynolds, P.C.

(57) ABSTRACT

The present invention is directed to a method of treatment by modulating a peroxisome proliferator activated receptor by employing a compound of Structural Formula (I). The variables in I are defined herein. Also included are compounds, methods of making compounds, and pharmaceutical compositions. The compounds of the present invention are believed to be effective in treating and preventing Syndrome X, Type H diabetes, hyperglycemia, hyperlipidemia, obesity, coagaulopathy, hypertension, atherosclerosis, and other disorders related to Syndrome X and cardiovascular diseases.

13 Claims, No Drawings

FUSED HETEROCYCLIC DERIVATIVES AS PPAR MODULATORS

RELATED APPLICATIONS

This application is the U.S. National Stage of International Application No. PCT/US2003/041690, filed 31 Dec. 2003, designating the U.S., published in English, and which claims the benefit of U.S. Provisional Application No. 60/438,541, filed Jan. 6, 2003, the entire teachings of which are incorporated herein by reference.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include, for example, PPARα, NUC1, PPARγ and PPARδ.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). A need exists for new pharmaceutical agents which affect treat or prevent cardiovascular disease, particularly that associated with Syndrome X, while preventing or minimizing weight gain, and more preferably while improving insulin sensitivity. It may be especially desirable when the active pharmaceutical agent selectively modulates a PPAR receptor subtype to provide an especially desirable pharmacological profile. In some instances, it can be desirable when the active pharmacological agent selectively modulates more than one PPAR receptor subtype to provide a desired pharmacological profile.

SUMMARY OF THE INVENTION

The present invention is directed to a method of treating a mammal in need of treatment for a disease, wherein the disease is treatable by modulating a peroxisome proliferator activated receptor, comprising the step of administering to the mammal in need thereof a therapeutically effective amount of a compound represented by Structural Formula I:

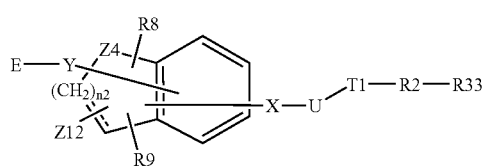

and stereoisomers, pharmaceutically acceptable salts, solvates and hydrates thereof, wherein:

(a) T1 is selected from the group consisting of

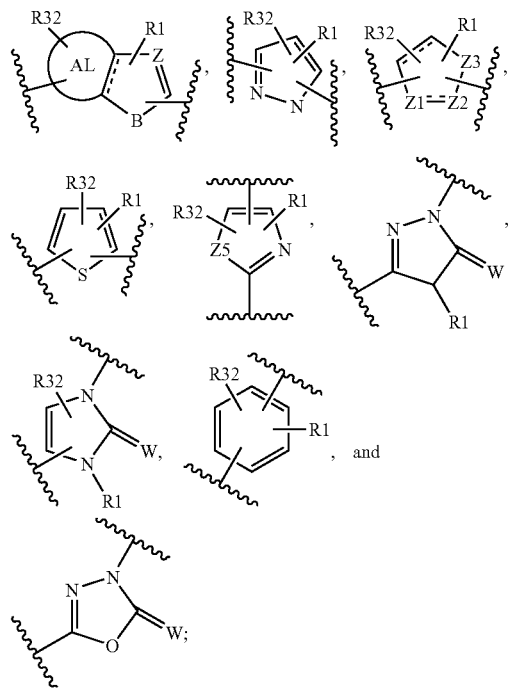

(b) R1 is selected from the group consisting of hydrogen, $C_1$-$C_8$ alkyl, $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, wherein $C_1$-$C_8$ alkyl, $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents independently selected from R1';

(c) R1', R26, R27, R28, R31, Z14', and Z15' are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, optionally substituted aryloxy, optionally substituted aryl-$C_{0-4}$-alkyl, optionally substituted heteroaryl, optionally substituted heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(d) R2 is selected from the group consisting of $C_0$-$C_8$ alkyl and $C_{1-6}$-heteroalkyl;

(e) X is selected from the group consisting of a bond, O, S, S(O)$_2$ and N;

(f) U is an aliphatic linker wherein one carbon atom of the aliphatic linker may be replaced with O, NH or S, and wherein such aliphatic linker is optionally substituted with R30;

(g) Y is selected from the group consisting of C, O, S, NH and a single bond;

(h) E is C(R3)(R4)A or A and wherein (i) A is selected from the group consisting of $C_0$-$C_6$ alkylcarboxyl, $C_0$-$C_6$ alkyltetrazole, $C_1$-$C_6$ alkylnitrile, $C_0$-$C_6$ alkylcarboxamide, $C_0$-$C_6$ alkylsulfonamide and $C_0$-$C_6$ alkylacylsulfonamide; wherein $C_0$-$C_6$ alkylsulfonamide, $C_0$-$C_6$ alkylacylsulfonamide and $C_0$-$C_6$ alkyltetrazole are each optionally substituted with from one to two groups independently selected from $R^7$;

(ii) each $R^7$ is independently selected from the group consisting of hydrogen, $C_1$-$C_6$ haloalkyl, aryl-$C_0$-$C_4$ alkyl and $C_1$-$C_6$ alkyl, wherein such alkyl and arylalkyl are each optionally substituted with from one to two groups independently selected from R7'; each R7' is independently selected from halo, $C_1$-$C_6$ alkyl, and halo$C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of hydrogen, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(i) B is selected from the group consisting of S and O, wherein when Z is C then B is N;

(j) Z is selected from the group consisting of N and C;

(k) Z1 and Z2 are each independently N or C with the proviso that at least one of Z1 and Z2 is N;

(l) Z3 is N or O;

(m) Z4 is selected from the group consisting of N, S, and O, wherein when Z4 is N and n2 is 1, T1 is not

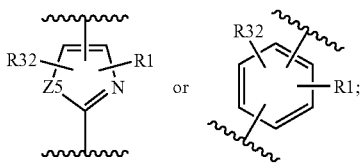

(n) Z5 is S or O;

(O) Z12 is selected from the group consisting of hydrogen and -Z13$C_0$-$C_3$alkylZ14;

(p) Z13 is selected from the group consisting of a single bond, CO, $CO_2$, CONZ15, and $SO_2$;

(q) Z14 is selected from the group consisting of aryl and heteroaryl, wherein the aryl and heteroaryl is each optionally substituted with from one to three substituents independently selected from Z14';

(r) Z15 is selected from the group consisting of hydrogen, aryl, and heteroaryl, wherein the aryl and heteroaryl is each optionally substituted with from one to three substituents independently selected from Z15';

(s) W is independently selected from the group consisting of S and O;

(t) n2 is 1 to 3;

(u) R8 is selected from the group consisting of hydrogen, $C_1$-$C_4$ alkyl, $C_1$-$C_4$ alkylenyl, oxo, sulfo, and halo;

(v) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, oxo, sulfo, and OR29, and R8 and R9 together optionally combine to form a fused $C_5$-$C_6$ ring with the carbons to which they are attached, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(w) R10, R11 are each independently selected from the group consisting of hydrogen, hydroxy, cyano, nitro, halo, oxo, $C_1$-$C_6$ alkyl, $C_0$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-6}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', $OS(O)_2$R16', $N(R17')_2$, NR18'C(O)R19', NR20'$SO_2$R21', SR22', S(O)R23', $S(O)_2$R24', and $S(O)_2N(R25')_2$; and wherein aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three independently selected from R28;

(x) R12', R12", R13', R14', R15', R16', R17', R18', R19', R20', R21', R22', R23', R24', and R25' are each independently selected from the group consisting of hydrogen, $C_1$-$C_6$ alkyl and aryl;

(y) R30 is selected from the group consisting of $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(z) R32 is selected from the group consisting of a bond, hydrogen, halo, $C_1$-$C_6$ alkyl, $C_1$-$C_6$ haloalkyl, and $C_1$-$C_6$ alkyloxo;

(aa) R33 is selected from the group consisting of C1-C8 alkyl, C1-C8 alkoxy, phenyl, thiophene, pyridine, piperidine,

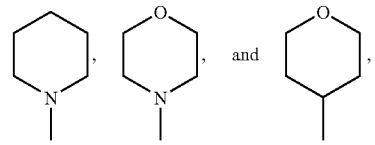

wherein the C1-C8 alkyl, C1-C8 alkoxy, phenyl, thiophene, pyridine, piperidine,

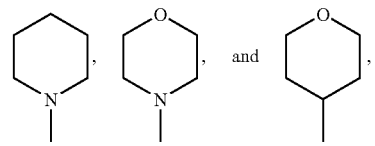

are each optionally substituted with R10 and R11;

(bb) AL is selected from the group consisting of a fused $C_3$-$C_8$ carbocyclic and a fused phenyl;

(cc) "- - - -" are each independently an optional bond to form a double bond at the indicated position; and (dd) wherein when Z4 is N, Z2 and Z3 are each N; and Preferably in Structural Formula (I), when n2 is 1, Z4 is O or S, and R33 is phenyl optionally substituted with R10 and R11, then T1 is selected from the group consisting of

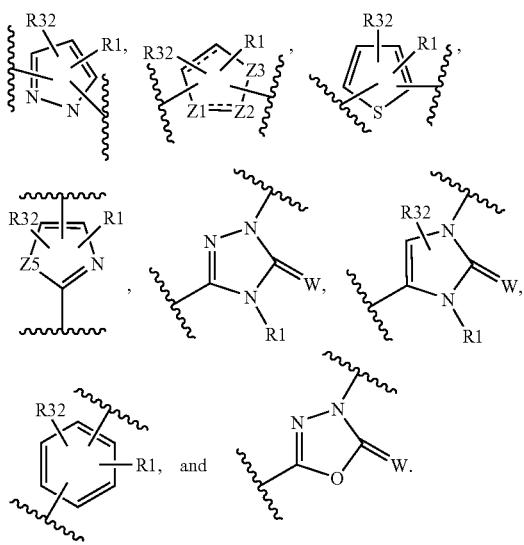

Another embodiment of the present invention is a compound represented by Structural Formula I', and stereoisomers, pharmaceutically acceptable salts, solvates and hydrates thereof:

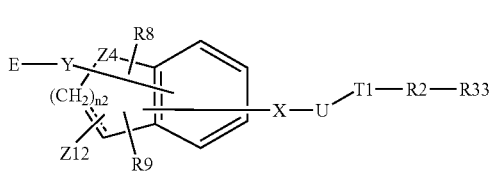

wherein the variables are as defined in Structural Formula I above, except as provided below:

R33 is selected from the group consisting of C2-C8 alkyl, C1-C8 alkoxy, phenyl, thiophene, pyridine, piperidine,

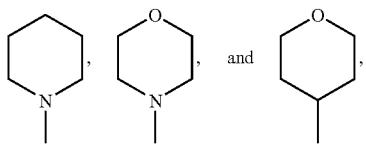

wherein the C2-C8 alkyl, C1-C8 alkoxy, phenyl, thiophene, pyridine, piperidine,

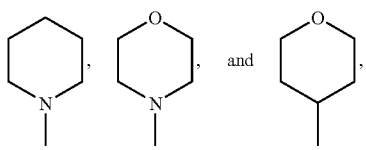

are each optionally substituted with R10 and R11.

In one embodiment, the present invention also relates to pharmaceutical compositions comprising at least one compound of the present invention, or a pharmaceutically acceptable salt, solvate, hydrate, or stereioisomer thereof, and a pharmaceutically acceptable carrier.

In another embodiment, the present invention relates to a method of selectively modulating a PPAR delta receptor by contacting the receptor with at least one compound represented by Structural Formula I or I', or a pharmaceutically acceptable salt, solvate, hydrate, or stereioisomer thereof.

In another embodiment, the present invention relates to a method of modulating one or more of the PPAR alpha, beta, gamma, and/or delta receptors.

In a further embodiment, the present invention relates to a method of making a compound represented by Structural Formula I or I'.

The compounds of the present invention are believed to be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. Further, compounds of this invention can be useful for lowering fibrinogen, increasing HDL levels, treating renal disease, controlling desirable weight, treating demyelinating diseases, treating certain viral infections, and treating liver disease. In addition, the compounds can be associated with fewer clinical side effects than compounds currently used to treat such conditions.

DETAILED DESCRIPTION OF THE INVENTION

The terms used to describe the instant invention have the following meanings.

As used herein, the term "aliphatic linker" or "aliphatic group" is a non-aromatic, consisting solely of carbon and hydrogen and may optionally contain one or more units of saturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a means hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$).

The term "alkoxy" and "alkyloxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "oxo" means a group of the formula: "=O". The term "sulfo" means a group of the formula "=S".

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). "Aryl" as defined above may be optionally substituted with a designated number of substituents as set forth in the embodiment recited above.

As used herein, the term "fused carbocyclic" means an optionally saturated $C_3$-$C_9$ ring system that is fused with the

group to form a 7 to 12 member bicyclic ring system. The fused ring system can optionally contain one or more double bonds. Such fused ring system is substituted with R1 and R32, as defined herein.

As used herein, the term "fused phenyl" means that the phenyl ring is fused with the

group to form a bicyclic group of the formula

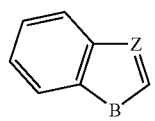

and wherein such group is substituted with R32 and R1, as defined herein.

The term "arylalkyl" refers to an aryl alkyl group which is linked to the parent molecule through the alkyl group, which may be further optionally substituted with a designated number of substituents as set forth in the embodiment recited above. When arylalkyl is aryl$C_0$alkyl, then the aryl group is bonded directly to the parent molecule. Likewise, arylheteroalkyl means an aryl group linked to the parent molecule through the heteroalkyl group.

The term "acyl" refers to alkylcarbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated number of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

As used herein, sulfonamide means the group —$NHSO_2$—, e.g., when A is sulfonamide, E-A is C(R3)(R4)—$NHSO_2$—. As used herein, acylsulfonamide means —C(O)$NHSO_2$—, e.g., when A is acylsulfonamide, E-A is C(R3)(R4)—C(O)$NHSO_2$—.

In Structural Formulas depicted herein, when more substitutents are indicated on a group than are chemically possible, e.g., when T1 is

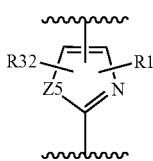

and Z5 is S or O, one skilled in the art will appreciate that excess substituents are intended in the alternative, e.g., that T1 above can be substituted with a substituent selected from R1 and R32.

A bond to the center of a cyclic group indicates that the bond is to any substitutable atom in the ring. For example, when T1 is the five membered ring shown above, R32 and R1 are bonded to any substitutable atom in the ring. When a bond passes through a ring and ends in the center of a second ring, the bond is to any substitutable ring atom in either ring. For example, in Structural Formula I, E-Y— is bonded to any substitutable ring atom in either the five or six membered ring. In Structural Formula II, shown below, E-Y— is bonded to any substitutable ring atom in the five membered ring only.

As used herein, the phrase "selectively modulate" means a compound whose EC50 for the stated PPAR receptor is at least ten fold lower than its EC50 for the other PPAR receptor subtypes.

When a compound of the invention I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. Diastereoisomer of the compounds disclosed herein and mixtures thereof are also encompassed in the present invention.

The compounds of the present invention may contain one or more chiral centers, and exist in different optically active forms. When compounds of the present invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the disclosed compounds may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of disclosed compounds and mixtures thereof.

Certain compounds of the disclosed compounds may exist in zwitterionic form and the present invention includes each zwitterionic form of the disclosed compounds and mixtures thereof.

"Pharmaceutically-acceptable salt" refers to salts of the disclosed compounds which are considered to be acceptable for clinical and/or veterinary use. Typical pharmaceutically-acceptable salts include those salts prepared by reaction of the compounds of the present invention with a mineral or organic acid or an organic or inorganic base. Such salts are known as acid additional salts and base addition salts, respectively. It will be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to the skilled artisan.

The term, "active ingredient" means the disclosed compounds as well as the sterioisomers, salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well known and readily available ingredients.

"Preventing" refers to reducing the likelihood that the recipient will incur or develop any of the pathological conditions described herein. The term "preventing" is particularly applicable to a patient that is susceptible to the particular pathological condition.

"Treating" refers to mediating a disease or condition and preventing, or mitigating, its further progression or ameliorate the symptoms associated with the disease or condition.

"Pharmaceutically-effective amount" means that amount of active ingredient, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition. Generally, the effective amount of a compound of the present invention will be between 0.02 through 5000 mg per day. Preferably the effective amount is between 1 through 1,500 mg per day. Preferably the dosage is from 1 through 1,000 mg per day.

The desired dose may be presented in a single dose or as divided doses administered at appropriate intervals.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective amount of active ingredient, as defined herein, to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of the present invention can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of the present invention, a stereoisomer, salt, solvate and/or hydrate thereof ("Active Ingredient") and one or more additional active agents, as well as administration of a compound of Active Ingredient and each active agent in its own separate pharmaceutical dosage formulation. For example, an Active Ingredient and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein an Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agent.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredients of the present invention, have valuable pharmacological properties and can be used in pharmaceutical compositions containing a therapeutically effective amount of Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient of the present invention, calculated to produce the desired therapeutic effect, in association with one or more pharmaceutically-acceptable excipients. The quantity of active ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing a compound of the present invention or the salts thereof may be provided in dosage unit form, preferably each dosage unit containing from about 1 to about 500 mg be administered although it will, of course, readily be understood that the amount of the compound or compounds of the present invention actually to be administered will be determined by a physician, in the light of all the relevant circumstances.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping, lyophilizing processes, and/or coupled with soluble polymers as targeted drug carriers.

The following pharmaceutical formulations 1 and 2 are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form are preferred and may be independently combined to produce a variety of preferred compounds and process conditions. The following list of embodiments of this invention is not intended to limit the scope of this invention in any way.

In further respective embodiments, the variables in Structural Formulas I and I' are as defined above, except that A is selected from the group consisting of $C_0$-$C_6$ alkylcarboxyl, $C_0$-$C_6$ alkyltetrazole, $C_1$-$C_6$ alkylnitrile, $C_0$-$C_6$ alkylsulfonamide and $C_0$-$C_6$ alkylacylsulfonamide; wherein $C_0$-$C_6$ alkylsulfonamide, $C_0$-$C_6$ alkylacylsulfonamide and $C_0$-$C_6$ alkyltetrazole are each optionally substituted with from one to two groups independently selected from $R^7$.

In another embodiment, the compounds represented by Structural Formulas I and I' are further represented by Structural Formula II:

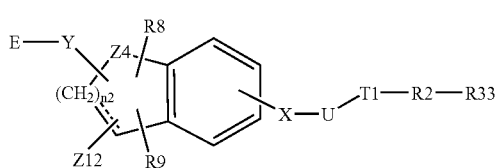

II

The variables are as defined for Structural Formulas I and I', except as provided below:

T1 is selected from the group consisting of

R1', R26, R27, R28, R31, Z14', and Z15' are each independently selected from the group consisting of hydrogen, hydroxy, cyano, nitro, halo, oxo, $C_1$-$C_6$ alkyl, $C_1$-$C_6$ alkylCOOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

R33 is selected from the group consisting of phenyl, thiophene, pyridine, piperidine,

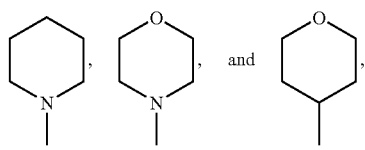

wherein the phenyl, thiophene, pyridine, piperidine,

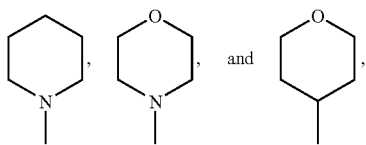

are each optionally substituted with R10 and R11; and Z2 and Z3 are each N.

Preferably, in Structural Formulas I, I', or II, T1 is selected from

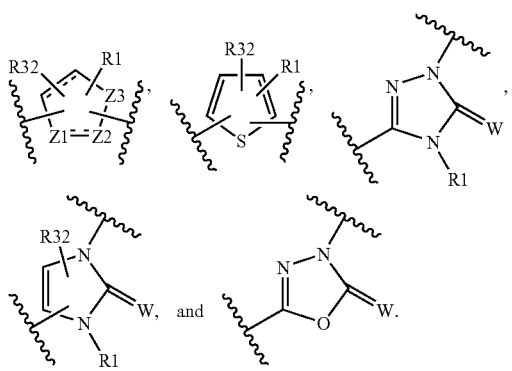

In another embodiment, the compounds represented by Structural Formulas I, I', or II are further represented by Structural Formulas III or IV:

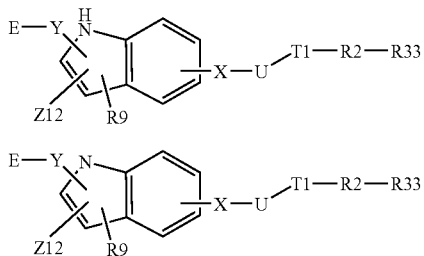

The variables are as defined for Structural Formulas I, I', and II.

In another embodiment, the compounds represented by Structural Formulas I, I', or II-IV are further represented by Structural Formula V:

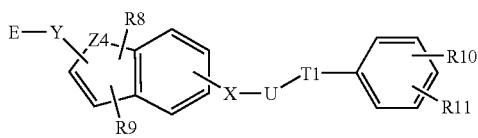

with the variables as provided above for Structural Formulas I, I', or II-IV.

More preferably, the compounds represented by Structural Formula V are further represented by one of Structural Formulas VI, VII, or VIII:

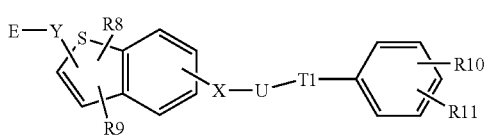

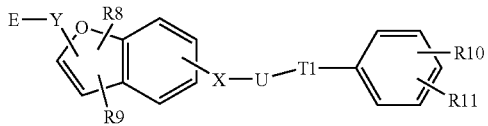

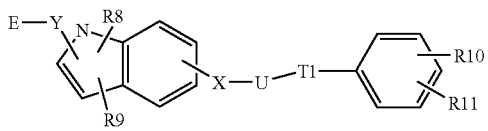

wherein the variables are as provided for Structural Formula V. In a separate embodiment of each of Structural Formulas VI, VII, and VIII, X is —O—; alternatively, X is —S—. Typically, X is as defined in the previous sentence and E is $C(R3)(R4)CO_2H$ or $CO_2H$. More typically, when X and E have these values, R1, R3, and R4 are each independently selected from the group consisting of hydrogen and $C_1$-$C_2$ alkyl. In a more preferred embodiment, X, E, R1, R3 and R4 are as defined in the previous sentence and R10 and R11 are each independently selected from the group consisting of hydrogen, halo, oxo, $C_1$-$C_6$ alkyl, $C_1$-$C_6$ alkyl-COOR12", $C_1$-$C_6$ alkoxy, $C_1$-$C_6$ haloalkyl, and $C_1$-$C_6$ haloalkyloxy, or more preferably, R10 is haloalkyl, preferably $CF_3$. In another preferred embodiment, X, E, R1, R3, R4, R10 and R11 are as described in the preceding sentence, and U is saturated $C_1$-$C_3$ alkyl that is optionally substituted with $C_1$-$C_3$ alkyl.

In a preferred embodiment, the compound represented by Structural Formula VI is further represented by Structural Formula IX, IX' or IX":

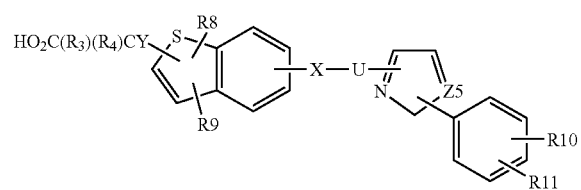

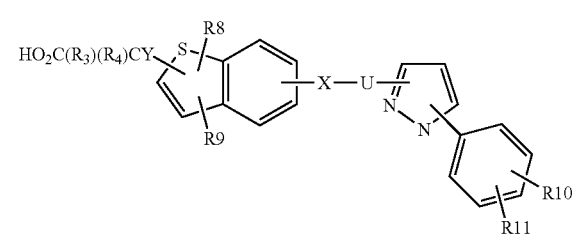

-continued

IX"

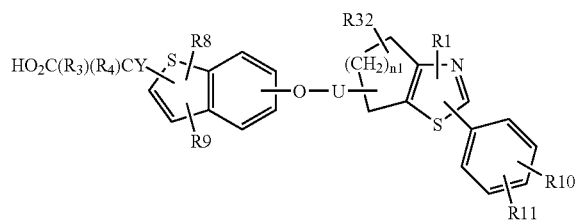

The variables in Structural Formulas IX, IX' and IX" are as defined in Structural Formula VI and n1 is an integer from 1-5. Preferably, the bicyclic ring system comprising $(CH_2)_{n1}$ is benzothiazole.

In another preferred embodiment, the compound represented by Structural Formula VII is further represented by Structural Formula X, XI or XI':

X

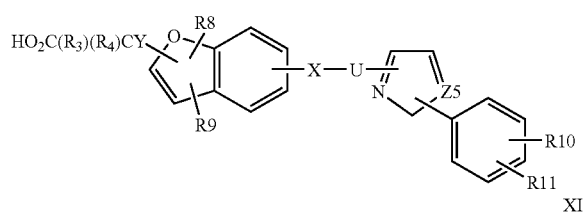

XI

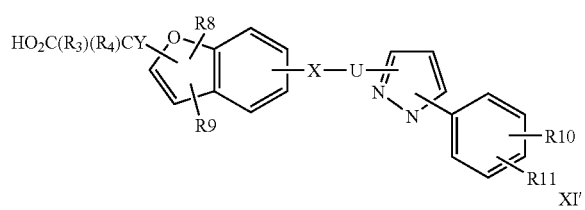

XI'

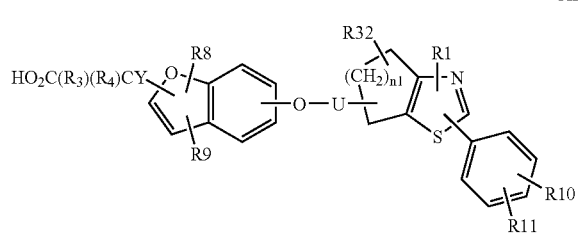

The variables in Structural Formulas IX, X, XI and XI' are as defined in Structural Formula VII and n1 is an integer from 1-5. Preferably, the bicyclic ring system comprising $(CH_2)_{n1}$ is benzothiazole.

In another preferred embodiment, the compound represented by Structural Formula VIII is further represented by Structural Formula XII (wherein n1 is an integer from 1 to 5), XIII, or XIV:

XII

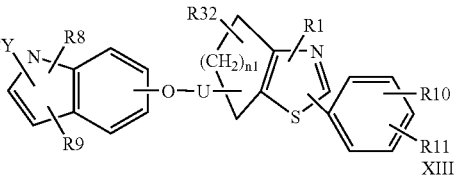

XIII

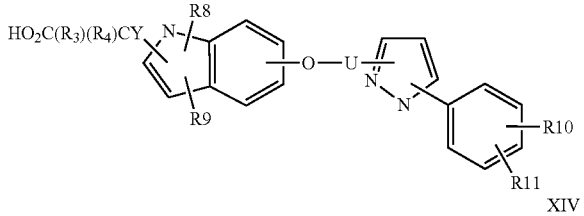

XIV

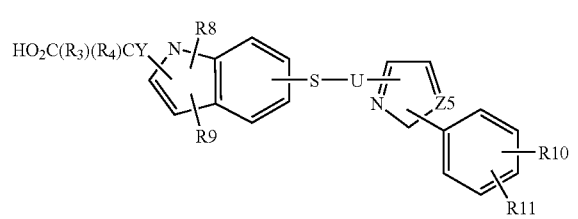

The variables in Structural Formulas XII, XIII and XIV are as defined in Structural Formula VIII and n1 is an integer from 1-5. Preferably, the bicyclic ring system comprising $(CH_2)_{n1}$ is benzothiazole.

In a preferred embodiment, the compound represented by Structural Formula VI or VII are more preferably represented by one of Structural Formulas XV-XXII:

XV

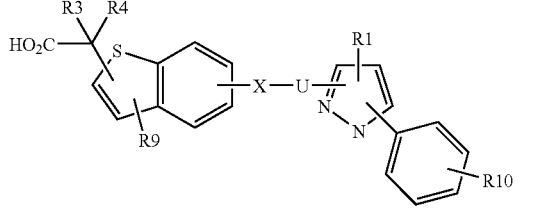

XVI (image showing structure with HO2C, R3, R4, S, R9, X-U, R1, N, S, R10)

XVII

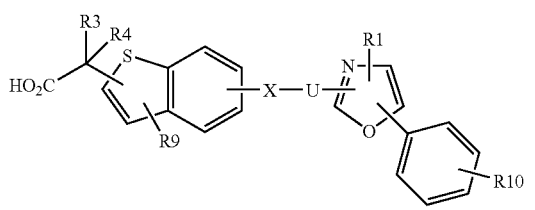

-continued

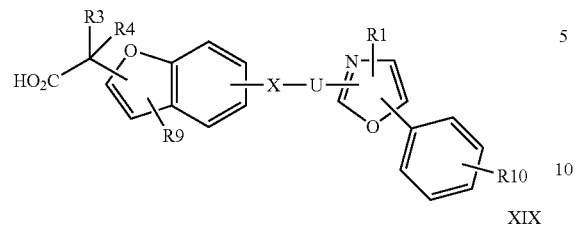

XVIII

XIX

XX

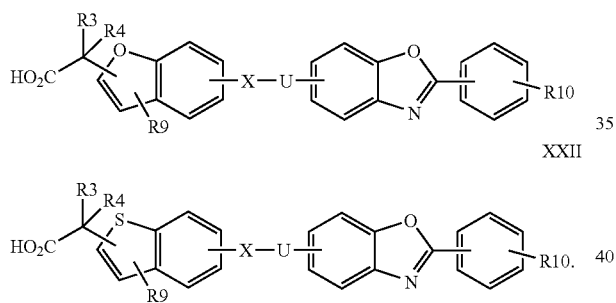

XXI

XXII

The variables in Structural Formulas XV-XXII are as defined in Structural Formula VI or VII.

In preferred embodiments of each of Structural Formulas XV-XXII, X is —O— or X is —S—. Typically, X is —O— or —S— and R3 and R4 are each independently selected from the group consisting of hydrogen and $C_1$-$C_2$ alkyl; preferably, R3 and R4 are hydrogen. In a more preferred embodiment, X and R3 and R4 are as described in the previous sentence and R10 is selected from the group consisting of hydrogen, halo, oxo, $C_1$-$C_6$ alkyl, $C_1$-$C_6$ alkyl-COOR12", $C_1$-$C_6$ alkoxy, $C_1$-$C_6$ haloalkyl, and $C_1$-$C_6$ haloalkyloxy, or more preferably, R10 is haloalkyl, preferably $CF_3$. Even more preferably, X, R3, R4 and R10 are as described in the previous sentence and U is saturated $C_1$-$C_3$ alkyl that is optionally substituted with $C_1$-$C_3$ alkyl. Even more preferably, X, R3, R4, R10 and U are as just described and R1 and R9 are independently selected from the group consisting of hydrogen, $C_1$-$C_8$ alkyl, $C_1$-$C_4$ alkenyl, and aryl-$C_{0-4}$-alkyl, or more preferably, hydrogen, $C_1$-$C_8$ alkyl.

More preferably, the variables are as defined in the preceding paragraph, and the compound is represented by VI or VII, or more preferably, by Structural Formulas XXIII-XXIX:

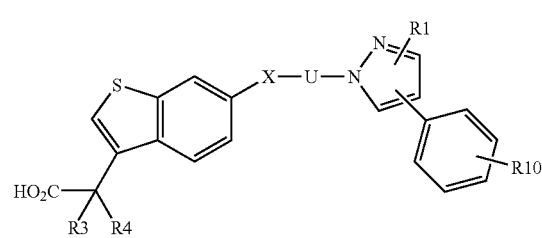

XXIII

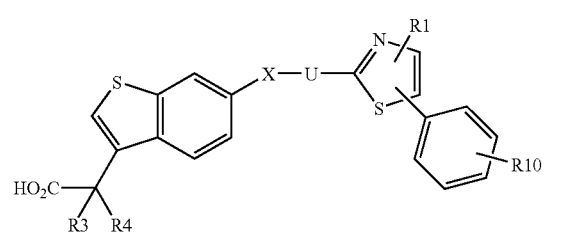

XXIV

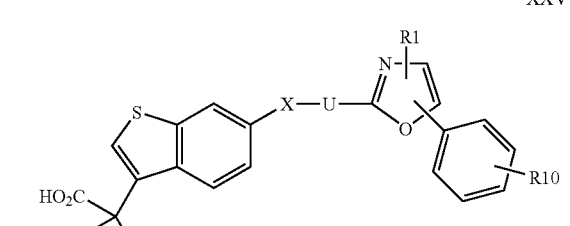

XXV

XXVI

XXVII

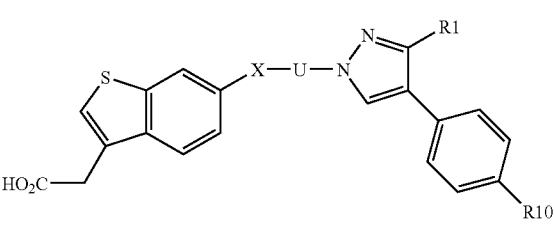

XXVIII

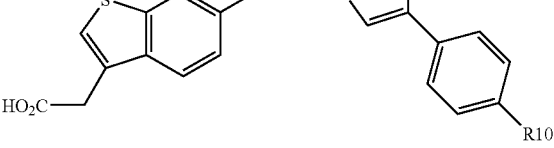

XXIX

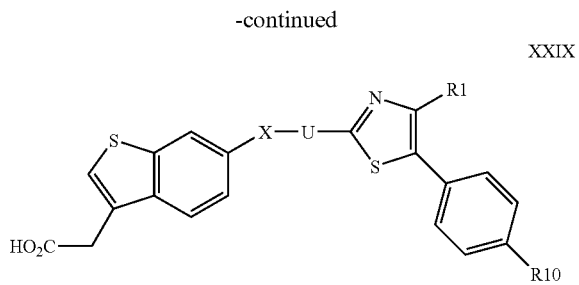

Preferred values for the variables shown in structural formulas depicted herein (including Structural Formulas I-XXIX and their corresponding "primed" formulas) are provided below:

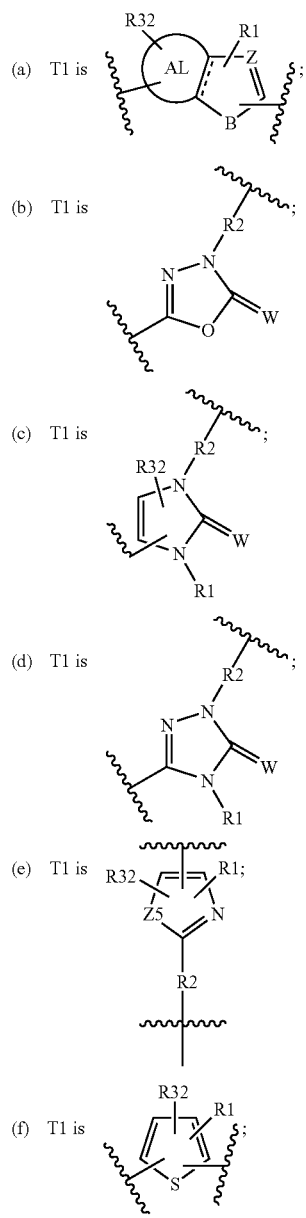

(g) T1 is 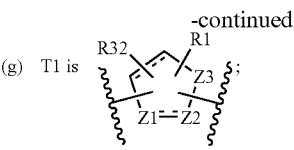;

(h) R3 is methyl;
(i) R4 is hydrogen;
(j) R3 and R4 are each hydrogen;
(k) R3 and R4 are each methyl;
(l) A is carboxyl;
(m) X is —O—;
(n) X is —S—;
(o) U is CH;
(p) U is $CH_2CH$;
(q) R9 is methyl;
(r) R9 is hydrogen;
(s) R9 is $C_1$-$C_3$ alkyl;
(t) R8 is methyl;
(u) R8 and R9 are each hydrogen;
(v) R8 and R9 are each oxo, Z4 is N, and Y is bonded to Z4;
(w) Y and X are substituted para to one another through the phenyl ring of the headpiece;
(x) R9 is selected from the group consisting of hydrogen, alkyl, alkenyl, halo, arylalkyl, heteroaryl, allyl and OR29;
(y) R9 is substituted arylalkyl or heteroaryl;
(z) R10 is $CF_3$;
(aa) R10 is haloalkyl;
(bb) R10 is haloalkyloxy;
(cc) R11 is hydrogen
(dd) R10 and R11 are each hydrogen;
(ee) R11 is haloalkyl;
(ff) Z is N;
(gg) Z is C and B is N;
(hh) Z4 is N;
(ii) Z4 is O;
(jj) Z4 is S;
(kk) B is S;
(ll) B is O;
(mm) AL is unsaturated;
(nn) AL is saturated;
(oo) AL is aromatic;
(pp) AL is a fused phenyl;
(qq) - - - - in the five membered ring each form a double bond at the designated position in Formula I;
(rr) R1 is $C_1$-$C_4$ alkyl;
(ss) R32 is hydrogen;
(tt) R2 is a bond;
(uu) R2 is $C_1$-$C_2$ alkyl;
(vv) Y is O;
(ww) Y is S;
(xx) Y is C;
(yy) E is C(R3)(R4)A;
(zz) R3 is hydrogen;
(aaa) R3 is $C_1$-$C_2$ alkyl;
(bbb) R4 is $C_1$-$C_2$ allyl;
(ccc) R3 and R4 are each hydrogen;
(ddd) R3 and R4 are each methyl;
(eee) A is COOH.

Additional embodiments of the present invention are compounds represented by the following Structural Formulas, whose variables are as described above for Structural Formula I or I':

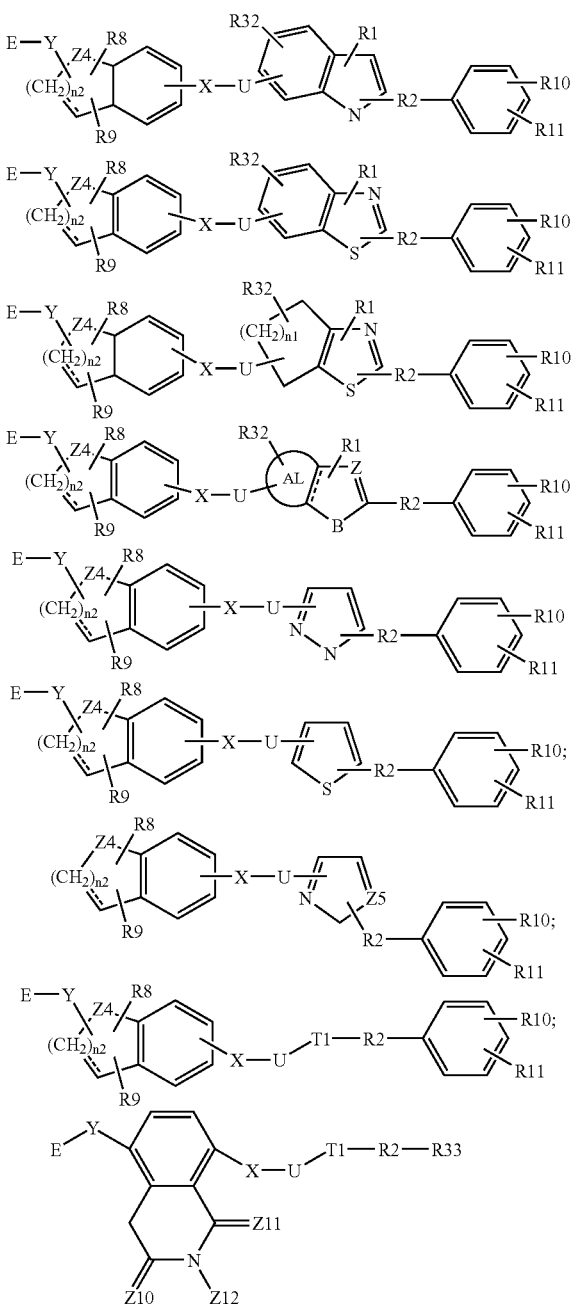

wherein Z10 and Z10 are each O or S and n1 is an integer from 1-15.

In preferred embodiments, the compound and the compound of the method are selected independently from:

{6-[4-Isopropyl-2-(4-trifluoromethyl-phenyl)-thiazol-5-yl-methoxy]-benzo[b]thiophen-3-yl}-acetic acid;

2-(6-((1-(4-(trifluoromethyl)phenyl)-3-methyl-1H-pyrazol-4-yl)methoxy)benzo[b]thiophen-3-yl)acetic acid;

2-(6-(2-(1-(4-(trifluoromethyl)phenyl)-3-methyl-1H-pyrazol-4-yl)propoxy)benzo[b]thiophen-3-yl)acetic acid;

2-(6-(2-(1-(4-(trifluoromethyl)phenyl)-3-methyl-1H-pyrazol-4-yl)propoxy)benzo[b]thiophen-3-yl)acetic acid;

2-(6-((R)-2-(1-(4-(trifluoromethyl)phenyl)-3-methyl-1H-pyrazol-4-yl)propylthio)benzo[b]thiophen-3-yl)acetic acid;

2-(6-((1-(4-(trifluoromethyl)phenyl)-3-isopropyl-1H-pyrazol-4-yl)methylthio)benzo[b]thiophen-3-yl)acetic acid; and 2-(6-((4-tert-butyl-2-(4-(trifluoromethyl) phenyl) thiazol-5-yl)methylthio)benzo[b]thiophen-3-yl)acetic acid.

In one embodiment, a compound represented by any of Structural Formulas I, I' or II-XXIX is in the S conformation; in another embodiment, the compound is in the R conformation; in yet another embodiment, the compound is radiolabeled.

In other embodiments, the compound represented by Structural Formula I, e.g., the compound of the method, is selected from:

{6-[5-Methyl-2-(4-trifluoromethyl-phenyl)-oxazol-4-yl-methoxy]-benzo[b]thiophen-3-yl}-acetic acid;

{4-[4-Isopropyl-2-(4-trifluoromethyl-phenyl)-thiazol-5-yl-methoxy]-benzo[b]thiophen-3-yl}-acetic acid;

{4-[5-Methyl-2-(4-trifluoromethyl-phenyl)-oxazol-4-yl-methoxy]-benzo[b]thiophen-3-yl}-acetic acid;

(6-{2-[5-Methyl-2-(4-trifluoromethyl-phenyl)-thiazol-4-yl]-propoxy}-benzo[b]thiophen-3-yl)-acetic acid;

(6-{1-[4-Isopropyl-2-(4-trifluoromethyl-phenyl)-thiazol-5-yl]-ethoxy}-benzo[b]thiophen-3-yl)-acetic acid;

(6-{2-[5-Methyl-2-(4-trifluoromethyl-phenyl)-oxazol-4-yl]-ethoxy}-benzo[b]thiophen-3-yl)-acetic acid;

(6-{2-[5-Methyl-2-(4-trifluoromethyl-phenyl)-oxazol-4-yl]-propoxy}-benzo[b]thiophen-3-yl)-acetic acid;

(6-{2-[4-Isopropyl-2-(4-trifluoromethyl-phenyl)-thiazol-5-yl]-propoxy}-benzo[b]thiophen-3-yl)-acetic acid;

(R)-(6-{2-[4-Isopropyl-2-(4-trifluoromethyl-phenyl)-thiazol-5-yl]-propoxy}-benzo[b]thiophen-3-yl)-acetic acid;

(S)-(6-{2-[4-Isopropyl-2-(4-trifluoromethyl-phenyl)-thiazol-5-yl]-propoxy}-benzo[b]thiophen-3-yl)-acetic acid;

(R)-(4-{2-[5-Methyl-2-(4-trifluoromethyl-phenyl)-thiazol-4-yl]-propoxy}-benzo[b]thiophen-3-yl)-acetic acid;

(S)-(4-{2-[5-Methyl-2-(4-trifluoromethyl-phenyl)-thiazol-4-yl]-propoxy}-benzo[b]thiophen-3-yl)-acetic acid;

(4-{2-[5-Methyl-2-(4-trifluoromethyl-phenyl)-thiazol-4-yl]-ethoxy}-benzo[b]thiophen-3-yl)-acetic acid;

Racemic-(4-{1-[4-Isopropyl-2-(4-trifluoromethyl-phenyl)-thiazol-5-yl]-ethoxy}-benzo[b]thiophen-3-yl)-acetic acid;

3-{1-[4-Methyl-2-(4-trifluoromethyl-phenyl)-oxazol-5-yl]-ethoxy}-pyrido[1,2-a]indole-10-carboxylic acid;

(6-{2-[5-Methyl-2-(4-trifluoromethyl-phenyl)-oxazol-4-yl]-propoxy}-benzofuran-3-yl)-acetic acid;

(6-{2-[4-Isopropyl-2-(4-trifluoromethyl-phenyl)-thiazol-5-yl]-propoxy}-benzofuran-3-yl)-acetic acid;

(6-{2-[4-Isopropyl-2-(4-trifluoromethyl-phenyl)-oxazol-5-yl]-propoxy}-benzofuran-3-yl)-acetic acid;

(6-{2-[4-Isopropyl-2-(4-trifluoromethyl-phenyl)-oxazol-5-yl]-ethoxy}-benzofuran-3-yl)-acetic acid;

{6-[4-Isopropyl-2-(4-trifluoromethyl-phenyl)-oxazol-5-yl-methoxy]-benzofuran-3-yl}-acetic acid;

(6-{1-Methyl-1-[4-methyl-2-(4-trifluoromethyl-phenyl)-oxazol-5-yl]-ethylsulfanyl}-benzofuran-3-yl)-acetic acid;

{6-[4-Isopropyl-2-(4-trifluoromethyl-phenyl)-oxazol-5-yl-methylsulfanyl]-benzofuran-3-yl}-acetic acid;

(6-{2-[4-Isopropyl-2-(4-trifluoromethyl-phenyl)-oxazol-5-yl]-ethylsulfanyl}-benzofuran-3-yl)-acetic acid;

(6-{1-[4-Methyl-2-(4-trifluoromethyl-phenyl)-oxazol-5-yl]-ethylsulfanyl}-benzofuran-3-yl)-acetic acid;

2-{6-[4-Isopropyl-2-(4-trifluoromethyl-phenyl)-oxazol-5-ylmethoxy]-benzofuran-3-yl}-propionic acid;

2-(6-{2-[4-Isopropyl-2-(4-trifluoromethyl-phenyl)-oxazol-5-yl]-ethoxy}-benzofuran-3-yl)-propionic acid;
(6-{2-[5-Methyl-2-(4-trifluoromethyl-phenyl)-thiazol-4-yl]-ethoxy}-benzofuran-3-yl)-acetic acid;
(R)-(6-{2-[5-Methyl-2-(4-trifluoromethyl-phenyl)-thiazol-4-yl]-propoxy}-benzofuran-3-yl)-acetic acid (Isomer 2);
(S)-(6-{2-[5-Methyl-2-(4-trifluoromethyl-phenyl)-thiazol-4-yl]-propoxy}-benzofuran-3-yl)-acetic acid;
(6-{1-[4-Methyl-2-(4-trifluoromethyl-phenyl)-thiazol-5-yl]-ethoxy}-2-oxo-3,4-dihydro-2H-quinolin-1-yl)-acetic acid;
{2-Oxo-6-[4-phenyl-2-(4-trifluoromethyl-phenyl)-thiazol-5-ylmethoxy]-3,4-dihydro-2H-quinolin-1-yl}-acetic acid;
{7-[4-Methyl-2-(4-trifluoromethyl-phenyl)-thiazol-5-yl-methoxy]-2-oxo-3,4-dihydro-2H-quinolin-1-yl}-acetic acid;
{8-[4-Methyl-2-(4-trifluoromethyl-phenyl)-thiazol-5-yl-methoxy]-2-oxo-2,3,4,5-tetrahydro-benzo[b]azepin-1-yl}-acetic acid;
(6-{1-[3-Methyl-1-(4-trifluoromethyl-phenyl)-1H-pyrazol-4-yl]-ethylsulfanyl}-benzofuran-3-yl)-acetic acid;
{6-[3-Methyl-1-(4-trifluoromethyl-phenyl)-1H-pyrazol-4-ylmethylsulfanyl]-benzofuran-3-yl}-acetic acid;
(6-{1-[3-Methyl-1-(4-trifluoromethyl-phenyl)-1H-pyrazol-4-yl]-ethoxy}-benzofuran-3-yl)-acetic acid;
2-{5-[1-(3,5-Bis-trifluoromethyl-phenyl)-5-methyl-1H-pyrazol-4-ylmethoxy]-indol-1-yl}-2-methyl-propionic acid;
(1-Methyl-6-{2-[3-methyl-1-(4-trifluoromethyl-phenyl)-1H-pyrazol-4-yl]-propoxy}-1H-indol-3-yl)-acetic acid;
{5-[2-(S-Methyl-3-phenyl-pyrazol-1-yl)-ethoxy]-indol-1-yl}-acetic acid;
(1-Methyl-6-{2-[3-methyl-1-(4-trifluoromethyl-phenyl)-1H-pyrazol-4-yl]-propoxy}-1H-indol-3-yl)-acetic acid;
(1-Methyl-6-{2-[4-methyl-2-(4-trifluoromethyl-phenyl)-thiazol-5-yl]-propoxy}-1H-indol-3-yl)-acetic acid;
{5-[5-(4-Trifluoromethyl-phenyl)-thiophen-2-ylmethoxy]-indol-1-yl}-acetic acid;
3-{4-[3-Isobutyl-5-(4-trifluoromethyl-phenyl)-thiophen-2-ylmethoxy]-2-methyl-phenyl}-propionic acid;
(5-{2-[3-Methyl-5-(4-trifluoromethyl-phenyl)-thiophen-2-yl]-propoxy}-indol-1-yl)-acetic acid;
(6-{1-[3-Methyl-1-(4-trifluoromethyl-phenyl)-1H-pyrazol-4-yl]-ethylsulfanyl}-benzofuran-3-yl)-acetic acid;
{6-[3-Methyl-1-(4-trifluoromethyl-phenyl)-1H-pyrazol-4-ylmethylsulfanyl]-benzofuran-3-yl}-acetic acid;
(6-{1-[3-Methyl-1-(4-trifluoromethyl-phenyl)-1H-pyrazol-4-yl]-ethoxy}-benzofuran-3-yl)-acetic acid;
2-{5-[1-(3,5-Bis-trifluoromethyl-phenyl)-5-methyl-1H-pyrazol-4-ylmethoxy]-indol-1-yl}-2-methyl-propionic acid;
(1-Methyl-6-{2-[3-methyl-1-(4-trifluoromethyl-phenyl)-1H-pyrazol-4-yl]-propoxy}-1H-indol-3-yl)-acetic acid;
{5-[2-(5-Methyl-3-phenyl-pyrazol-1-yl)-ethoxy]-indol-1-yl}-acetic acid;
(1-Methyl-6-{2-[3-methyl-1-(4-trifluoromethyl-phenyl)-1H-pyrazol-4-yl]-propoxy}-1H-indol-3-yl)-acetic acid;
Racemic-{5-[2-(4-Trifluoromethyl-phenyl)-5,6-dihydro-4H-cyclopentathiazol-4-ylmethoxy]-indol-1-yl}-acetic acid;
(S)-{6-[2-(4-Trifluoromethyl-phenyl)-5,6-dihydro-4H-cyclopentathiazol-4-ylmethoxy]-1H-indol-3-yl}-acetic acid;
{1-Methyl-6-[2-(4-trifluoromethyl-phenyl)-5,6-dihydro-4H-cyclopentathiazol-4-ylmethoxy]-1H-indol-3-yl}-acetic acid;
{5-[2-(4-Trifluoromethyl-phenyl)-4,5,6,7-tetrahydro-benzothiazol-4-ylmethoxy]-indol-1-yl}-acetic acid;
{6-[2-(4-Trifluoromethyl-phenyl)-4,5,6,7-tetrahydro-benzothiazol-4-ylmethoxy]-1H-indol-3-yl}-acetic acid;
{6-[2-(4-Trifluoromethyl-phenyl)-4,5,6,7-tetrahydro-benzothiazol-4-ylmethoxy]-1H-indol-3-yl}-acetic acid;
{1-Methyl-6-[2-(4-trifluoromethyl-phenyl)-4,5,6,7-tetrahydro-benzothiazol-4-ylmethoxy]-1H-indol-3-yl}-acetic acid;
{5-[2-(4-Trifluoromethyl-phenyl)-4,5,6,7-tetrahydro-benzothiazol-4-ylmethoxy]-indol-1-yl}-acetic acid;
{1-Methyl-6-[2-(4-trifluoromethyl-phenyl)-5,6,7,8-tetrahydro-4H-cycloheptathiazol-4-ylmethoxy]-1H-indol-3-yl}-acetic acid;
{6-[4-Isopropyl-2-(4-trifluoromethyl-phenyl)-thiazol-5-yl-methoxy]-benzo[b]thiophen-3-yl}-acetic acid;
2-(6-((1-(4-(trifluoromethyl)phenyl)-3-methyl-1H-pyrazol-4-yl)methoxy)benzo[b]thiophen-3-yl)acetic acid;
2-(6-(2-(1-(4-(trifluoromethyl)phenyl)-3-methyl-1H-pyrazol-4-yl)propoxy)benzo[b]thiophen-3-yl)acetic acid;
2-(6-(2-(1-(4-(trifluoromethyl)phenyl)-3-methyl-1H-pyrazol-4-yl)propoxy)benzo[b]thiophen-3-yl)acetic acid;
2-(6-((R)-2-(1-(4-(trifluoromethyl)phenyl)-3-methyl-1H-pyrazol-4-yl)propylthio)benzo[b]thiophen-3-yl)acetic acid;
2-(6-((1-(4-(trifluoromethyl)phenyl)-3-isopropyl-1H-pyrazol-4-yl)methylthio)benzo[b]thiophen-3-yl)acetic acid; and
2-(6-((4-tert-butyl-2-(4-(trifluoromethyl) phenyl) thiazol-5-yl)methylthio)-benzo[b]thiophen-3-yl) acetic acid.

In other embodiments, the compound represented by Structural Formula I' is selected from:
{6-[5-Methyl-2-(4-trifluoromethyl-phenyl)-oxazol-4-yl-methoxy]-benzo[b]thiophen-3-yl}-acetic acid;
{4-[4-Isopropyl-2-(4-trifluoromethyl-phenyl)-thiazol-5-yl-methoxy]-benzo[b]thiophen-3-yl}-acetic acid;
{4-[5-Methyl-2-(4-trifluoromethyl-phenyl)-oxazol-4-yl-methoxy]-benzo[b]thiophen-3-yl}-acetic acid;
(6-{2-[5-Methyl-2-(4-trifluoromethyl-phenyl)-thiazol-4-yl]-propoxy}-benzo[b]thiophen-3-yl)-acetic acid;
(6-{1-[4-Isopropyl-2-(4-trifluoromethyl-phenyl)-thiazol-5-yl]-ethoxy}-benzo[b]thiophen-3-yl)-acetic acid;
(6-{2-[5-Methyl-2-(4-trifluoromethyl-phenyl)-oxazol-4-yl]-ethoxy}-benzo[b]thiophen-3-yl)-acetic acid;
(6-{2-[5-Methyl-2-(4-trifluoromethyl-phenyl)-oxazol-4-yl]-propoxy}-benzo[b]thiophen-3-yl)-acetic acid;
(6-{2-[4-Isopropyl-2-(4-trifluoromethyl-phenyl)-thiazol-5-yl]-propoxy}-benzo[b]thiophen-3-yl)-acetic acid;
(R)-(6-{2-[4-Isopropyl-2-(4-trifluoromethyl-phenyl)-thiazol-5-yl]-propoxy}-benzo[b]thiophen-3-yl)-acetic acid;
(S)-(6-{2-[4-Isopropyl-2-(4-trifluoromethyl-phenyl)-thiazol-5-yl]-propoxy}-benzo[b]thiophen-3-yl)-acetic acid;
(R)-(4-{2-[5-Methyl-2-(4-trifluoromethyl-phenyl)-thiazol-4-yl]-propoxy}-benzo[b]thiophen-3-yl)-acetic acid;
(S)-(4-{2-[5-Methyl-2-(4-trifluoromethyl-phenyl)-thiazol-4-yl]-propoxy}-benzo[b]thiophen-3-yl)-acetic acid;
(4-{2-[5-Methyl-2-(4-trifluoromethyl-phenyl)-thiazol-4-yl]-ethoxy}-benzo[b]thiophen-3-yl)-acetic acid;
Racemic-(4-{1-[4-Isopropyl-2-(4-trifluoromethyl-phenyl)-thiazol-5-yl]-ethoxy}-benzo[b]thiophen-3-yl)-acetic acid;
3-{1-[4-Methyl-2-(4-trifluoromethyl-phenyl)-oxazol-5-yl]-ethoxy}-pyrido[1,2-a]indole-10-carboxylic acid;
(6-{2-[5-Methyl-2-(4-trifluoromethyl-phenyl)-oxazol-4-yl]-propoxy}-benzofuran-3-yl)-acetic acid;
(6-{2-[4-Isopropyl-2-(4-trifluoromethyl-phenyl)-thiazol-5-yl]-propoxy}-benzofuran-3-yl)-acetic acid;

(6-{2-[4-Isopropyl-2-(4-trifluoromethyl-phenyl)-oxazol-5-yl]-propoxy}-benzofuran-3-yl)-acetic acid;
(6-{2-[4-Isopropyl-2-(4-trifluoromethyl-phenyl)-oxazol-5-yl]-ethoxy}-benzofuran-3-yl)-acetic acid;
{6-[4-Isopropyl-2-(4-trifluoromethyl-phenyl)-oxazol-5-yl-methoxy]-benzofuran-3-yl}-acetic acid;
(6-{1-Methyl-1-[4-methyl-2-(4-trifluoromethyl-phenyl)-oxazol-5-yl]-ethylsulfanyl}-benzofuran-3-yl)-acetic acid;
{6-[4-Isopropyl-2-(4-trifluoromethyl-phenyl)-oxazol-5-yl-methylsulfanyl]-benzofuran-3-yl}-acetic acid;
(6-{2-[4-Isopropyl-2-(4-trifluoromethyl-phenyl)-oxazol-5-yl]-ethylsulfanyl}-benzofuran-3-yl)-acetic acid;
(6-{1-[4-Methyl-2-(4-trifluoromethyl-phenyl)-oxazol-5-yl]-ethylsulfanyl}-benzofuran-3-yl)-acetic acid;
2-{6-[4-Isopropyl-2-(4-trifluoromethyl-phenyl)-oxazol-5-ylmethoxy]-benzofuran-3-yl}-propionic acid;
2-(6-{2-[4-Isopropyl-2-(4-trifluoromethyl-phenyl)-oxazol-5-yl]-ethoxy}-benzofuran-3-yl)-propionic acid;
(6-{2-[5-Methyl-2-(4-trifluoromethyl-phenyl)-thiazol-4-yl]-ethoxy}-benzofuran-3-yl)-acetic acid;
(R)-(6-{2-[5-Methyl-2-(4-trifluoromethyl-phenyl)-thiazol-4-yl]-propoxy}-benzofuran-3-yl)-acetic acid (Isomer 2);
(S)-(6-{2-[5-Methyl-2-(4-trifluoromethyl-phenyl)-thiazol-4-yl]-propoxy}-benzofuran-3-yl)-acetic acid;
(6-{1-[4-Methyl-2-(4-trifluoromethyl-phenyl)-thiazol-5-yl]-ethoxy}-2-oxo-3,4-dihydro-2H-quinolin-1-yl)-acetic acid;
{2-Oxo-6-[4-phenyl-2-(4-trifluoromethyl-phenyl)-thiazol-5-ylmethoxy]-3,4-dihydro-2H-quinolin-1-yl}-acetic acid;
{7-[4-Methyl-2-(4-trifluoromethyl-phenyl)-thiazol-5-yl-methoxy]-2-oxo-3,4-dihydro-2H-quinolin-1-yl}-acetic acid;
{8-[4-Methyl-2-(4-trifluoromethyl-phenyl)-thiazol-5-yl-methoxy]-2-oxo-2,3,4,5-tetrahydro-benzo[b]azepin-1-yl}-acetic acid;
(6-{1-[3-Methyl-1-(4-trifluoromethyl-phenyl)-1H-pyrazol-4-yl]-ethylsulfanyl}-benzofuran-3-yl)-acetic acid;
{6-[3-Methyl-1-(4-trifluoromethyl-phenyl)-1H-pyrazol-4-ylmethylsulfanyl]-benzofuran-3-yl}-acetic acid;
(6-{1-[3-Methyl-1-(4-trifluoromethyl-phenyl)-1H-pyrazol-4-yl]-ethoxy}-benzofuran-3-yl)-acetic acid;
2-{5-[1-(3,5-Bis-trifluoromethyl-phenyl)-5-methyl-1H-pyrazol-4-ylmethoxy]-indol-1-yl}-2-methyl-propionic acid;
5   (1-Methyl-6-{2-[3-methyl-1-(4-trifluoromethyl-phenyl)-1H-pyrazol-4-yl]-propoxy}-1H-indol-3-yl)-acetic acid;
{5-[2-(5-Methyl-3-phenyl-pyrazol-1-yl)-ethoxy]-indol-1-yl}-acetic acid;
(1-Methyl-6-{2-[3-methyl-1-(4-trifluoromethyl-phenyl)-1H-pyrazol-4-yl]-propoxy}-1H-indol-3-yl)-acetic acid;
(1-Methyl-6-{2-[4-methyl-2-(4-trifluoromethyl-phenyl)-thiazol-5-yl]-propoxy}-1H-indol-3-yl)-acetic acid;
{5-[5-(4-Trifluoromethyl-phenyl)-thiophen-2-ylmethoxy]-indol-1-yl}-acetic acid;
3-{4-[3-Isobutyl-5-(4-trifluoromethyl-phenyl)-thiophen-2-ylmethoxy]-2-methyl-phenyl}-propionic acid;
(5-{2-[3-Methyl-5-(4-trifluoromethyl-phenyl)-thiophen-2-yl]-propoxy}-indol-1-yl)-acetic acid;
(6-{1-[3-Methyl-1-(4-trifluoromethyl-phenyl)-1H-pyrazol-4-yl]-ethylsulfanyl}-benzofuran-3-yl)-acetic acid;
{6-[3-Methyl-1-(4-trifluoromethyl-phenyl)-1H-pyrazol-4-ylmethylsulfanyl]-benzofuran-3-yl}-acetic acid;
(6-{1-[3-Methyl-1-(4-trifluoromethyl-phenyl)-1H-pyrazol-4-yl]-ethoxy}-benzofuran-3-yl)-acetic acid;
2-{5-[1-(3,5-Bis-trifluoromethyl-phenyl)-5-methyl-1H-pyrazol-4-ylmethoxy]-indol-1-yl}-2-methyl-propionic acid;
(1-Methyl-6-{2-[3-methyl-1-(4-trifluoromethyl-phenyl)-1H-pyrazol-4-yl]-propoxy}-1H-indol-3-yl)-acetic acid;
{5-[2-(5-Methyl-3-phenyl-pyrazol-1-yl)-ethoxy]-indol-1-yl}-acetic acid;
(1-Methyl-6-{2-[3-methyl-1-(4-trifluoromethyl-phenyl)-1H-pyrazol-4-yl]-propoxy}-1H-indol-3-yl)-acetic acid;
Racemic-{5-[2-(4-Trifluoromethyl-phenyl)-5,6-dihydro-4H-cyclopentathiazol-4-ylmethoxy]-indol-1-yl}-acetic acid;
(S)-{6-[2-(4-Trifluoromethyl-phenyl)-5,6-dihydro-4H-cyclopentathiazol-4-ylmethoxy]-1H-indol-3-yl}-acetic acid;
{1-Methyl-6-[2-(4-trifluoromethyl-phenyl)-5,6-dihydro-4H-cyclopentathiazol-4-ylmethoxy]-1H-indol-3-yl}-acetic acid;
{5-[2-(4-Trifluoromethyl-phenyl)-4,5,6,7-tetrahydro-benzothiazol-4-ylmethoxy]-indol-1-yl}-acetic acid;
{6-[2-(4-Trifluoromethyl-phenyl)-4,5,6,7-tetrahydro-benzothiazol-4-ylmethoxy]-1H-indol-3-yl}-acetic acid;
{6-[2-(4-Trifluoromethyl-phenyl)-4,5,6,7-tetrahydro-benzothiazol-4-ylmethoxy]-1H-indol-3-yl}-acetic acid;
{1-Methyl-6-[2-(4-trifluoromethyl-phenyl)-4,5,6,7-tetrahydro-benzothiazol-4-ylmethoxy]-1H-indol-3-yl}-acetic acid;
{5-[2-(4-Trifluoromethyl-phenyl)-4,5,6,7-tetrahydro-benzothiazol-4-ylmethoxy]-indol-1-yl}-acetic acid;
{1-Methyl-6-[2-(4-trifluoromethyl-phenyl)-5,6,7,8-tetrahydro-4H-cycloheptathiazol-4-ylmethoxy]-1H-indol-3-yl}-acetic acid;
{6-[4-Isopropyl-2-(4-trifluoromethyl-phenyl)-thiazol-5-ylmethoxy]-benzo[b]thiophen-3-yl}-acetic acid;
2-(6-((1-(4-(trifluoromethyl)phenyl)-3-methyl-1H-pyrazol-4-'yl)methoxy)benzo[b]thiophen-3-yl)acetic acid;
2-(6-(2-(1-(4-(trifluoromethyl)phenyl)-3-methyl-1H-pyrazol-4-yl)propoxy)benzo[b]thiophen-3-yl)acetic acid;
2-(6-(2-(1-(4-(trifluoromethyl)phenyl)-3-methyl-1H-pyrazol-4-yl)propoxy)benzo[b]thiophen-3-yl)acetic acid;
2-(6-((R)-2-(1-(4-(trifluoromethyl)phenyl)-3-methyl-1H-pyrazol-4-yl)propylthio)benzo[b]thiophen-3-yl)acetic acid;
2-(6-((1-(4-(trifluoromethyl)phenyl)-3-isopropyl-1H-pyrazol-4-yl)methylthio)benzo[b]thiophen-3-yl)acetic acid; and
2-(6-((4-tert-butyl-2-(4-(trifluoromethyl) phenyl) thiazol-5-yl)methylthio)benzo[b]thiophen-3-yl)acetic acid.

In embodiments of the method, employing any compound represented by Structural Formulas I-XXIX, the disease is selected from the group consisting of diabetes mellitus, Syndrome X, and atherosclerosis; in one preferred embodiment, the disease is diabetes mellitus; in another preferred embodiment, the disease is Syndrome X.

Synthesis

Compounds of the present invention have been formed as specifically described in the examples. Further, many compounds are prepared as more generally using a) alkylation of phenol/thiophenol with an alkylating agent, b) a Mitsunobu protocol (O. Mitsunobu, 1981 Synthesis, p1); c) and other methods known to the skilled artisan. Alternative synthesis methods may also be effective and known to the skilled artisan.

For example, an intermediate like A is alkylated with an alkylating agent B in the presence of a base (e.g. $K_2CO_3$, $Cs_2CO_3$ etc.). Hydrolysis in the presence of aqueous NaOH or LiOH gave the acid product.

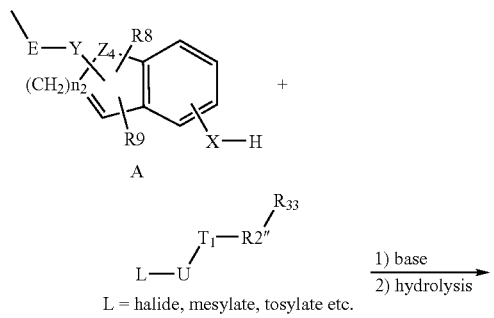

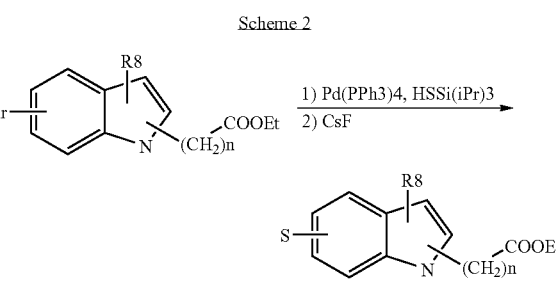

Mercaptyl-indol-1-yl carboxylic acid analogs:

Alternatively, an intermediate like A is coupled with an alcohol C under Mitsunobu reaction condition (DEAD/PPh3, ADDP/Pbu3 etc.). Hydrolysis in the presence of aqueous NaOH or LiOH gave the acid product:

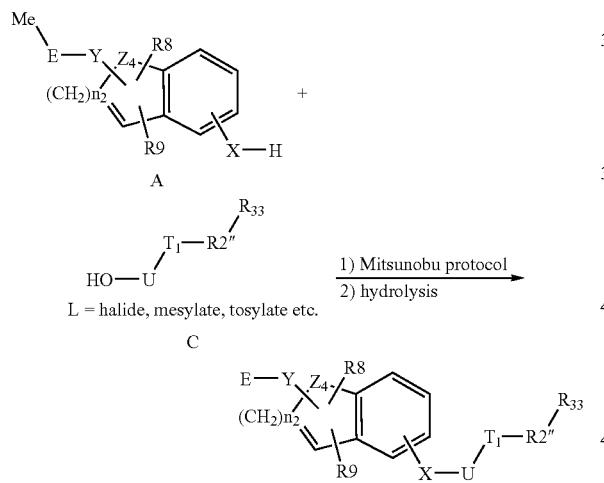

Hydroxy-indol-3-yl acetic acid analogs:

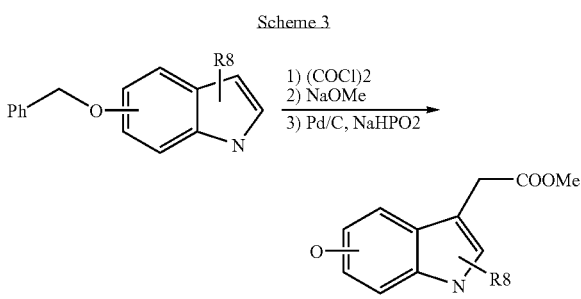

Intermediates A can be made by one of the following methods.

Hydroxy-indol-1-yl carboxylic acid analogs:

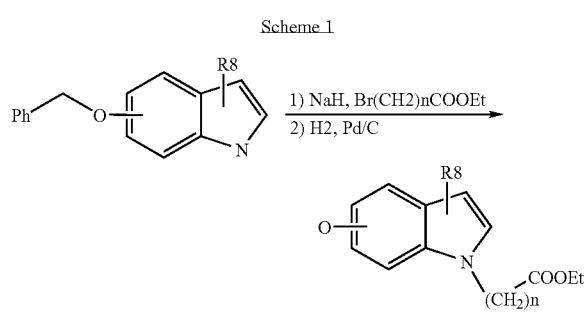

Hydroxy benzothiophen-3-yl acetic acid analogs:

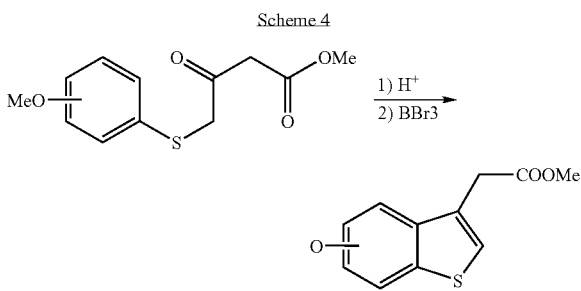

Hydroxy benzofuran-3-yl acetic acid analogs:

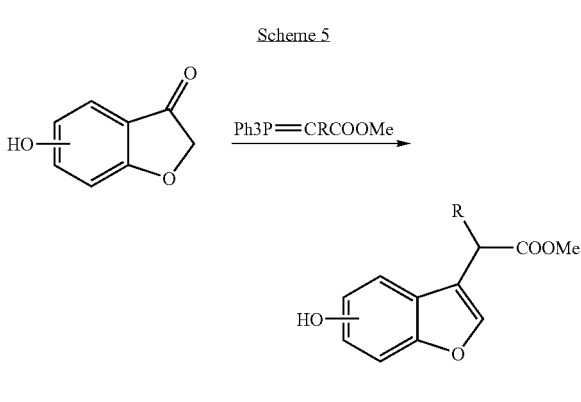

Thiophenol analogs:
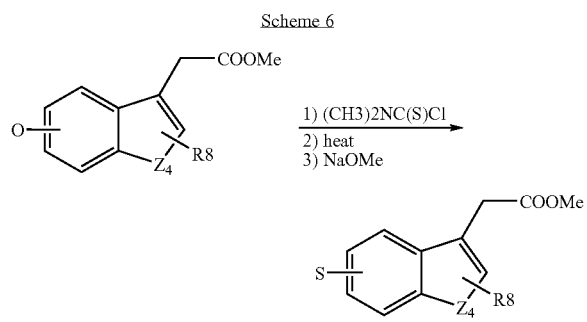
Intermediates B, and C can be made in one of the following methods.
5-Hydroxymethyl thiazole:
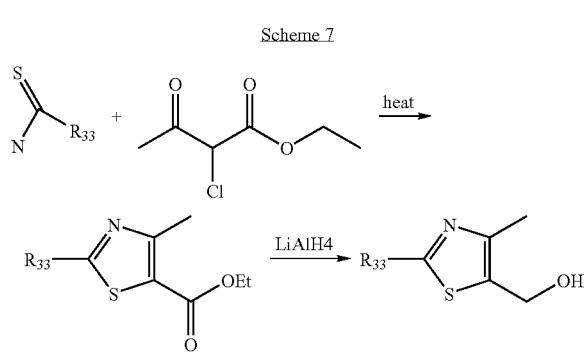
4-Hydroxyethyl thiazole:
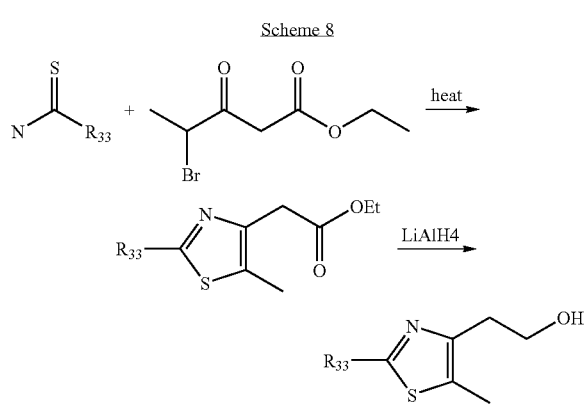
5-Hydroxyethyl oxazole:
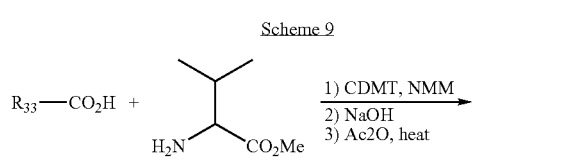
-continued
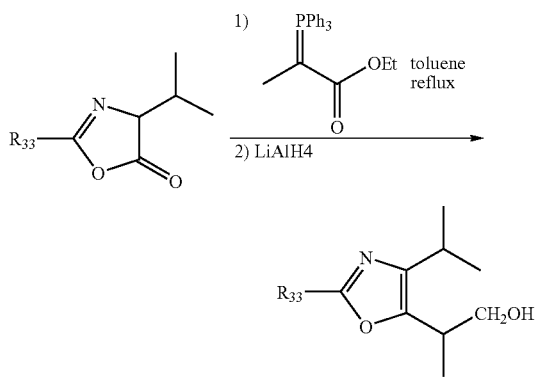
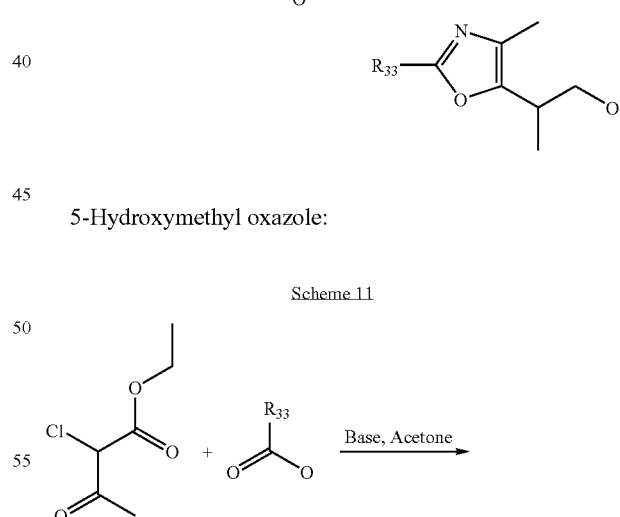
5-Hydroxymethyl oxazole:

-continued

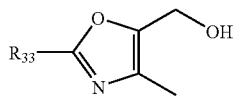

4-Hydroxylethyl oxazole:

Scheme 12

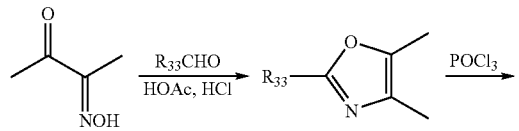

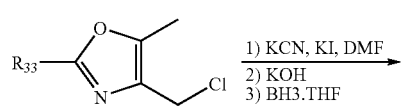

Scheme 13

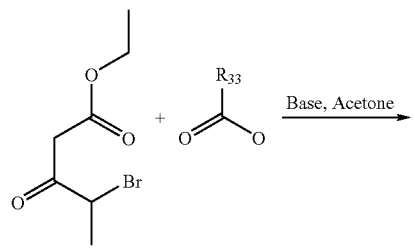

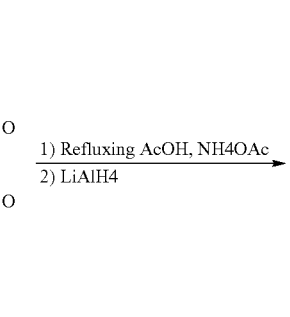

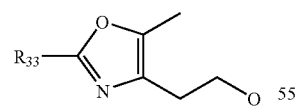

1-Aryl-4-hydroxymethyl Pyrazole:

Scheme 14

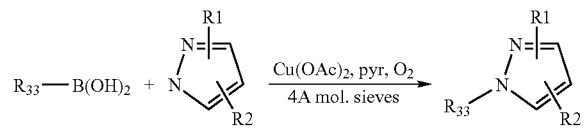

-continued

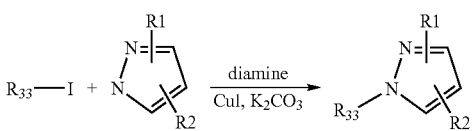

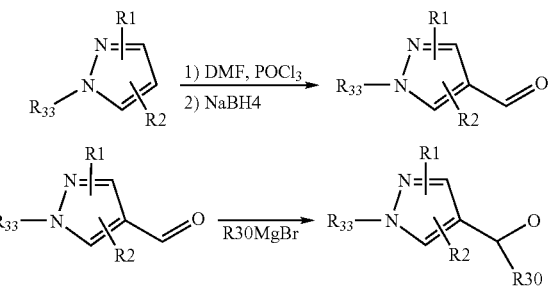

Alternatively, 1-aryl-3-formyl pyrazole can be made from β-ketoester as shown in scheme 15:

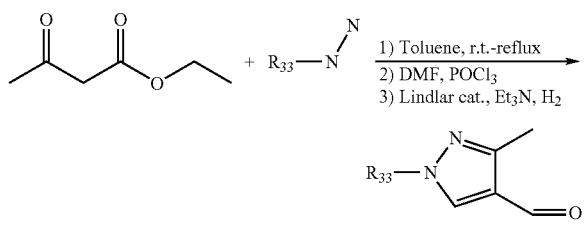

Further carbon chain extension can be achieved by a Wittig reaction as shown in Scheme 16, this chemistry can be applied to other series:

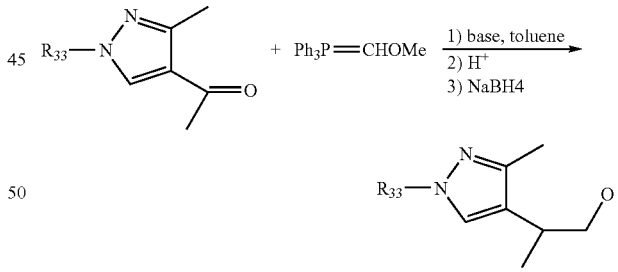

Imidazole analogs can be made according to scheme 17:

Scheme 17

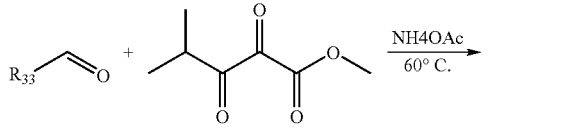

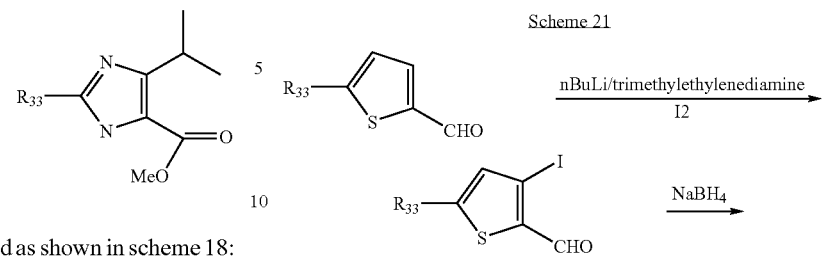
Isooxazole analog was synthesized as shown in scheme 18:
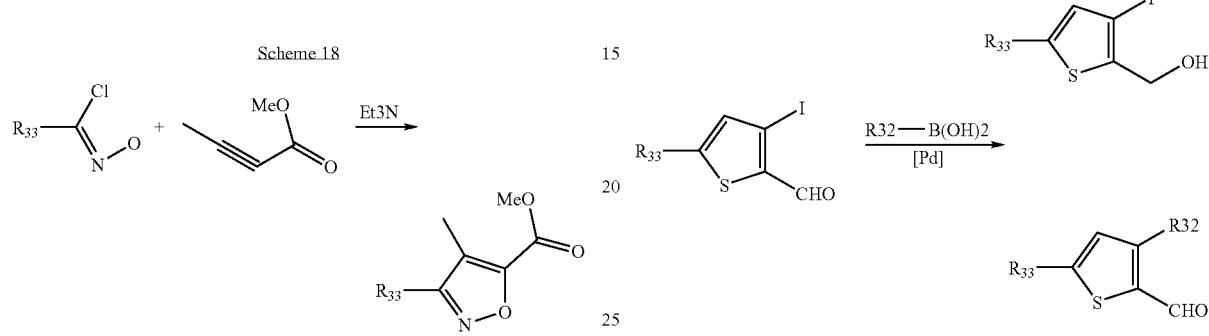
Triazole analogs were made from a cyclo-addition reaction:
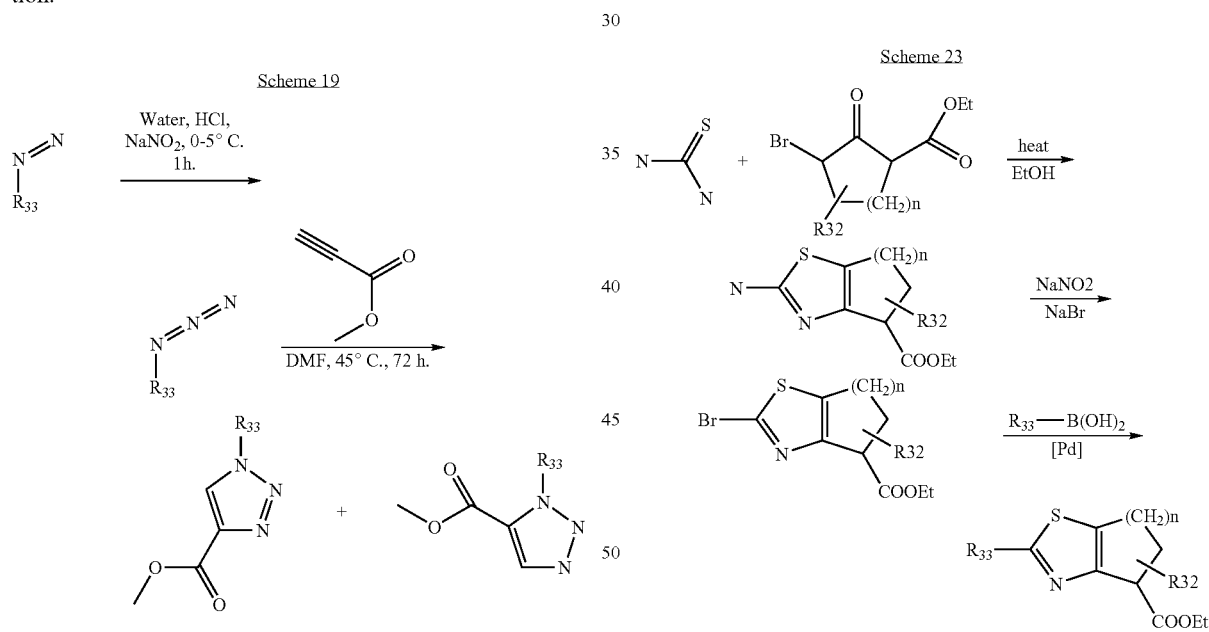
Thiophene compounds were made by following methods:
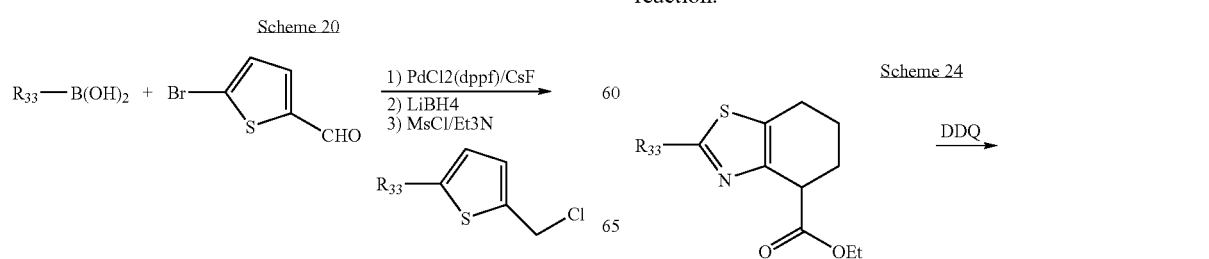
Fused thiazole compounds were made from a cyclization reaction between thioamide and α'-halo-β-ketoester:
Benzothiazole analogs were made from a DDQ oxidation reaction:

-continued

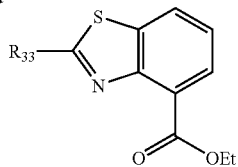

EXEMPLIFICATION

The Examples provided herein are illustrative of the invention claimed herein and are not intended to limit the scope of the claimed invention in any way.

Instrumental Analysis

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

Preparation 1

(5-Hydroxy-indol-1-yl)-acetic acid ethyl ester

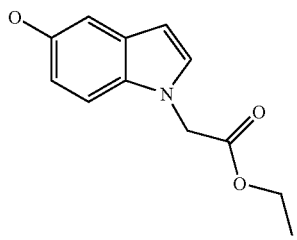

Step A 5-benzyloxyindole (10.0 g, 44.79 mmol) is dissolved into anhydrous DMF (100 mL) and cooled to 0° C. in an ice water bath. Sodium hydride (2.6 g, 67.18 mmol) is dissolved into anhydrous DMF (100 mL), then slowly added to the indole solution using an addition funnel. The reaction is allowed to stir at 0° C. for 1 h., then the ice bath is removed and the solution is allowed to warm slowly to room temperature. The solution is then cooled back down to 0° C. and ethyl bromoacetate (11.2 g, 67.18 mmol) is then added in one portion. The reaction is allowed to stir at 0° C. for 1 h., then the ice bath is removed and the solution is allowed to warm slowly to room temperature. Upon completion, the reaction is quenched carefully using water, then diluted with EtOAc (300 mL). Brine (100 mL) is added and the two layers are separated in a separatory funnel. The organic layer is rinsed with water (2×75 mL) and then dried over anhydrous magnesium sulfate. The organic layer is then concentrated and purified using flash column chromatography (5% EtOAc/Hexanes) to yield 11.86 g (86%) of (5-Benzyloxy-indol-1-yl)-acetic acid ethyl ester.

Step B (5-Benzyloxy-indol-1-yl)-acetic acid ethyl ester (3.49 g, 11.31 mmol) is dissolved in EtOH (50 mL) and glacial acetic acid is added (2.0 mL). Palladium on carbon (20% by wt., 0.700 g) is then added to the homogenous solution, and a hydrogen filled balloon is connected to the round bottom flask. A vacuum is created within the flask until the ethanol began to bubble, and the hydrogen allowed to enter the flask; this procedure is repeated three times, then the reaction is left to stir at room temperature overnight. Upon completion, the reaction is diluted with DCM (200 mL), and water (100 mL) is added. The mixture is filtered through a celite plug and the two phases are separated. The organic layer is washed with brine (2×75 mL), then dried over anhydrous magnesium sulfate, and concentrated to yield the title compound (2.42 g) in 98% yield. The residual acetic acid is removed by flash column chromatography.

$^1$H NMR (DMSO-d$_6$, 400 MHz): δ 1.18 (t, J=7.34 Hz, 3H), 4.12 (q, J=6.85 Hz, 2H), 4.99 (s, 2H), 5.73 (s, 1H), 6.23 (d, J=2.94 Hz, 1H), 6.60 (dd, J$_1$=1.96 Hz, J$_2$ 8.80 Hz, 1H), 6.84 (d, J=2.45 Hz, 1H), 7.12 (d, J=8.80 Hz, 1H), 7.19 (d, J=2.94 Hz, 2H); MS (ES, m/z):C$_{12}$H$_{13}$NO$_3$: 220.21(M$^+$+1), 218.7 (M$^+$−1).

The following compounds are prepared in a manner substantially similar to that used to prepare the compound of preparation 1.

Preparation 2

3-(5-Hydroxy-indol-1-yl)-propionic acid ethyl ester

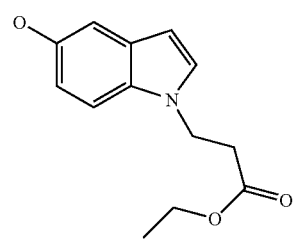

Preparation 3

4-(5-Hydroxy-indol-1-yl)-butyric acid ethyl ester

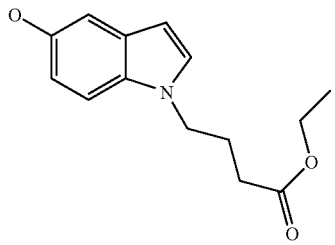

Preparation 4

5-(5-Hydroxy-indol-1-yl)-pentanoic acid ethyl ester

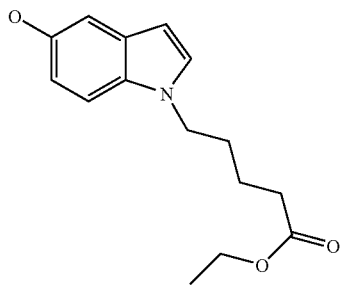

Preparation 5

2-(5-Hydroxy-indol-1-yl)-propionic acid ethyl ester

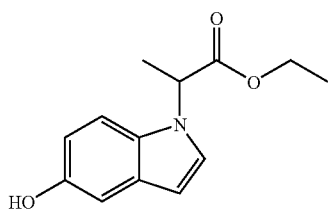

Step A 2-(5-Benzyloxy-indol-1-yl)-propionic acid ethyl ester

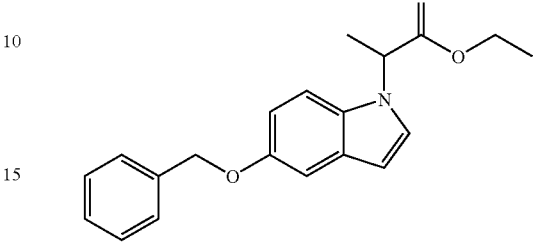

To a mixture of NaH (60%, 4.92 g, 0.205 mol) in DMF (60 mL) is added 5-benzoxyindole at 0~5° C., then stirred 30 min. ethyl 2-bromopropionate is added dropwise, the mixture is allowed to warm to room temperature and heated at 70° C. overnight, cooled to room temperature, diluted with ethyl acetate, washed with water and brine, dried over sodium sulfate. Concentration and column chromatography on silica gel eluted with hexanes and ethyl acetate yields the title compound (29 g).

Step B 2-(5-Hydroxy-indol-1-yl)-propionic acid ethyl ester

A mixture of 2-(5-Benzyloxy-indol-1-yl)-propionic acid ethyl ester (16 g) and Pd/C (5%, 1.93 g) in ethanol (190 mL) is stirred under 60 PSI of hydrogen overnight. Filtration and concentration yields the title compound.

Preparation 6

2-(5-Hydroxy-indol-1-yl)-2-methyl-propionic acid ethyl ester

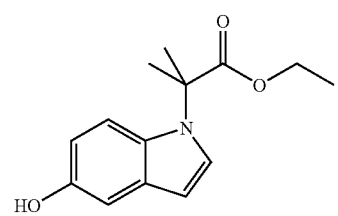

Step A 2-(5-Benzyloxy-indol-1-yl)-2-methyl-propionic acid ethyl ester

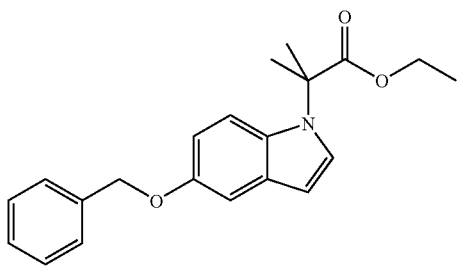

To a solution of 2-(5-benzyloxy-indol-1-yl)-propionic acid ethyl ester (20 g, 61.5 mmol) in THF (180 mL) is added LDA (2.0 M toluene, 37 mL) dropwise at −78° C. After the addition of LDA, the mixture is stirred for 30 min, then methyl iodide (8.77 g, 122.6 mmol) is added. The reaction mixture is allowed to warm to room temperature, after stirred for 2 hrs, quenched by water, extracted with ethyl acetate, dried over sodium sulfate. Concentration yields the title compound.

Step B 2-(5-Hydroxy-indol-1-yl)-2-methyl-propionic acid ethyl ester

A mixture of 2-(5-benzyloxy-indol-1-yl)-2-methyl-propionic acid ethyl ester (15.6 g) and Pd/C (5%, 1.93 g) in ethanol (190 mL) is stirred under 60 PSI of hydrogen overnight. Filtration and concentration yields the title compound (11 g).

Preparation 7

(5-Hydroxy-2-methyl-indol-1-yl)-acetic acid ethyl ester

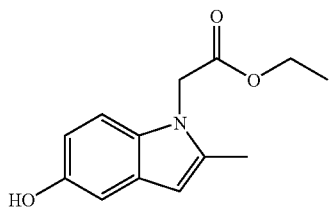

Step A (5-Methoxy-2-methyl-indol-1-yl)-acetic acid ethyl ester

To a solution of 2-methyl-5-methoxylindole (5.10 g, 31.6 mmol) in DMF (200 mL) is added sodium hydride (60%, 1.9 g, 47.4 mmol) at 0~5° C., stirred for 30 min, ethyl 2-bromoacetate (8.35 g, 50 mmol) is added. After 2 hr at room temperature, the reaction is quenched by water, extracted with ether. Combined organic layers are washed with water and brine, dried over sodium sulfate. Concentration yields the crude title product, which is used for next step without further purification.

Step B (5-hydroxy-2-methyl-indol-1-yl)-acetic acid ethyl ester

To a solution of (5-methoxy-2-methyl-indol-1-yl)-acetic acid ethyl ester (0.87 g, 3.51 mmol) in methylene chloride (25 mL) is added BBr3 (1.0 mL, 10.5 mmol) at −20° C. After stirred at −20° C. for 2 hrs, the reaction mixture is poured into ice, extracted with methylene chloride, dried over sodium sulfate. Concentration yields the crude title compound, which is used for next step without further purification.

Preparation 8

{5-[3-(Toluene-4-sulfonyloxy)-propoxy]-indol-1-yl}-acetic acid ethyl ester

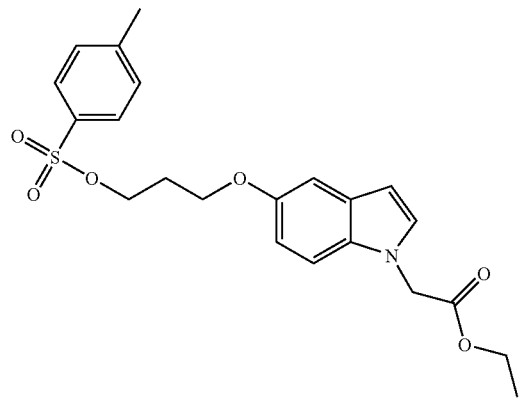

[5-(3-Hydroxy-propoxy)-indol-1-yl]-acetic acid ethyl ester (2.0 g, 6.55 mmol) is dissolved into anhydrous dichlormethane (DCM) (35 mL), then dimethylamino pyridine (300 mg, 1.965 mmol), tosic anhydride (4.3 g, 13.1 mmol), and pyridine (2.3 mL, 23 mmol) are added. The reaction allowed to stir at room temperature under nitrogen. Upon completion, the reaction is then diluted with DCM (100 mL) and saturated sodium bicarbonate solution (50 mL) is added and the two layers are separated in a separatory funnel. The organic layer is rinsed with water (2×75 mL) and brine (2×50 mL), then dried over anhydrous magnesium sulfate. The organic layer is then concentrated and purified using flash column chromatography (5% EtOAc/Hexanes) to yield 1.92 g (64%) of the title compound.

The following compounds are prepared in a similar manner:

Preparation 9

2-Methyl-2-{5-[3-(toluene-4-sulfonyloxy)-propoxy]-indol-1-yl}-propionic acid ethyl ester

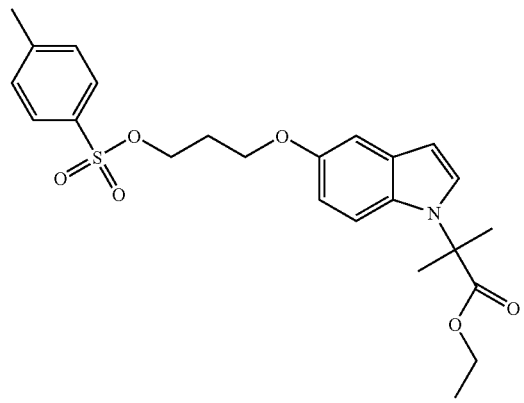

Preparation 10

{5-[2-(Toluene-4-sulfonyloxy)-ethoxy]-indol-1-yl}-acetic acid ethyl ester

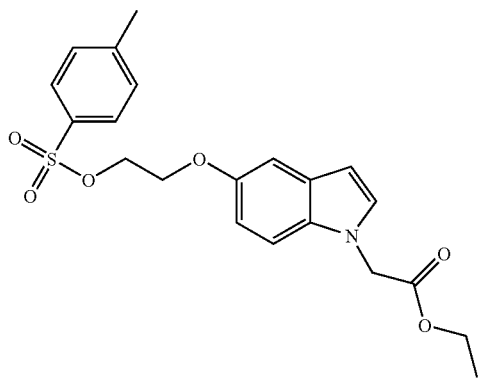

Preparation 11

(5-Mercapto-indol-1-yl)-acetic acid ethyl ester

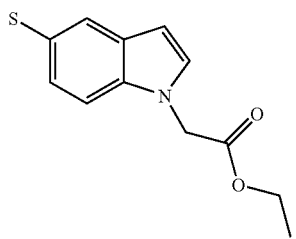

Step A (5-Bromo-indol-1-yl)-acetic acid ethyl ester (2.0 g, 7.09 mmol) is dissolved into anhydrous tetrahydrofuran (THF) (10 mL) and the reaction vessel purged with nitrogen a few times. Tetrakis triphenylphosphine palladium (175 mg, 0.15 mmol) is then added to the indole solution in one portion, purge again. Meanwhile, triisopropylsilylthiol (1.67 mL, 7.8 mmol) is dissolved in anhydrous THF (20 mL) and potassium hydride (0.483 mg, 7.8 mmol) is then slowly added. This mixture is heated to 50° C. for 4 h. After this solution has cooled to room temperature, it is transferred to the indole solution via cannula. This solution is the heated to 70° C. until the reaction is complete. Upon completion, the reaction is quenched carefully using water, then diluted with EtOAc (300 mL). Brine (100 mL) is added and the two layers are separated in a separatory funnel. The organic layer is rinsed with water (2×75 mL) and then dried over anhydrous magnesium sulfate. The organic layer is then concentrated and purified using flash column chromatography (5% EtOAc/Hexanes) to yield 1.3 g (50%) of (5-Triisopropylsilanylsulfanyl-indol-1-yl)-acetic acid ethyl ester.

Step B (5-Triisopropylsilanylsulfanyl-indol-1-yl)-acetic acid ethyl ester (60 mg, 0.1621 mmol) is dissolved in n-methylpyrrolidinone (NMP) (5 mL) and cesium fluoride (0.243 mmol) is added. The reaction is allowed to stir at room temperature until complete. This solution may be used in the coupling step (next) without further purification.

Preparation 12

(6-Hydroxy-1H-indol-3-yl)-acetic acid methyl ester

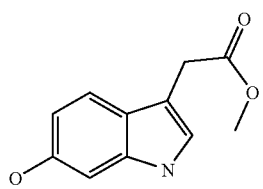

Step A (6-Benzyloxy-1H-indol-3-yl)-oxo-acetic acid methyl ester

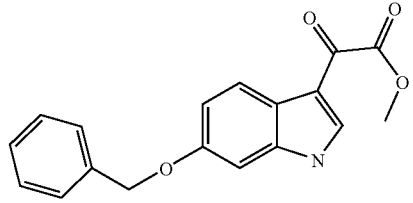

To a solution of 6-benzoxyindole (1.05 g, 4.7 mmol) in ether (8 mL) is added oxalyl chloride (0.45 mL) at 0~5° C., stirred for 2 hrs. The reaction mixture is cooled to −78° C., sodium methoxide (25% w/w in methanol, 2.4 mL) is added, warmed up to room temperature, quenched by water. Solid product is collected by filtration, washed by water and dried under vacuum.

Step B (6-Hydroxy-1H-indol-3-yl)-acetic acid methyl ester

A mixture of (6-benzyloxy-1H-indol-3-yl)-oxo-acetic acid methyl ester (1.45 g, 4.7 mmol) and Pd/C (10%, 0.9 g) in dioxane (38 mL) is degassed and filled with nitrogen for three times, then a solution of NaH2PO2 (6 g) in water (5 mL) is added dropwise at 100° C. The reaction mixture is heated overnight, filtered through celite and concentrated. The residue is taken into ethyl acetate, washed with water and brine, dried over sodium sulfate. Concentration and column chromatography on silica gel yields the title compound (600 mg).

The following compounds are made in a similar manner:

Preparation 13

(6-Hydroxy-1-methyl-1H-indol-3-yl)-acetic acid methyl ester

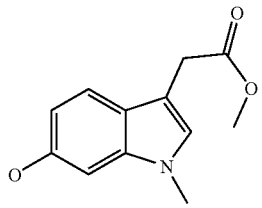

Preparation 14

(5-Hydroxy-1H-indol-3-yl)-acetic acid methyl ester

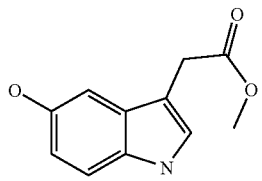

Preparation 15

(5-Hydroxy-1-methyl-1H-indol-3-yl)-acetic acid methyl ester

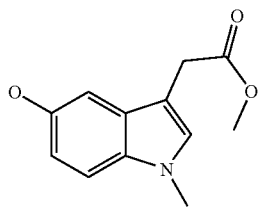

Preparation 16

(1-Ethyl-6-hydroxy-1H-indol-3-yl)-acetic acid ethyl ester

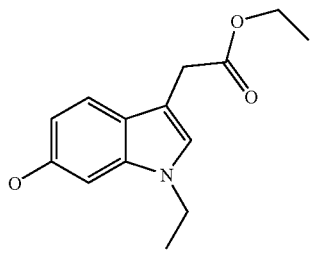

Step A

To a solution of (6-Benzyloxy-1H-indol-3-yl)-oxo-acetic acid ethyl ester (3.0 g, 9.7 mmol) in anhydrous dimethyl formamide (50 mL) at 0° C. under nitrogen is added sodium hydride (0.600 g, 14.5 mmol) in small portions. The reaction is allowed to warm to room temperature slowly and monitored by TLC. Upon complete conversion, the reaction is cooled back down to 0° C. and ethyl bromide (1.5 mL, 20 mmol) is slowly added to the slurry. The reaction is allowed to warm slowly to room temperature and monitored by TLC. After complete consumption of the starting material, the reaction is quenched with water, then diluted with ethyl acetate, and the two phases are separated. The organic layer is washed, dried, filtered and concentrated. The crude (6-Benzyloxy-1-ethyl-1H-indol-3-yl)-oxo-acetic acid ethyl ester (0.843 g, 2.40 mmol), 25% yield, is further purified using flash column chromatography.

Step B (6-Benzyloxy-1-ethyl-1H-indol-3-yl)-oxo-acetic acid ethyl ester (0.843 g, 2.40 mmol) is dissolved in anhydrous dioxane (10 mL) then purged and back filled with nitrogen a few times. Palladium on carbon (10%) (0.200 g, 20% by wt.) is added and the reaction followed by heating to reflux. Slow addition of a saturated solution of sodium hypophosphite is initiated and the reaction is monitored by TLC. After the starting material is completely consumed, the reaction is allowed to cool to room temperature, diluted with dichloromethane and celite added. The mixture is filtered through a plug of celite and the two phases are separated. The organic layer is washed with water and brine, dried over sodium sulfate, then concentrated. The residue is further purified using flash column chromatography. The (1-Ethyl-6-hydroxy-1H-indol-3-yl)-acetic acid ethyl ester (0.564 g, 2.28 mmol) is formed in 95% yield.

The following compound is made in a similar manner:

Preparation 17

(1-propyl-6-hydroxy-1H-indol-3-yl)-acetic acid ethyl ester

Preparation 18

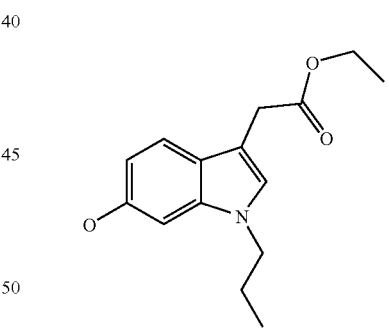

(6-Hydroxy-benzo[b]thiophen-3-yl)-acetic acid ethyl ester

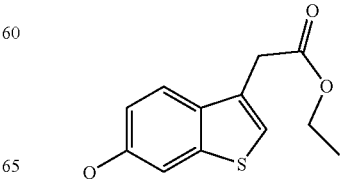

Step A

4-(3-Methoxy-phenylsulfanyl)-3-oxo-butyric acid ethyl ester

Ethyl 4-chloroacetoacetate (32.6 g, 0.188 mol), 3-methoxythiophenol (25.1 g, 0.179 mol) and DMF (700 mL) are combined and degassed by bubbling nitrogen through the stirred mixture for about 10 min, then potassium carbonate (50 g, 0.36 mol) is added to the stirred mixture in one batch. This mixture is stirred under nitrogen at room temperature for 2 h, the mixture is filtered to remove potassium carbonate, then diluted with ethyl acetate. The resulting solution is washed with water, then 5% aq. NaCl. The combined organics are washed with brine, dried over $Na_2SO_4$. Concentration yields the title compound as yellow liquid. This material is used without purification.

Step B

(6-Methoxy-benzo[b]thiophen-3-yl)-acetic acid ethyl ester 4-(3-Methoxy-phenylsulfanyl)-3-oxo-butyric acid ethyl ester (10.0 g) is added to pre-cooled methanesulfonic acid (60 mL) at 0~5° C., then the reaction mixture is allowed to warm to room temperature. After 1 h, the mixture is diluted with ice water and extracted with ethyl acetate. The combined organics are washed with brine, dried over $Na_2SO_4$, concentrated. Chromatography on silica gel elited with hexanes and ethyl acetate yields (6-methoxy-benzo[b]thiophen-3-yl)-acetic acid ethyl ester (4.8 g) and (4-methoxy-benzo[b]thiophen-3-yl)-acetic acid ethyl ester (0.8 g)

Step C

(6-hydroxy-benzo[b]thiophen-3-yl)-acetic acid ethyl ester

To a solution of (6-Methoxy-benzo[b]thiophen-3-yl)-acetic acid ethyl ester (2.4 g, 9.6 mmol) in methylene chloride (60 mL) is added BBr3 (1.0 M, heptane, 29.4 mL, 29.4 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (2.2 g).

Preparation 19

(4-Hydroxy-benzo[b]thiophen-3-yl)-acetic acid ethyl ester

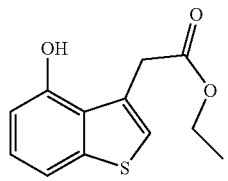

To a solution of (4-Methoxy-benzo[b]thiophen-3-yl)-acetic acid ethyl ester (0.7 g, 2.8 mmol) in methylene chloride (18 mL) is added BBr3 (1.0 M, heptane, 8.6 mL, 8.6 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (0.4 g).

Preparation 20

(6-Hydroxy-benzofuran-3-yl)-acetic acid methyl ester

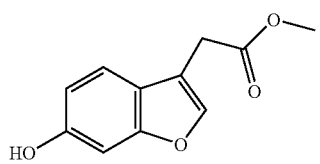

A mixture of 6-hydroxy-(2H)-benzofuran-3-one (5.0 g, 33.3 mmol), methyl (triphenylphosphoranylidene)acetate (25.0 g, 73 mmol), and xylenes (100 mL) is refluxed 6 hr. The reaction is concentrated and diluted with enough 1M aqueous hydrochloric acid to adjust pH to 2-3. The product is extracted into ethyl acetate (3×100 mL). The combined extracts are dried over anhydrous magnesium sulfate, filtered and concentrated. The residue is purified via silica chromatography eluting with 7:3 hexanes:ethyl acetate to afford the product as a orange oil, 1.3 g, 20%. MS M$^+$+1 207. The structure is confirmed by $^1$H NMR spectroscopy.

The following compound is made in a similar manner:

Preparation 21

2-(6-Hydroxy-benzofuran-3-yl)-propionic acid methyl ester

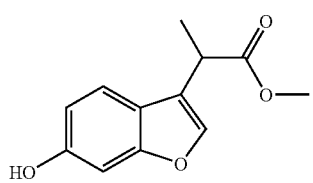

An orange oil. MS M$^+$+1 221. The structure is confirmed by $^1$H NMR spectroscopy.

Preparation 22

6-Hydroxy-naphthalene-2-carboxylic acid methyl ester

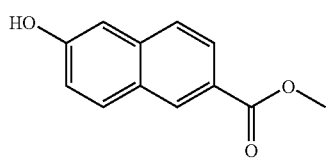

6-Methoxy-naphthalene-2-carboxylic acid methyl ester (0.68 g, 3.13 mmol) is stirred in dichloromethane (50 mL) in an ice/water bath. Aluminum trichloride (1.67 g, 12.5 mmol) is added followed by ethane thiol (1.2 mL, 15.7 mmol). The mixture is stirred at room temperature 2 hr. Water (25 mL) is added and the product is extracted into ethyl acetate (2×75 mL). The combined extracts are concentrated, and the residue is purified via silica gel chromatography eluting with 8:2 hexanes:ethyl acetate to afford the title compound as a white solid, 0.432 g, 69%. MS M⁺+1 203. The structure is confirmed by $^1$H NMR spectroscopy.

Preparation 23

(6-Hydroxy-2-oxo-3,4-dihydro-2H-quinolin-1-yl)-acetic acid tert-butyl ester

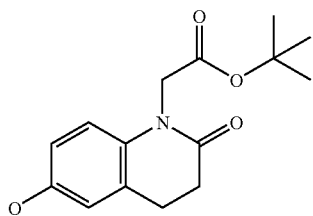

Step A

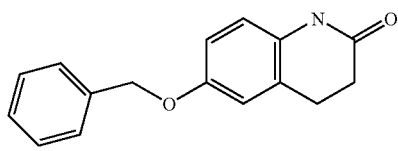

6-Benzyloxy-3,4-dihydro-1H-quinolin-2-one

A solution of 6-hydroxy-3,4-dihydro-1H-quinolin-2-one (2.93 g, 17.9 mmol) in DMF (20 mL) is treated with $K_2CO_3$ (4.97 g) and BnBr (4.61 g, 26.9 mmol). The suspension is stirred at room temperature for 4 hours and quenched with water (100 mL). The mixture is extracted with EtOAc (50 mL×2) and the combined organics are dried ($Na_2SO_4$), concentrated, and purified on silica gel chromatography column with 30-60% EtOAc/Hexanes to yield the title compound (4.40 g, 97%).

Step B

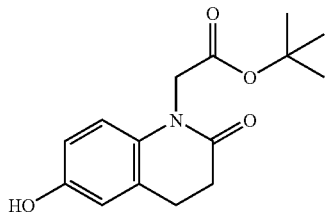

(6-Hydroxy-2-oxo-3,4-dihydro-2H-quinolin-1-yl)-acetic acid tert-butyl ester

A solution of 6-benzyloxy-3,4-dihydro-1H-quinolin-2-one (4.40 g, 17.4 mmol) in DMF (20 mL) is treated with NaH (1.40 g, 60%) in portions. Then t-butyl bromoacetate (5.09 g, 26.1 mmol) is added and the suspension is stirred at room temperature for 4 hours and quenched with water (100 mL). The mixture is extracted with EtOAc (50 mL×2) and the combined organics are dried ($Na_2SO_4$), concentrated, and purified on silica gel chromatography column with 20% EtOAc/Hexanes to obtain the intermediate compound.

The intermediate is dissolved in EtOH (10 mL) and EtOAc (20 mL) and the solution is treated with a slurry of Pd/C (50 mg). The suspension is stirred under a balloon of hydrogen gas for 12 hours. The mixture is then filter through a pad of celite and the filtrate is concentrated to afford the title compound (3.20 g, 66%).

Preparation 24

7-Hydroxy-3,4-dihydro-1H-quinolin-2-one

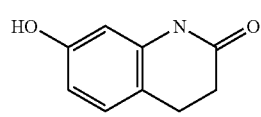

Step A

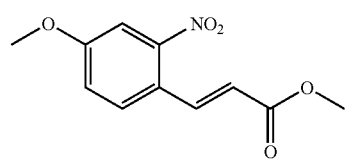

3-(4-Methoxy-2-nitro-phenyl)-acrylic acid methyl ester

A solution of 1-bromo-4-methoxy-2-nitro-benzene (12.56 g, 54.14 mmol) in acetonitrile (100 mL) is treated with Pd(OAc)$_2$ (1.21 g, 5.41 mmol) and tri-o-tolylphosphine (0.823 g, 2.707 mmol) and di-isopropyl ethyl amine (18.8 mL, 108 mmol). The mixture is degassed under vacuum and refilled with argon for three times. It is then heated to 110° C. and stirred for 2 hours. The mixture is then concentrated and purified on silica gel chromatography column with 10-20-30% EtOAc/Hexanes to obtain the title product (8.10 g, 63%).

Step B

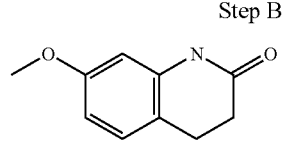

7-Methoxy-3,4-dihydro-1H-quinolin-2-one

A solution of 3-(4-methoxy-2-nitro-phenyl)-acrylic acid methyl ester (4.00 g, 16.9 mmol) in MeOH (100 mL) and EtOAc (20 mL) is added a slurry of Pd/C (200 mg) in EtOH (20 mL). The suspension is hydrogenated under a pressure of 60 psi for 12 hours. The mixture is then filter through a pad of celite and the filtrate is concentrated and purified on silica gel chromatography column with 30-40-50% EtOAc/Hexanes to obtain the title product (1.30 g, 43%) and an uncyclized by-product (0.60 g).

Step C

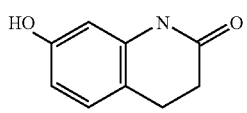

7-Hydroxy-3,4-dihydro-1H-quinolin-2-one

A solution of 7-methoxy-3,4-dihydro-1H-quinolin-2-one (1.30 g, 7.34 mmol) in $CH_2Cl_2$ (100 mL) at 0° C. is treated with $BBr_3$ (14.7 mL, 1.0 M in $CH_2Cl_2$) added dropwise. The mixture is stirred for 48 hours at room temperature and then quenched with water dropwise. The suspension is filtered and the solid is rinsed with MeOH (2 mL) and dried under vacuum to obtain the product (0.90 g, 75%).

Preparation 25

8-Hydroxy-1,3,4,5-tetrahydro-benzo[b]azepin-2-one

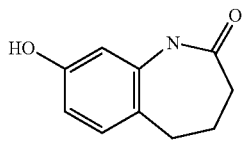

A solution of 8-methoxy-1,3,4,5-tetrahydro-benzo[b]azepin-2-one (116 mg, 0.607 mmol) in $CH_2Cl_2$ (20 mL) at 0° C. is treated with $BBr_3$ (1.2 mL, 1.0 M in $CH_2Cl_2$) added dropwise. The mixture is stirred for 16 hours at room temperature and then quenched with water dropwise. The suspension is filtered and the solid is rinsed with MeOH (1.0 mL) and dried under vacuum to obtain pure product (95 mg, 89%).

Preparation 26

3-Oxo-5-phenyl-pentanoic acid ethyl ester

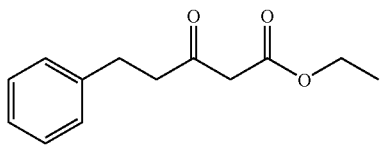

Ethyl acetoacetate (2.32 g, 20 mmol) is added to a pre-cold solution of LDA (2.0 M, 20 mL, 40 mmol) in THF (100 mL) at 0° C. After addition, the mixture is stirred for 30 min, then benzyl bromide (3.42 g, 20 mmol) is added dropwise. After stirred at 0° C. for 30 min, the reaction is quenched by 5 N HCl, extracted with ethyl ether. The combined organic layers are washed with water and brine until it is neutral. Concentration and column chromatography yields 1.6 g of the title compounds.

The following compounds are made in a similar manner:

Preparation 27

5-(2-Chloro-6-fluoro-phenyl)-3-oxo-pentanoic acid ethyl ester

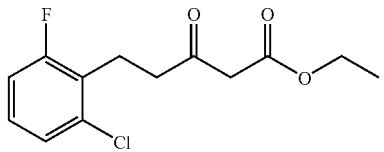

Preparation 28

3-Oxo-hept-6-enoic acid ethyl ester

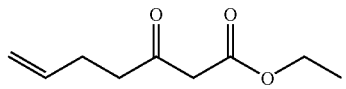

Preparation 29

2-Chloro-3-Oxo-5-phenyl-pentanoic acid ethyl ester

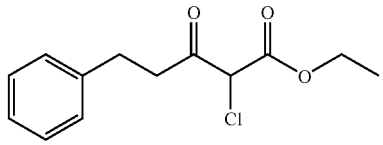

To a solution of 3-oxo-5-phenyl-pentanoic acid ethyl ester (1.6 g, 7.76 mmol) in methylene chloride (18 mL) is added sulfuryl chloride (1.15 g, 8.53 mmol) dropwise. After stirred at room temperature for 6 hours, the reaction mixture is poured into water, extracted with methylene chloride, washed wished water and brine, dried over sodium sulfate. Concentration yields the crude title compounds, which is used for the next step without further purification.

The following compounds are made in a similar manner:

Preparation 30

5-(2-Chloro-6-fluoro-phenyl)-2-chloro-3-oxo-pentanoic acid ethyl ester

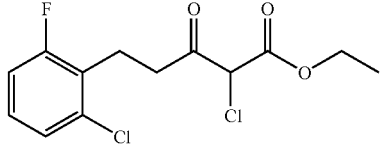

Preparation 31

2-Chloro-3-oxo-hept-6-enoic acid ethyl ester

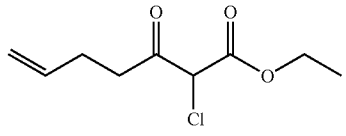

Preparation 32

2-Chloro-3-oxo-heptanoic acid ethyl ester

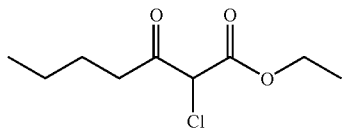

Preparation 33

2-Chloro-3-oxo-hexanoic acid ethyl ester

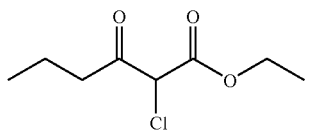

Preparation 34

2-Chloro-4-methyl-3-oxo-pentanoic acid ethyl ester

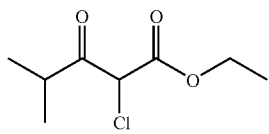

Preparation 35

2-Chloro-4,4-dimethyl-3-oxo-pentanoic acid ethyl ester

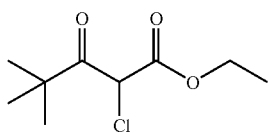

Preparation 36

2-Chloro-3-oxo-3-phenyl-propionic acid ethyl ester

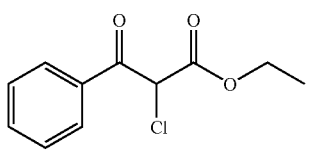

Preparation 37

2-(4-Bromo-phenyl)-4-methyl-thiazole-5-carboxylic acid ethyl ester

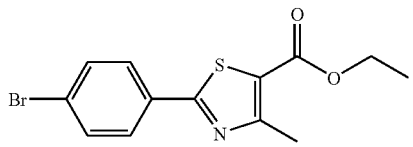

4-Bromo-thiobenzamide (5 g) in toluene is heated at reflux for 1 h in a flask equipped with a Dean-Stark trap. The dry 4-bromo-thioamide (3.4 g, 15 mmol) and ethyl 2-chloroacetoacetate (2.71 g, 16.4 mmol) are heated in ethanol (1000 mL) for overnight. The cooled reaction is concentrated and purified by short path chromatrography. The fractions that contained pure product are concentrated to yield 1.5 g (30.6%) ester as a solid.

The following thiazoles are made in a similar manner:

Preparation 38

4-Ethyl-2-(4-trifluoromethyl-phenyl)-thiazole-5-carboxylic acid ethyl ester

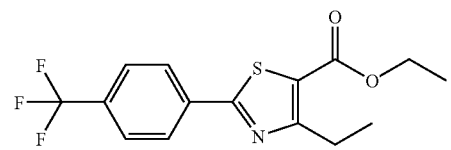

Preparation 39

4-Isopropyl-2-(4-trifluoromethyl-phenyl)-thiazole-5-carboxylic acid ethyl ester

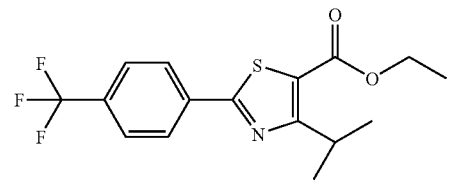

Preparation 40

4-Propyl-2-(4-trifluoromethyl-phenyl)-thiazole-5-carboxylic acid ethyl ester

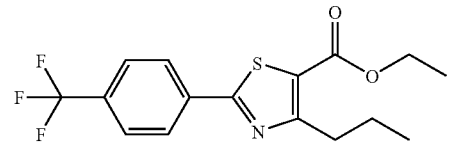

Preparation 41

4-Butyl-2-(4-trifluoromethyl-phenyl)-thiazole-5-carboxylic acid ethyl ester

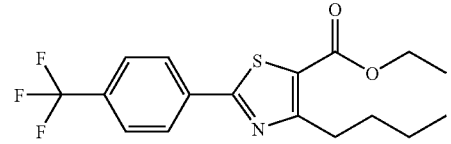

Preparation 42

4-But-3-enyl-2-(4-trifluoromethyl-phenyl)-thiazole-5-carboxylic acid ethyl ester

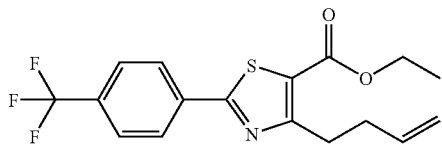

Preparation 43

4-tert-Butyl-2-(4-trifluoromethyl-phenyl)-thiazole-5-carboxylic acid ethyl ester

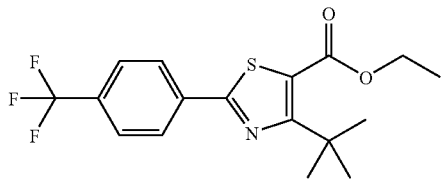

Preparation 44

4-Phenylethyl-2-(4-trifluoromethyl-phenyl)-thiazole-5-carboxylic acid ethyl ester

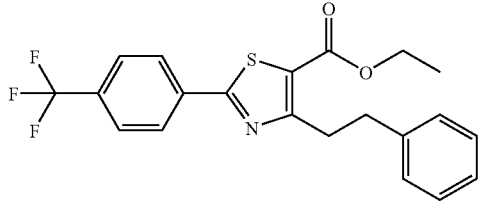

Preparation 45

4-[2-(2-Chloro-6-fluoro-phenyl)-ethyl]-2-(4-trifluoromethyl-phenyl)-thiazole-5-carboxylic acid ethyl ester

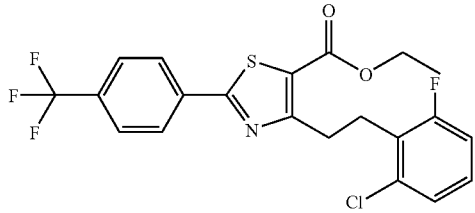

Preparation 46

4-Phenyl-2-(4-trifluoromethyl-phenyl)-thiazole-5-carboxylic acid ethyl ester

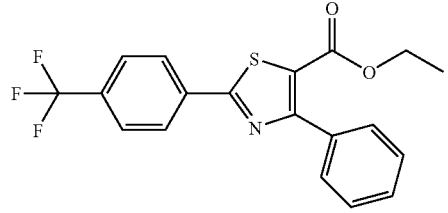

Preparation 47

4-Phenoxymethyl-2-(4-trifluoromethyl-phenyl)-thiazole-5-carboxylic acid ethyl ester

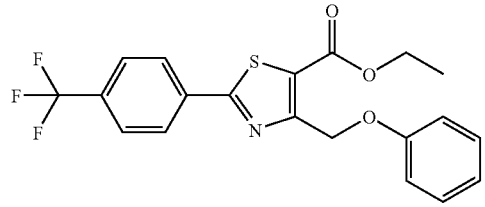

Step A

4-Bromomethyl-2-(4-trifluoromethyl-phenyl)-thiazole-5-carboxylic acid ethyl ester

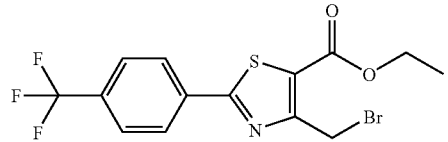

4-Methyl-2-(4-trifluoromethyl-phenyl)-thiazole-5-carboxylic acid ethyl ester (1.6 g, 5.00 mmol) is dissolved into chloroform (50 mL) then N-bromosuccinimide (1.0 g, 5.5 mmol) and 2,2'-azobisisobutyronitrile (0.412 g, 2.5 mmol) are added and the reaction is heated to reflux. The reaction is monitored by TLC until no starting material remained. The reaction is allowed to cool to room temperature, then diluted with more chloroform (100 mL). Water (50 mL) is added and the two phases are separated. The organic layer is washed with brine, then dried over anhydrous sodium sulfate. The material is then concentrated and further purified using flash column chromatography to yield 1.97 g or 99% yield.

Step B

4-Phenoxymethyl-2-(4-trifluoromethyl-phenyl)-thiazole-5-carboxylic acid ethyl ester Phenol (0.518 g, 5.5 mmol) is combined with anhydrous acetonitrile (20 mL) and cesium carbonate (2.3 g, 10 mmol) and allowed to stir at room temperature under nitrogen. To the reaction is added 4-bromomethyl-2-(4-trifluoromethyl-phenyl)-thiazole-5-carboxylic acid ethyl ester (1.97 g, 5.00 mmol). The reaction is monitored by TLC until all of the bromide is consumed. The reaction is diluted with ethyl ether (100 mL), then 0.1N NaOH (50 mL) is added. The two phases are separated, then the organic layer is washed with water (50 mL) and brine (50 mL). The organic layer is dried over anhydrous sodium sulfate, then concentrated. The material is further purified using flash chromatography to yield 1.75 g or 86% yield of the product.

The following compounds are made in a similar manner:

Preparation 48

4-(3,5-Bis-trifluoromethyl-phenoxymethyl)-2-(4-trifluoromethyl-phenyl)-thiazole-5-carboxylic acid ethyl ester

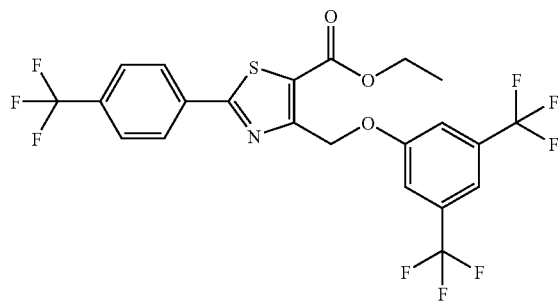

Preparation 49

4-(2-Chloro-6-fluoro-phenoxymethyl)-2-(4-trifluoromethyl-phenyl)-thiazole-5-carboxylic acid ethyl ester

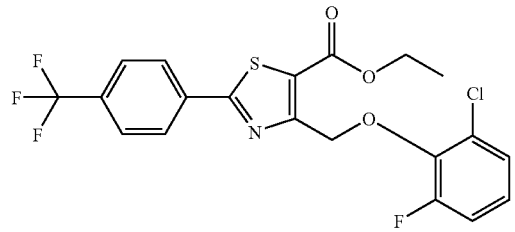

Preparation 50

4-(4-Bromo-phenylsulfanylmethyl)-2-(4-trifluoromethyl-phenyl)-thiazole-5-carboxylic acid ethyl ester

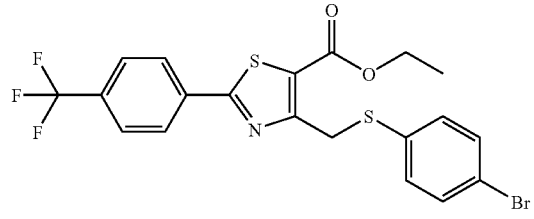

Preparation 51

4-Phenylsulfanylmethyl-2-(4-trifluoromethyl-phenyl)-thiazole-5-carboxylic acid ethyl ester

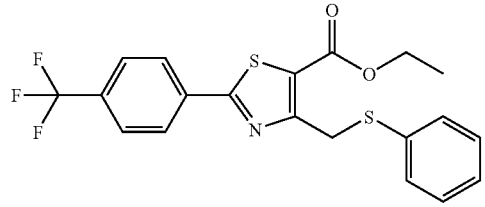

Preparation 52

[4-Methyl-2-(4-trifluoromethyl-phenyl)-thiazol-5-yl]-methanol

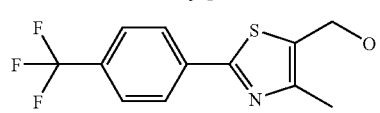

A THF (60 mL) solution of 4-methyl-2-(4-trifluoromethyl-phenyl)-thiazole-5-carboxylic acid ethyl ester (14.9 g, 47.3 mmol) is cooled to 0° C. and a 1M LiAlH$_4$ (47.3 mL, 47.3 mmol) is added slowly. The reaction is warmed to room temperature slowly, after stirring at room temperature for 2 h, tlc (15% EtOAc/hexane) showed that all the starting ester had been consumed. The reaction is cooled and carefully quenched with 2.4 mL water, 2.4 mL 5N NaOH and 7 mL water. The light tan solid is filter through celite and dried to give 7.70 g crude product. Recrystallization from methanol yields pure alcohol.

The following compounds are made in a similar manner:

Preparation 53

[4-Methyl-2-(4-bromo-phenyl)-thiazol-5-yl]-methanol

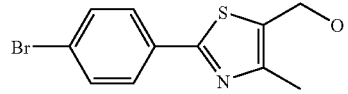

Preparation 54

[4-Ethyl-2-(4-trifluoromethyl-phenyl)-thiazol-5-yl]-methanol

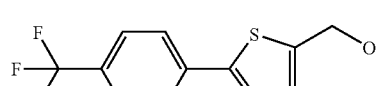

Preparation 55

[4-Isopropyl-2-(4-trifluoromethyl-phenyl)-thiazol-5-yl]-methanol

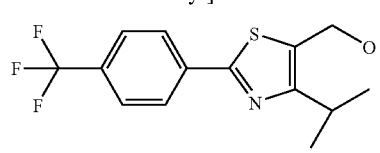

Preparation 56

[4-Propyl-2-(4-trifluoromethyl-phenyl)-thiazol-5-yl]-methanol

Preparation 57

[4-Butyl-2-(4-trifluoromethyl-phenyl)-thiazol-5-yl]-methanol

Preparation 58

[4-But-3-enyl-2-(4-trifluoromethyl-phenyl)-thiazol-5-yl]-methanol

Preparation 59

[4-tert-Butyl-2-(4-trifluoromethyl-phenyl)-thiazol-5-yl]-methanol

Preparation 60

4-Phenethyl-2-(4-trifluoromethyl-phenyl)-thiazol-5-yl]-methanol

Preparation 61

4-[2-(2-Chloro-6-fluoro-phenyl)-ethyl]-2-(4-trifluoromethyl-phenyl)-thiazol-5-yl]-methanol

Preparation 62

[4-Phenyl-2-(4-trifluoromethyl-phenyl)-thiazol-5-yl]-methanol

Preparation 63

[4-Phenoxymethyl-2-(4-trifluoromethyl-phenyl)-thiazol-5-yl]-methanol

Preparation 64

[4-(2-Chloro-6-fluoro-phenoxymethyl)-2-(4-trifluoromethyl-phenyl)-thiazol-5-yl]-methanol

Preparation 65

[4-(3,5-Bis-trifluoromethyl-phenoxymethyl)-2-(4-trifluoromethyl-phenyl)-thiazol-5-yl]-methanol

Preparation 66

[4-Phenylsulfanylmethyl-2-(4-trifluoromethyl-phenyl)-thiazol-5-yl]-methanol

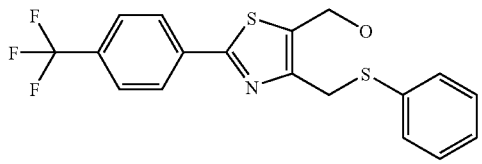

Preparation 67

[4-(4-Bromo-phenylsulfanylmethyl)-2-(4-trifluoromethyl-phenyl)-thiazol-5-yl]-methanol

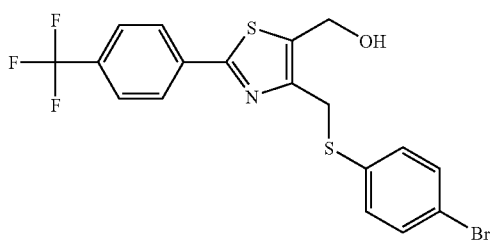

Preparation 68

5-Chloromethyl-4-methyl-2-(4-trifluoromethyl-phenyl)-thiazole

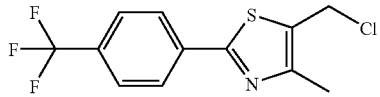

A solution of [4-methyl-2-(4-trifluoromethyl-phenyl)-thiazol-5-yl]-methanol (1.03 g, 3.75 mmol) and triethyl amine (1.05 mL, 7.5 mmol) in methylene chloride (15 mL) is cooled to 0° C., then MeSO2Cl is added dropwise. After 2 hrs, TLC indicated that the reaction is not complete, 10 mol % more of triethyl amine and MeSO$_2$Cl are added. After additional 2 hrs, the reaction mixture is diluted with methylene chloride and washed with sodium bicarbonate, water and brine, dried over sodium sulfate. Concentration yields the crude title compound, which is used for the next step without further purification.

The following compounds are made in a similar manner:

Preparation 69

5-Chloromethyl-4-methyl-2-(4-bromophenyl)-thiazole

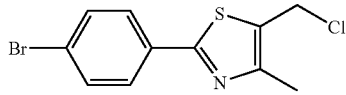

Preparation 70

5-Chloromethyl-4-isopropyl-2-(4-trifluoromethyl-phenyl)-thiazole

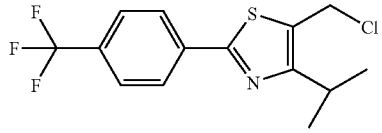

Preparation 71

5-Chloromethyl-4-propyl-2-(4-trifluoromethyl-phenyl)-thiazole

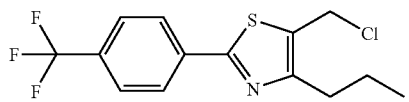

Preparation 72

5-Chloromethyl-4-butyl-2-(4-trifluoromethyl-phenyl)-thiazole

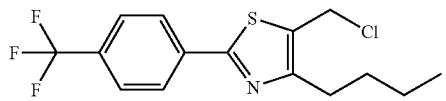

Preparation 73

4-But-3-enyl-5-chloromethyl-2-(4-trifluoromethyl-phenyl)-thiazole

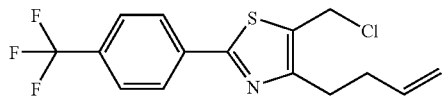

Preparation 74

5-Chloromethyl-4-tert-butyl-2-(4-trifluoromethyl-phenyl)-thiazole

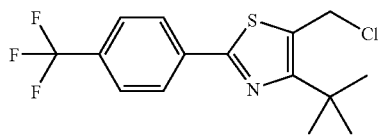

Preparation 75

5-Chloromethyl-4-phenethyl-2-(4-trifluoromethyl-phenyl)-thiazole

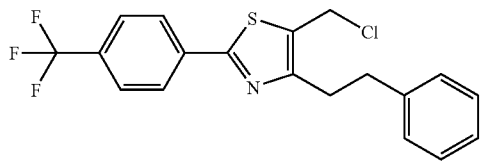

Preparation 76

5-Chloromethyl-4-[2-(2-Chloro-6-fluoro-phenyl)-ethyl]-2-(4-trifluoromethyl-phenyl)-thiazole

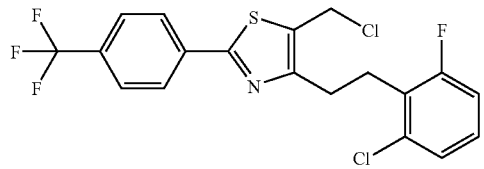

Preparation 77

5-Chloromethyl-4-phenoxymethyl-2-(4-trifluoromethyl phenyl)-thiazole

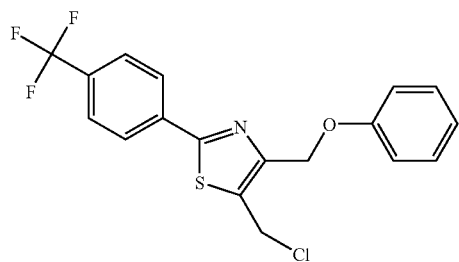

Preparation 78

4-(2-Chloro-6-fluoro-phenoxymethyl)-5-chloromethyl-2-(4-trifluoromethyl-phenyl)-thiazole

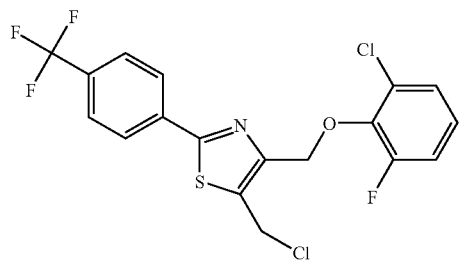

Preparation 79

4-(3,5-Bis-trifluoromethyl-phenoxymethyl)-5-chloromethyl-2-(4-trifluoromethyl-phenyl)-thiazole

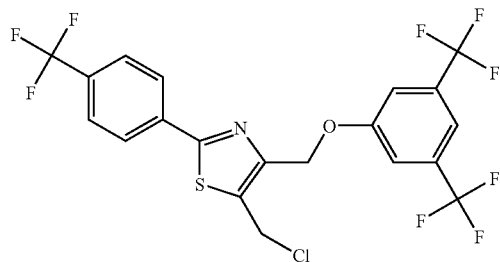

Preparation 80

5-Chloromethyl-4-phenylsulfanylmethyl-2-(4-trifluoromethyl-phenyl)-thiazole

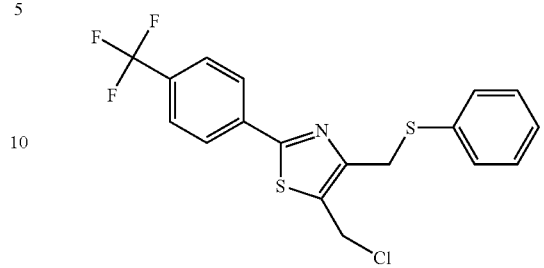

Preparation 81

4-(4-Bromo-phenylsulfanylmethyl)-5-chloromethyl-2-(4-trifluoromethyl-phenyl)-thiazole

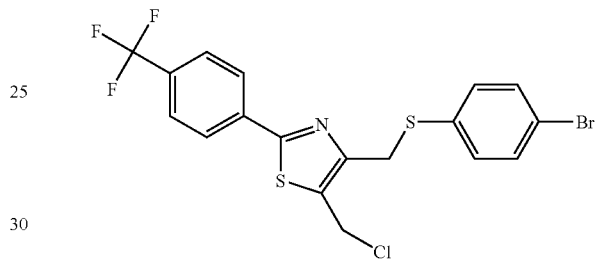

Preparation 82

5-Chloromethyl-4-ethyl-2-(4-trifluoromethyl-phenyl)-thiazole

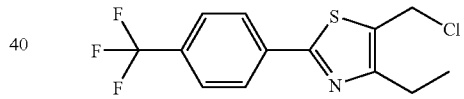

Preparation 83

2-(3,5-Bis-trifluoromethyl-phenyl)-5-chloromethyl-4-methyl-thiazole

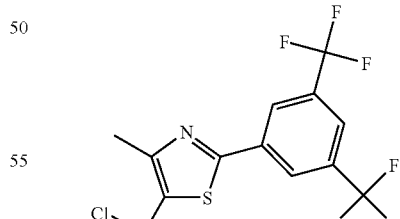

Step A

To a solution of 2-Bromo-4-methyl-thiazole-5-carboxylic acid methyl ester (0.850 g, 3.39 mmol) in toluene:ethanol (1:1) (30 mL) at room temperature under nitrogen is added 3,5-bistrifluormethylbenzene boronic acid (1.0 g, 3.74 mmol). The reaction is purged of air and flushed with nitrogen a few times, followed by addition of tetrakis triphenylphosphine palladium (0.200 g, 0.17 mmol) and sodium carbonate (2.7 mL, 2.5M soln., 6.8 mmol). The reaction is purged again, then heated to reflux under nitrogen and monitored by TLC. After complete consumption of the starting material, the reaction is allowed to cool to room temperature, then diluted with ethyl acetate, celite added, filtered, and the two phases are separated. The organic layer is washed, dried, filtered and concentrated. The crude 2-(3,5-Bis-trifluoromethyl-phenyl)-4-methyl-thiazole-5-carboxylic acid methyl ester (0.545 g, 1.42 mmol), 42% yield, is further purified using flash column chromatography.

Step B 2-(3,5-Bis-trifluoromethyl-phenyl)-4-methyl-thiazole-5-carboxylic acid methyl ester (0.545 g, 1.42 mmol), is dissolved in anhydrous tetrahydrofuran (6 mL) and cooled to 0° C. with stirring under nitrogen. Lithium aluminumhydride, 1.0M in THF, (1.40 mL, 1.40 mmol) is added and the reaction is monitored by TLC. After the starting material is completely consumed, the reaction is quenched with water, base, more water, and celite added, followed by dilution with ether. The mixture is filtered through a plug of celite and the two phases are separated. The organic layer is washed with water and brine, dried over sodium sulfate, then concentrated. The residue is further purified using flash column chromatography. The [2-(3,5-Bis-trifluoromethyl-phenyl)-4-methyl-thiazol-5-yl]-methanol (0.460 g, 1.35 mmol) is formed in 95% yield.

Step C

[2-(3,5-Bis-trifluoromethyl-phenyl)-4-methyl-thiazol-5-yl]-methanol (0.460 g, 1.35 mmol), is dissolved in anhydrous dichloromethane (6 mL) and cooled to 0° C. with stirring under nitrogen. Triethyl amine (0.350 mL, 2.60 mmol) and methane sulfonyl chloride (0.200 mL, 2.0 mmol) are added and the reaction is monitored by TLC. After the starting material is completely consumed, the reaction is diluted with dichloromethane and extracted against saturated sodium bicarbonate solution. The two phases are separated and the organic layer is washed with water and brine, dried over sodium sulfate, then concentrated. The residue is further purified using flash column chromatography. The 2-(3,5-Bis-trifluoromethyl-phenyl)-5-chloromethyl-4-methyl-thiazole is formed quantitatively and used without further purification.

Preparation 84

4-Ethyl-2-(4-trifluoromethyl-phenyl)-oxazole-5-carboxylic acid methyl ester

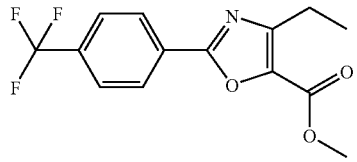

To a solution of 4-trifluoromethyl benzoic acid (0.100 g, 0.239 mmole) in methanol (2.0 mL), is added sodium hydroxide (0.093 g, 0.287 mmole) and stirred at room temperature for 2 hours. The mixture is concentrated to dryness in vacuo to give sodium 4-trifluoromethyl-benzoate as a white solid. It is then mixed with NH₄OAc (8.32 g, 107.9 mmole) in glacial acetic acid (500 mL) and heated at 100° C. for 16 hours. After removed the solvents on rota-vapor, the residue is partitioned between ethyl acetate (300 mL) and saturated sodium bicarbonate (300 mL). Extracted the aqueous layer with ethyl acetate (300 mL) one more time. The combined organic is wash with brine (3×500 mL), dried over Na₂SO₄, filtered and concentrated. The crude product is purified by chromatography on silica gel column, gradient elute with 0 to 10% ethyl acetate in hexane and concentrated to provide the titled compound as a white solid. Mass [EI+] 300 (M⁺+H).

Preparation 85

[4-Ethyl-2-(4-trifluoromethyl-phenyl)-oxazol-5-yl]-methanol

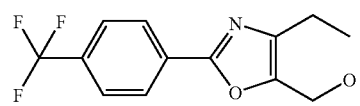

To a solution of 4-Ethyl-2-(4-trifluoromethyl-phenyl)-oxazole-5-carboxylic acid methyl ester (4.63 g, 15.47 mmole) in THF (100 mL), is added LiBH₄ in one portion at 0° C. The reaction is warmed up to room temperature and stirred for an hour. Additional LiBH₄ is added and the reaction is heated at 60° C. for 30 minutes. The excess amount of LiBH₄ is destroyed using 6N HCl (50 mL) dropwise at 0° C. The mixture is partitioned between ethyl acetate (300 mL) and brine (300 mL). The organic layer is washed with brine (3×300 mL), dried over Na₂SO₄, filtered and concentrated. The crude product is purified by flash chromatography, eluting with 60% ethyl acetate in hexane and concentrated to provide the titled compound as a white solid. Mass [EI+] 272 (M+H)⁺.

Preparation 86

[4-Methyl-2-(4-trifluoromethyl-phenyl)-oxazol-5-yl]-methanol

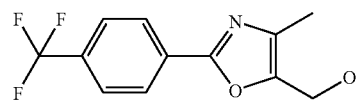

Step 1

2-(4-tert-Butyl-benzoylamino)-propionic acid methyl ester

D,L Alanine methyl ester (18.5 g, 132 mmol), triethylamine (42 mL, 300 mmol) and dichloromethane (300 mL) are stirred in an ice/water bath. 4-(Trifluromethyl)benzoyl chloride (25 g, 120 mmol) is added dropwise and the resulting mixture is allowed to stir for 20 hr at room temperature. 500 mL water and 100 mL 1M hydrochloric acid are successively added. The organic layer is separated, washed with 250 mL each of saturated sodium hydrogen carbonate, water, and brine, dried over anhydrous magnesium sulfate, filtered, and concentrated to 100 mL volume. The mixture is diluted with 200 mL hexanes, cooled to 0° C. for 1 hr, and the white solid filtered and dried under vacuum to afford 2-(4-tert-Butyl-benzoylamino)-propionic acid methyl ester, 26.5 g, 80%. MS (ES): 276 (M⁺+1).

Step 2

2-(4-tert-Butyl-benzoylamino)-propionic acid

A mixture of 2-(4-tert-Butyl-benzoylamino)-propionic acid methyl ester (26.3 g, 95.6 mmol), 200 mL 1M sodium hydroxide, and 100 mL tetrahydrofuran is stirred at room temperature 20 hr. The resulting clear solution is cooled on an ice/water bath and the pH is adjusted to 2 with concentrated hydrochloric acid. The product is extracted with three 250 mL portions of ethyl acetate. The combined extracts are washed with 100 mL each of water and brine, dried over anhydrous magnesium sulfate, filtered, and concentrated to afford 2-(4-tert-Butyl-benzoylamino)-propionic acid as a white solid, 24.6 g, 95%. MS M$^+$+1 260.

Step 3

[4-Methyl-2-(4-trifluoromethyl-phenyl)-oxazol-5-yl]-methanol

To a solution of 2-(4-Trifluoromethyl-benzoylamino)-propionic acid (33.4 g, 128 mmol) is added oxalyl chloride (111 mL, 1.27 Mol) and 1 drop of DMF and the solution stirred overnight. The volatiles are removed in vacuo and toluene (20 mL) is added. The toluene is then removed in vacuo. To the resultant crude oil is dissolve in 50 mL methylene chloride, cooled to 0° C. and triethylamine (27 mL, 192 mmol) is added followed by methanol (50 mL). After 3 hrs the volatiles are removed in vacuo and the crude oil is purified by flash column chromatography (20%-50% ethyl acetate/hexanes) to provide 12.6 g (35%) of 4-Methyl-2-(4-trifluoromethyl-phenyl)-oxazole-5-carboxylic acid methyl ester. This ester (2.0 g, 7.0 mmol) is reduced to the alcohol by dissolution in THF (50 mL) and adding 4 eq. LiBH$_4$ (0.610 g, 28.0 mmol) to provide 1.8 g (100%) [4-Methyl-2-(4-trifluoromethyl-phenyl)-oxazol-5-yl]-methanol. MS M$^+$+1 258.

Preparation 87

2-[5-Ethyl-2-(4-trifluoromethyl-phenyl)-thiazol-4-yl]-ethanol

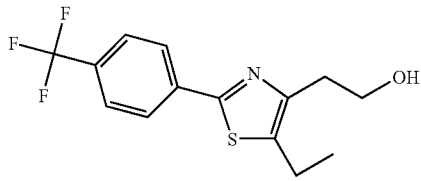

Preparation 88

2-[5-Propyl-2-(4-trifluoromethyl-phenyl)-thiazol-4-yl]-ethanol

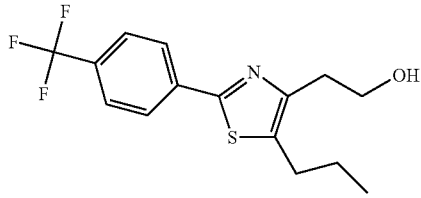

Preparation 89

Toluene-4-sulfonic acid 2-[5-propyl-2-(4-trifluoromethyl-phenyl)-thiazol-4-yl]-ethyl ester

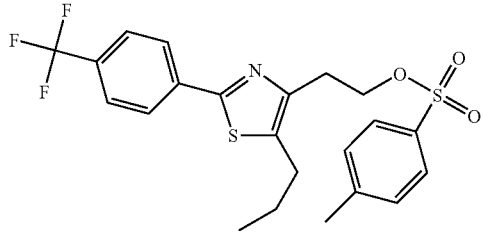

Step A

3-Oxo-heptanoic acid methyl ester (25 g, 0.157 Mol) is dissolved into anhydrous dichloromethane (DCM) (200 mL) and then cooled to 0° C.-5° C. while stirring. A solution of bromine (25.25 g, 0.160 Mol) in DCM (50 mL) is added dropwise over 2 h. to the solution of the beta keto-ester. After the addition, the mixture is allowed to stir 0.5 h. at 0° C., then the ice bath is removed and the mixture is allowed to stir at room temperature for 18 h. TLC will show complete consumption of starting material, then ice water (200 g) is added with stirring. The organic layer is collected and washed with cold water (2×) and brine. The filtered solution is dried over anhydrous sodium sulfate, then concentrated to a clear liquid. The crude 4-Bromo-3-oxo-heptanoic acid methyl ester (31.5 g, 0.135 Mol), 86% yield, is used without further purification.

Step B

4-Bromo-3-oxo-heptanoic acid methyl ester (6.0 g, 25.0 mmol) is dissolved into denatured ethanol (100 mL) and para-trifluoromethyl thiobenzamide (5.0 g, 24.4 mmol) is added in one portion. The reaction is purged of air and flushed with nitrogen then heated to reflux. The reaction is monitored by TLC and HPLC and when complete, the reaction is allowed to cool to room temperature. The solvent is removed and the reaction is diluted with ethyl acetate (200 mL), followed by washes with saturated sodium bicarbonate solution, water, and brine. The ethyl acetate solution is dried over anhydrous sodium sulfate, then concentrated and further purified using flash column chromatography (10% EtOAc/Hexanes) to yield pure [[5-Propyl-2-(4-trifluoromethyl-phenyl)-thiazol-4-yl]-acetic acid methyl ester (8.66 g, 24.2 mmol) or 98% yield.

Step C

[[5-Propyl-2-(4-trifluoromethyl-phenyl)-thiazol-4-yl]-acetic acid methyl ester (8.66 g, 24.2 mmol) is dissolved into anhydrous tetrahydrofuran (THF) (100 mL) and then cooled to 0° C. with stirring. Lithium aluminum hydride (24.2 mL, 1M in ThF, 24.2 mmol) is slowly added by syringe and the reaction is monitored by TLC. Upon complete conversion, the reaction is carefully quenched using water, base, and water. Celite is added to the reaction, followed by diethyl ether and the mixture is then filtered through a celite plug. The two phases are then separated and the organic layer is washed using water and brine. The organic layer is the dried over anhydrous sodium sulfate and concentrated. The pure 2-[5-Propyl-2-(4-trifluoromethyl-phenyl)-thiazol-4-yl]-ethanol (5.739 g, 18.2 mmol) is obtained in 75% yield after flash column chromatography.

Step D

The 2-[5-Propyl-2-(4-trifluoromethyl-phenyl)-thiazol-4-yl]-ethanol (5.739 g, 18.2 mmol) is dissolved into anhydrous dichloromethane (DCM) (100 mL) and dimethylamino pyridine (0.670 g, 5.46 mmol), tosic anhydride (11.9 g, 36.4 mmol), and pyridine (5 mL, 64 mmol) are added at room temperature. The reaction is monitored by TLC, and upon complete consumption of the starting alcohol, the reaction is diluted with DCM and extracted against saturated sodium bicarbonate solution. The organic layer is washed with water and brine, then dried over anhydrous sodium sulfate and concentrated. The pure Toluene-4-sulfonic acid 2-[5-propyl-2-(4-trifluoromethyl-phenyl)-thiazol-4-yl]-ethyl ester (4.46 g, 9.5 mmol) is obtained after flash column chromatography.

The following compounds are prepared in a similar manner:

Preparation 90

Toluene-4-sulfonic acid 2-[5-ethyl-2-(4-trifluoromethyl-phenyl)-thiazol-4-yl]-ethyl ester

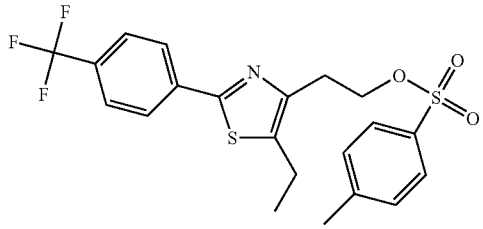

Preparation 91

Toluene-4-sulfonic acid 2-[2-(2-chloro-phenyl)-5-ethyl-thiazol-4-yl]-ethyl ester

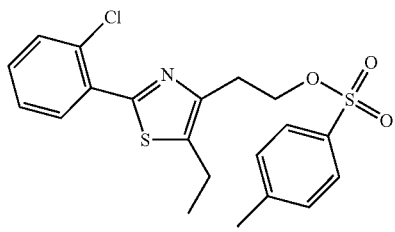

Preparation 92

4-Isopropyl-2-(4-trifluoromethyl-phenyl)-thiazole-5-carboxylic acid

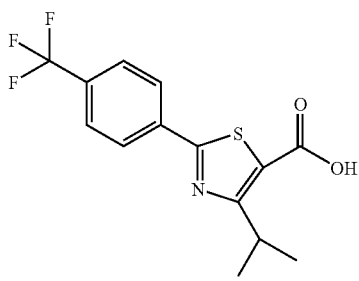

To a solution of 4-isopropyl-2-(4-trifluoromethyl-phenyl)-thiazole-5-carboxylic acid ethyl ester (0.62 g, 1.80 mmol) in THF (10 mL) is added 5M NaOH (3.5 mL, 17.50 mmol). The mixture is heated at 70° C. for 12 h. Upon cooling to RT, the mixture is acidified with 5M HCl and extracted with EtOAc. The organics are washed with water and brine, and dried with $MgSO_4$. After concentration, the title compound is obtained (0.46 g, 81%). The material is used without further purification.

The following compounds are made in a similar manner:

Preparation 93

[5-Ethyl-2-(4-trifluoromethyl-phenyl)-thiazol-4-yl]-acetic acid

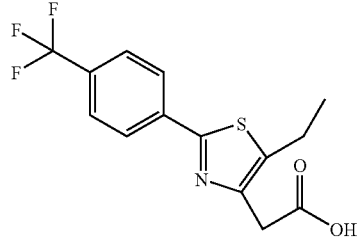

Preparation of 94

1-[4-Methyl-2-(4-trifluoromethyl-phenyl)-thiazol-5-yl]-ethanol

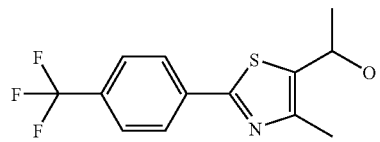

Step A

4-Methyl-2-(4-trifluoromethyl-phenyl)-thiazole-5-carbaldehyde

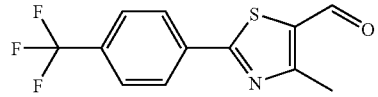

A mixture of [4-methyl-2-(4-trifluoromethyl-phenyl)-thiazol-5-yl]-methanol (5.0 g, 18.3 mmol) and MnO2 (2.4 g, 27.5 mmol) in chloroform (110 mL) are heated to reflux for 48 hrs, cooled to room temperature, filtered through celite. Concentration yields 5 gram of the title compound.

Step B

1-[4-Methyl-2-(4-trifluoromethyl-phenyl)-thiazol-5-yl]-ethanol To a solution of 4-methyl-2-(4-trifluoromethyl-phenyl)-thiazole-5-carbaldehyde (1.5 g, 5.53 mmole) in THF (50 mL) at 0° C., is added a solution of methyl magnesium bromide in diethyl ether (3.0M, 2.0 mL, 6.0 mmole) dropwise. The reaction is stirred for 5 minutes and then warmed up to room temperature for 2 hrs. The reaction is quenched with $NH_4Cl_{(aq)}$ (10 mL), partitioned between ethyl ether (50 mL) and water (50 mL). Extracted the aqueous layer with ethyl ether (2×50 mL). The combined organic is washed with brine (3×100 mL), dried over $Na_2SO_4$, filtered and concentrated. Column chromatography on silica gel yields 1.35 gram of the title compound.

The following compounds are made in a similar manner:

Preparation of 95

1-[4-isopropyl-2-(4-trifluoromethyl-phenyl)-thiazol-5-yl]-ethanol

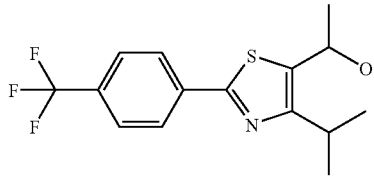

Preparation of 96

1-[4-Phenethyl-2-(4-trifluoromethyl-phenyl)-thiazol-5-yl]-ethanol

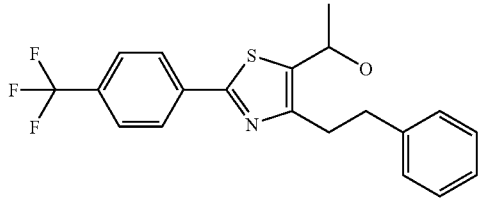

Preparation of 97

1-[4-[2-(2-Chloro-6-fluoro-phenyl)-ethyl]-2-(4-trifluoromethyl-phenyl)-thiazol-5yl]-ethanol

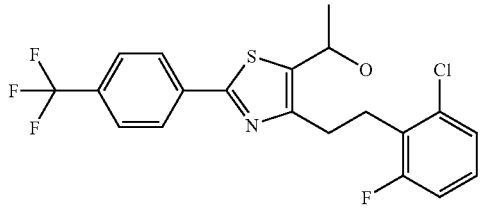

Preparation of 98

1-[4-Phenylsulfanylmethyl-2-(4-trifluoromethyl-phenyl)-thiazol-5-yl]-ethanol

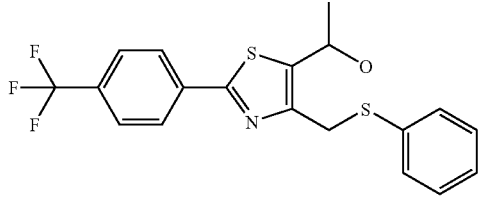

Preparation of 99

1-[4-(2-Chloro-6-fluoro-phenoxymethyl)-2-(4-trifluoromethyl-phenyl)-thiazol-5-yl]-ethanol

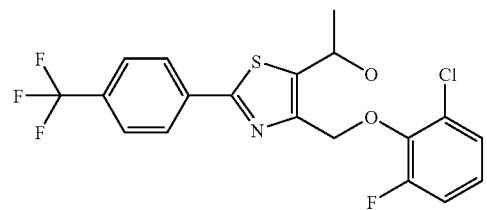

Preparation of 100

1-[4-(3,5-Bis-trifluoromethyl-phenoxymethyl)-2-(4-trifluoromethyl-phenyl)-thiazol-5-yl]-ethanol

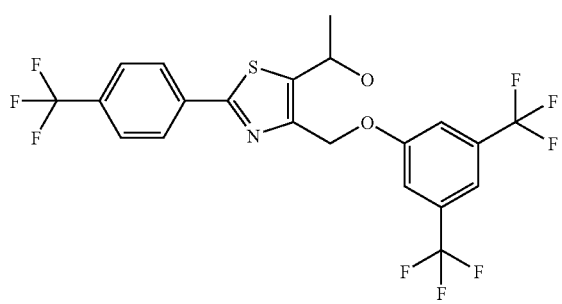

Preparation 101

1-[4-Phenyl-2-(4-trifluoromethyl-phenyl)-thiazol-5-yl]-ethanol

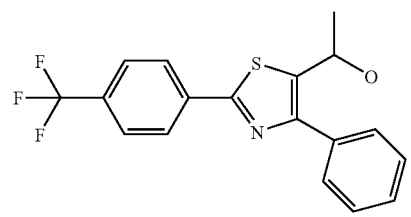

Preparation 102

1-[4-Methyl-2-(4-trifluoromethyl-phenyl)-thiazol-5-yl]-2-phenyl-ethanol

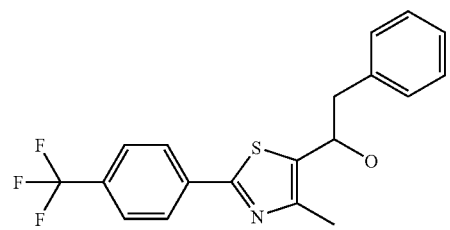

To a solution of 4-methyl-2-(4-trifluoromethyl-phenyl)-thiazole-5-carbaldehyde (0.5 g, 1.84 mmole) in THF (20 mL) at 0° C., is added a solution of benzyl magnesium chloride in tetrahedronfuran (2.0M, 1.0 mL, 2 mmole) dropwise. The reaction is stirred for 5 minutes and then warmed up to room Preparation 103

1-[2-(4-Bromo-phenyl)-4-isopropyl-oxazol-5-yl]-ethanol

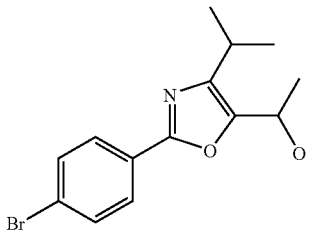

Step A 2-(4-Bromo-phenyl)-4-isopropyl-oxazole-5-carboxylic acid ethyl ester A solution of 4-bromo-benzoic acid (34.0 g, 0.169 mol) in DMF (450 mL) is treated at ambient temperature portionwise with NaH (6.4 g, 0.16 mol, 60% oil dispersion). The suspension is heated to 90° C. and 2-chloro-4-methyl-3-oxo-pentanoic acid ethyl ester (27.7 g, 0.144 mol) is added neat. The remaining chloride is washed into the reaction flask using DMF (25 mL). The reaction mixture is stirred for 18 h, cooled, and treated with water (600 mL). The mixture is extracted with EtOAc (750 mL). The organic layer is washed with brine (2×250 mL), dried ($Na_2SO_4$), and concentrated to a foam (56 g). This diester is dissolved in acetic acid (500 mL), treated at ambient temperature with ammonium acetate (80 g, 1.0 mol), and heated at 120° C. for 20 h. The reaction mixture is cooled, concentrated, and partitioned between EtOAc (500 mL) and saturated $NaHCO_3$ solution (3×125 mL). The organic layer is dried ($Na_2SO_4$), and concentrated. The crude product is purified by silica gel flash chromatography using hexanes:ethyl acetate (6:1) to give the title compound (26.6 g, 55%).

Step B

[2-(4-Bromo-phenyl)$_4$-isopropyl-oxazol-5-yl]-methanol

A solution of 2-(4-bromo-phenyl)-4-isopropyl-oxazole-5-carboxylic acid ethyl ester (20.6 g, 60.9 mmol) in THF (300 mL) is cooled in an ice-water bath and treated portionwise with $LiAlH_4$ (2.8 g, 73 mmol). The reaction is complete after 1.5 h. Ice chips (~10 g) are added to quench the excess hydride reagent, and anhydrous $Na_2SO_4$ (~50 g) is added. The thick suspension is stirred 30 min, filtered through celite, and washed with ThF (600 mL). The filtrate is dried ($Na_2SO_4$) and concentrated. The crude product is purified by silica gel flash chromatography using hexanes:ethyl acetate (3:1) to give a white solid (17.9 g, 99%).

Step C 2-(4-Bromo-phenyl)-4-isopropyl-oxazole-5-carbaldehyde

A solution of [2-(4-bromo-phenyl)-4-isopropyl-oxazol-5-yl]-methanol (17.9 g, 60.4 mmol) in $CH_2Cl_2$ (450 mL) is treated at ambient temperature with acetic acid 1,1-diacetoxy-3-oxo-1$\square^5$-ioda-2-oxa-indan-1-yl ester (39 g, 92 mmol, Dess Martin reagent). The suspension is stirred 1 h and is partitioned between 10% aqueous $Na_2S_2O_3$ solution (250 mL) and $CH_2Cl_2$ (150 mL). The organic layer is washed with saturated $NaHCO_3$ (2×250 mL), and the combined aqueous layers are back-extracted with $Et_2O$ (300 mL). The combined organic layers are dried ($Na_2SO_4$) and concentrated. The crude product is purified by silica gel flash chromatography using hexanes:ethyl acetate (6:1) to give an offwhite solid (14.4 g, 81%).

Step D

1-[2-(4-Bromo-phenyl)-4-isopropyl-oxazol-5-yl]-ethanol

A solution of 2-(4-bromo-phenyl)-4-isopropyl-oxazole-5-carbaldehyde (14.4 g, 84.9 mmol) in THF (300 mL) is cooled to −78° C. and treated dropwise with methyl magnesium bromide (25 mL, 75 mmol, 3M $Et_2O$). After 1 h, more methyl magnesium bromide (12 mL, 36 mmol) is added. The reaction mixture is stirred 1.5 h, and saturated $NH_4Cl$ solution (10 ml) is added dropwise. The mixture is partitioned between saturated $NH_4Cl$ solution (10 ml), 1N HCl (25 mL), and $Et_2O$ (300 mL). The organic layer is washed with brine (150 mL), dried ($Na_2SO_4$), and concentrated. The crude product is purified by silica gel flash chromatography using hexanes:ethyl acetate (9:1 to 5:1) to give an offwhite solid (9.5 g, 63%).

Preparation 104

1-[2-(-bromo-phenyl)-4-isopropyl-oxazol-5-yl]-ethanol

By the sequence above as preparation 78, 4-bromo-benzoic acid is converted to 1-[2-(4-bromo-phenyl)-4-isopropyl-oxazol-5-yl]-ethanol.

2-(3-Bromo-phenyl)-4-isopropyl-oxazole-5-carboxylic acid ethyl ester: 135 mmol scale, 35%

[2-(3-Bromo-phenyl)-4-isopropyl-oxazol-5-yl]-methanol: 45 mmol scale, 100%

2-(3-Bromo-phenyl)-4-isopropyl-oxazole-5-carbaldehyde: 45 mmol, 69%

1-[2-(3-Bromo-phenyl)-4-isopropyl-oxazol-5-yl]-ethanol: 29 mmol scale, 100%

Preparation 105

1-[4-Methyl-2-(4-trifluoromethyl-phenyl)-oxazol-5-yl]-ethanol

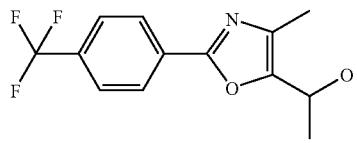

Step 1

2-(4-tert-Butyl-benzoylamino)-propionic acid methyl ester

D,L Alanine methyl ester (18.5 g, 132 mmol), triethylamine (42 mL, 300 mmol) and dichloromethane (300 mL) are stirred in an ice/water bath. 4-(Trifluromethyl)benzoyl chloride (25 g, 120 mmol) is added dropwise and the resulting mixture is allowed to stir for 20 hr at room temperature. 500 mL water and 100 mL 1M hydrochloric acid are successively added. The organic layer is separated, washed with 250 mL each of saturated sodium hydrogen carbonate, water, and brine, dried over anhydrous magnesium sulfate, filtered, and concentrated to 100 mL volume. The mixture is diluted with 200 mL hexanes, cooled to 0° C. for 1 hr, and the white solid filtered and dried under vacuum to afford 2-(4-tert-Butyl-benzoylamino)-propionic acid methyl ester, 26.5 g, 80%. MS (ES): 276 ($M^+$+1).

Step 2

2-(4-tert-Butyl-benzoylamino)-propionic acid

A mixture of 2-(4-tert-Butyl-benzoylamino)-propionic acid methyl ester (26.3 g, 95.6 mmol), 200 mL 1M sodium hydroxide, and 100 mL tetrahydrofuran is stirred at room temperature 20 hr. The resulting clear solution is cooled on an ice/water bath and the pH is adjusted to 2 with concentrated hydrochloric acid. The product is extracted with three 250 mL portions of ethyl acetate. The combined extracts are washed with 100 mL each of water and brine, dried over anhydrous magnesium sulfate, filtered, and concentrated to afford 2-(4-tert-Butyl-benzoylamino)-propionic acid as a white solid, 24.6 g, 95%. MS M++1 260.

Step 3

[4-Methyl-2-(4-trifluoromethyl-phenyl)-oxazol-5-yl]-methanol

To a solution of 2-(4-Trifluoromethyl-benzoylamino)-propionic acid (33.4 g, 128 mmol) is added oxalyl chloride (111 mL, 1.27 Mol) and 1 drop of DMF and the solution stirred overnight. The volatiles are removed in vacuo and toluene (20 mL) is added. The toluene is then removed in vacuo. To the resultant crude oil is dissolve in 50 mL methylene chloride, cooled to 0° C. and triethylamine (27 mL, 192 mmol) is added followed by methanol (50 mL). After 3 hrs the volatiles are removed in vacuo and the crude oil is purified by flash column chromatography (20%-50% ethyl acetate/hexanes) to provide 12.6 g (35%) of 4-Methyl-2-(4-trifluoromethyl-phenyl)-oxazole-5-carboxylic acid methyl ester. This ester (2.0 g, 7.0 mmol) is reduced to the alcohol by dissolution in THF (50 mL) and adding 4 eq. $LiBH_4$ (0.610 g, 28.0 mmol) to provide 1.8 g (100%) [4-Methyl-2-(4-trifluoromethyl-phenyl)-oxazol-5-yl]-methanol. MS $M^+$+1 258.

Step 4

4-Methyl-2-(4-trifluoromethyl-phenyl)-oxazole-5-carbaldehyde

[4-Methyl-2-(4-trifluoromethyl-phenyl)-oxazol-5-yl]-methanol (2.42 g, 9.41 mmol) and 100 mL dichloromethane are stirred at room temperature. Dess-Martin periodinane (8.0 g, 18.8 mmol) is added and the resulting mixture is stirred 4 hr at room temperature. The mixture is diluted with 100 mL saturated sodium hydrogen carbonate. The organic layer is separated, washed with 50 mL each of water and brine, dried over anhydrous magnesium sulfate, filtered, and concentrated. The crude product is purified by silica gel chromatography eluting with a mixture of 8:2 hexanes:ethyl acetate affording 4-methyl-2-(4-trifluoromethyl-phenyl)-oxazole-5-carbaldehyde as a white solid, 2.12 g, 89%. MS ($M^+$+1) 256.

Step 5

1-[4-Methyl-2-(4-trifluoromethyl-phenyl)-oxazol-5-yl]-ethanol

A solution of 4-methyl-2-(4-trifluoromethyl-phenyl)-oxazole-5-carbaldehyde (1.32 g, 5.16 mmol) and 50 mL tetrahydrofuran is stirred at 0° C. Methyl magnesium bromide (2.2 mL, 6.71 mmol, 3M) is added dropwise and the resulting mixture is allowed to stir at room temperature 30 min. The reaction is not complete, so an additional amount of methyl magnesium bromide (1 mL, 3 mmol) is added and the reaction stirred an additional 1 hr at room temperature. The mixture is cooled on an ice/water bath and aqueous ammonium chloride (10 mL) is added. The product is extracted with three 75 mL portions of ethyl acetate, the combined extracts are dried over anhydrous magnesium sulfate, filtered and concentrated. The crude product is purified by silica gel chromatography eluting with a mixture of 1:1 hexanes:ethyl acetate to afford 1-[4-Methyl-2-(4-trifluoromethyl-phenyl)-oxazol-5-yl]-ethanol as an ivory solid, 1.12 g, 80%. MS ($M^+$+1) 272.

Preparation 106

2-Methyl-1-[4-methyl-2-(4-trifluoromethyl-phenyl)-oxazol-5-yl]-propan-1-ol

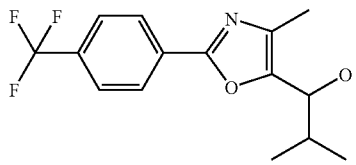

This compound is prepared in analogous fashion using preparation 105. Steps 1-4 are identical as previously described. Step 5 is performed using isoproyl magnesium bromide to afford 2-methyl-1-[4-methyl-2-(4-trifluoromethyl-phenyl)-oxazol-5-yl]-propan-1-ol.

Preparation 107

1-[4-Isopropyl-2-(4-trifluoromethyl-phenyl)-oxazol-5-yl]-ethanol

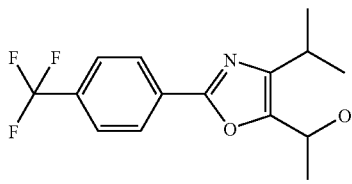

Step 1

2-chloro-4-methyl-3-oxo-pentanoic acid ethyl ester

Ethyl isobutyryl acetate (12.0 g, 75.85 mmol) is stirred at 0° C. in dichloromethane (75 mL). Sulfuryl chloride (6.5 mL, 80 mmol) is added dropwise and the resulting mixture is allowed to stir 20 hr at room temperature. The reaction mixture is cooled to 0° C. and aqueous saturated sodium hydrogen carbonate (200 mL) is added cautiously. The layers are separated, the aqueous layer is washed with dichloromethane (100 mL), the combined organic layers are washed with water and brine (100 mL each), dried over anhydrous magnesium sulfate, filtered, and concentrated to constant weight to give 2-chloro-4-methyl-3-oxo-pentanoic acid ethyl ester as a colorless oil, 14.6 g, 100%. MS (M$^+$+1) 193.

Step 2

4-Isopropyl-2-(4-trifluoromethyl-phenyl)-oxazole-5-carboxylic acid ethyl ester

Sodium Hydride, 60% mineral oil (1.9 g, 46.3 mmol) and dimethylformamide (50 mL) are stirred at room temperature and 4-(trifluoromethyl)benzoic acid (8.0 g, 42.1 mmol) is added. To the resulting slurry is added 2-chloro-4-methyl-3-oxo-pentanoic acid ethyl ester (8.5 g, 44.2 mmol) and the resulting mixture is heated to 90° C. for 3 hr. The reaction mixture is cooled, diluted with water (100 mL), and product is extracted with ethyl acetate (100 mL). The organic layer is washed with water (three 100 mL portions) and brine (100 mL), dried over anhydrous magnesium sulfate, filtered, and concentrated to constant weight to give 4-trifluoromethyl-benzoic acid 1-ethoxycarbonyl-3-methyl-2-oxo-butyl ester as a colorless oil, 14.6 g, 100%. The resulting oil is stirred in a mixture of acetic acid (100 mL) and ammonium acetate (9.75 g, 126.5 mmol) at reflux 1 hr, then 20 hr at room temperature. The solvent is removed in vacuo and the residue is partitioned between aqueous saturated sodium hydrogen carbonate (100 mL) and ethyl acetate (100 mL. The layers are separated, the aqueous layer is washed with ethyl acetate (100 mL). The organic extracts are combined, washed with water and brine (100 mL each) dried over anhydrous magnesium sulfate, filtered, and concentrated. The residue is purified over silica eluting with 9:1 hexanes:ethyl acetate to afford 4-Isopropyl-2-(4-trifluoromethyl-phenyl)-oxazol-5-carboxylic acid ethyl ester as a white solid, 8.1 g, 60%. MS (M$^+$+1) 328.

Step 3

[4-Isopropyl-2-(4-trifluoromethyl-phenyl)-oxazol-5-yl]-methanol

4-Isopropyl-2-(4-trifluoromethyl-phenyl)-oxazole-5-carboxylic acid ethyl ester (0.53 g, 1.62 mmol) is stirred in tetrahydrofuran (25 mL) at 0° C. Lithium aluminum hydride (0.122 g, 3.23 mmol) is added and the mixture is stirred 18 hr at room temperature. The mixture is diluted carefully with 1M aqueous hydrochloric acid (10 mL), and the product is extracted with ethyl acetate (three 75 mL portions). The extracts are combined, dried over anhydrous magnesium sulfate, filtered, and concentrated to afford [4-Isopropyl-2-(4-trifluoromethyl-phenyl)-oxazol-5-yl]-methanol as a white solid, 0.46 g, 100%. MS (M$^+$+1) 286

Step 4

4-Isopropyl-2-(4-trifluoromethyl-phenyl)-oxazole-5-carbaldehyde

[4-Isopropyl-2-(4-trifluoromethyl-phenyl)-oxazol-5-yl]-methanol (0.46 g, 1.612 mmol), Dess-Martin periodinane (1.36 g, 3.22 mmol) and dichloromethane (25 mL) are stirred 1 hr at room temperature. The mixture is diluted with aqueous saturated sodium hydrogen carbonate (100 mL) and dichloromethane (100 mL). The layers are separated, the aqueous layer is washed with dichloromethane (100 mL). The organic washes are combined, washed with brine (50 mL), dried over anhydrous magnesium sulfate, filtered, and concentrated in vacuo. The product is purified over silica eluting with 3:1 hexanes:ethyl acetate to afford 4-Isopropyl-2-(4-trifluoromethyl-phenyl)-oxazole-5-carbaldehyde as a white solid, 0.41 g, 90%. %. MS (M$^+$+1) 284.

Step 5

1-[4-Isopropyl-2-(4-trifluoromethyl-phenyl)-oxazol-5-yl]-ethanol

Followed a similar procedure in step 5 of preparation 105.

Preparation 108

1-[4-tert-Butyl-2-(4-trifluoromethyl-phenyl)-oxazol-5-yl]-ethanol

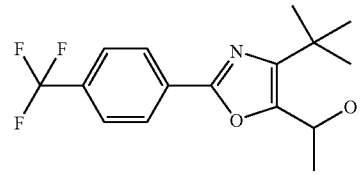

Preparation 109

1-[4-Methyl-2-(4-trifluoromethyl-phenyl)-oxazol-5-yl]-propan-1-ol

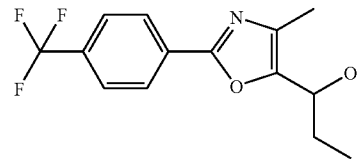

Step 1

4-methyl-2-(4-trifluoromethyl-phenyl)-oxazole-5-carboxylic acid methoxy-methyl-amide To a solution of 2-(4-Trifluoromethyl-benzoylamino)-propionic acid (5.0 g, 19.14 mmol) is added oxalyl chloride (16.7 mL, 191.4 mmol) and 2 drops of DMF and the solution stirred overnight. The volatiles are removed in vacuo and toluene (20 mL) is added. The toluene is then removed in vacuo. To the resultant crude oil is dissolve in dichloromethane (100 mL), cooled to 0° C. and triethylamine (13.4 mL, 96 mmol) is added followed by N,O-dimethyl hydroxylamine hydrochloride (9.4 g, 96 mmol). After 1 hr the mixture is partitioned between 1M aqueous hydrochloric acid and ethyl acetate. The organic layer is dried over anhydrous magnesium sulfate, filtered, concentrated in vacuo. The product is purified over silica eluting with 8:2 hexanes:ethyl acetate to afford 4-methyl-2-(4-trifluoromethyl-phenyl)-oxazole-5-carboxylic acid methoxy-methyl-amide as a white crystalline solid, 2.4 g, 40%. MS (M$^+$+1)315.

Step 2

1-[4-methyl-2-(4-trifluoromethyl-phenyl)-oxazol-5-yl]-propan-1-one 4-methyl-2-(4-trifluoromethyl-phenyl)-oxazole-5-carboxylic acid methoxy-methyl-amide (1.0 g, 3.18 mmol) is stirred in tetrahydrofuran (15 mL) at −78° C. Ethyl magnesium bromide, 3M/ether (2.1 mL, 4.14 mmol) is added and the mixture is warmed to room temperature. The mixture is diluted with aqueous saturated ammonium chloride and washed with ethyl acetate (three 50 mL portions). The combined washes are dried over anhydrous magnesium sulfate, filtered and concentrated in vacuo. The residue is purified over silica eluting with 7:3 hexanes:ethyl acetate to afford 1-[4-methyl-2-(4-trifluoromethyl-phenyl)-oxazol-5-yl]-propan-1-one as an ivory solid, 0.70 g, 78%. MS (M$^+$+1)284.

Step 3

1-[4-methyl-2-(4-trifluoromethyl-phenyl)-oxazol-5-yl]-propan-1-ol

1-[4-methyl-2-(4-trifluoromethyl-phenyl)-oxazol-5-yl]-propan-1-one (0.68 g, 2.4 mmol) and tetrahydrofuran (5 mL) are stirred at 0° C. Lithium borohydride (0.14 g, 6.36 mmol) is added and the mixture is stirred 10 min at 0° C., and 30 min at room temperature. The mixture is diluted with 1M aqueous hydrochloric acid and washed with ethyl acetate (three 50 mL portions). The organic washes are dried over anhydrous magnesium sulfate, filtered, and concentrated in vacuo. The residue is purified over silica eluting with 8:2 hexanes:ethyl acetate to 1:1 hexanes ethyl acetate to afford 1-[4-methyl-2-(4-trifluoromethyl-phenyl)-oxazol-5-yl]-propan-1-ol as an ivory solid, 0.69 g, 100%. MS (M$^+$+1)286.

Preparation 110

1-[4-Methyl-2-(4-trifluoromethyl-phenyl)-oxazol-5-yl]-but-3-en-1-ol

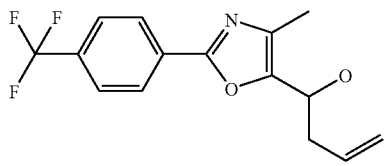

Preparation 111

1-[4-Methyl-2-(4-trifluoromethyl-phenyl)-oxazol-5-yl]-pentan-1-ol

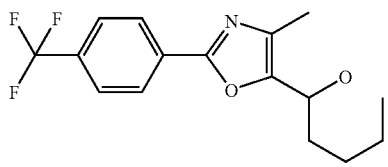

Preparation 112

1-[4-Isopropyl-2-(4-trifluoromethoxy-phenyl)-oxazol-5-yl]-ethanol

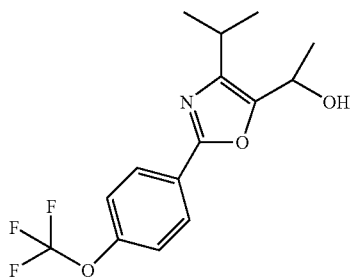

Preparation 113

1-[2-(4-Bromo-phenyl)-4-isopropyl-oxazol-5-yl]-ethanol

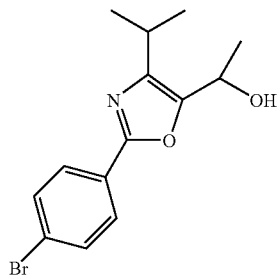

Preparation 114

2-[4-Isopropyl-2-(4-trifluoromethyl-phenyl)-oxazol-5-yl]-propan-1-ol

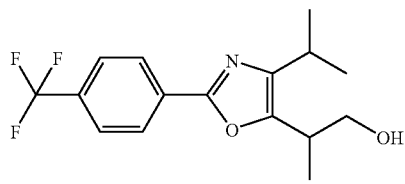

Step 1

4-Isopropyl-2-(4-trifluoromethyl-phenyl)-4H-oxazol-5-one

3-Methyl-2-(4-trifluoromethyl-benzoylamino)-butyric acid methyl ester (4.75 g, 16.42 mmol) is dissolved in acetic anhydride (25 mL) and heated to 95° C. for 3 hr. The mixture is concentrated in vacuo and the residue is partitioned between aqueous saturated sodium hydrogen carbonate (100 mL) and ethyl acetate (100 mL) the layers are separated, the organic phase is washed with water and brine (100 mL each), dried over anhydrous magnesium sulfate, filtered, concentrated in vacuo, and purified over silica gel eluting with 9:1 hexanes:ethyl acetate to afford 4-Isopropyl-2-(4-trifluoromethyl-phenyl)-4H-oxazol-5-one as a colorless oil which solidifies to a white crystalline solid on standing, 4.14 g, 93%. MS (M$^+$+1) 272.

Step 2

2-[4-Isopropyl-2-(4-trifluoromethyl-phenyl)-oxazol-5-yl]-propionic acid ethyl ester 4-Isopropyl-2-(4-trifluoromethyl-phenyl)-4H-oxazol-5-one (1.0 g, 3.69 mmol) and (carbethoxyethylidine)triphenylphosphorane (2.67 g, 7.37 mmol) are stirred in toluene (20 mL) at reflux 3 hr. The mixture is concentrated in vacuo and the residue is purified over silica eluting with 9:1 hexanes:ethyl acetate affording 2-[4-Isopropyl-2-(4-trifluoromethyl-phenyl)-oxazol-5-yl]-propionic acid ethyl ester as a pale orange oil, 1.11 g, 85%. MS (M$^+$+1) 356.

Step 3

2-[4-Isopropyl-2-(4-trifluoromethyl-phenyl)-oxazol-5-yl]-propan-1-ol

2-[4-Isopropyl-2-(4-trifluoromethyl-phenyl)-oxazol-5-yl]-propionic acid ethyl ester (1.11 g, 3.12 mmol) and tetrahydrofuran (50 mL) are cooled to 0° C. Lithium aluminum hydride (0.24 g, 6.25 mmol) is added and the resulting mixture is stirred 20 hr at room temperature. The mixture is cooled to 0° C. and 1M aqueous hydrochloric acid (50 mL) is carefully added. The mixture is then diluted with ethyl acetate (100 mL) and the layers are separated. The aqueous layer is washed with ethyl acetate (100 mL) and the organic washes are combined, washed with water and brine (50 mL each), dried over anhydrous magnesium sulfate, filtered and concentrated to constant weight to give 2-[4-Isopropyl-2-(4-trifluoromethyl-phenyl)-oxazol-5-yl]-propan-1-ol as a pale orange oil, 1.03 g, 100%. MS (M$^+$+1) 314. The following compound is made in similar manner:

Preparation 115

2-[4-Isopropyl-2-(4-trifluoromethoxy-phenyl)-oxazol-5-yl]-propan-1-ol

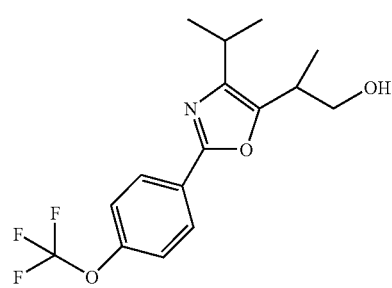

Preparation 116

2-[4-Isopropyl-2-(4-phenoxy-phenyl)-oxazol-5-yl]-propan-1-ol

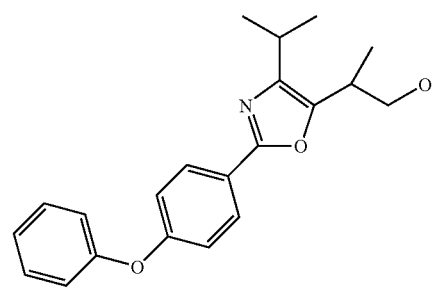

Preparation 117

2-[2-(4-Bromo-phenyl)-4-isopropyl-oxazol-5-yl]-propan-1-ol

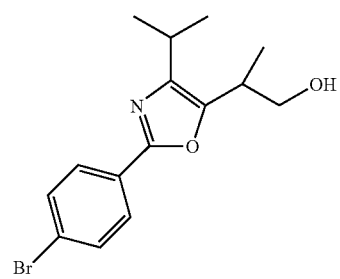

Preparation 118

2-[5-Methyl-2-(4-trifluoromethyl-phenyl)-thiazol-4-yl]-propan-1-ol and 2-Methyl-2-[5-methyl-2-(4-trifluoromethyl-phenyl)-thiazol-4-yl]-propan-1-ol

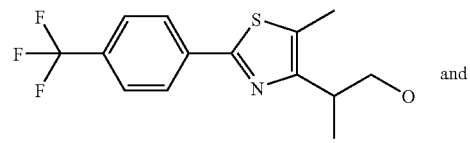

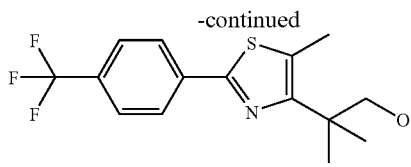

Step A

4-Bromo-2-methyl-3-oxo-pentanoic acid methyl ester and 4-Bromo-2,2-dimethyl-3-oxo-pentanoic acid methyl ester A solution of bromine (18.4 g, 115 mmol) in chloroform (30 mL) is added to a mixture of 2-methyl-3-oxo-pentanoic acid methyl ester and 2,2-dimethyl-3-oxo-pentanoic acid methyl ester (16.5 g) in chloroform (120 mL) at 0-5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration yields the title compounds, which is used for next step without further purification.

Step B

2-[5-Methyl-2-(4-trifluoromethyl-phenyl)-thiazol-4-yl]-propionic acid methyl ester and 2-Methyl-2-[5-methyl-2-(4-trifluoromethyl-phenyl)-thiazol-4-yl]-propionic acid methyl ester A mixture of 4-Trifluoromethyl-thiobenzamide (7.70 g, 37.5 mmol) and the crude product from step A (9.0 g, 40 mmol) in ethanol (500 mL) is heated to reflux for 4 days. Solvent is evaporated and the residue is purified by chromatography on silica gel yielding the title compounds (11 g).

Step C

2-[5-Methyl-2-(4-trifluoromethyl-phenyl)-thiazol-4-yl]-propan-1-ol and 2-Methyl-2-[5-methyl-2-(4-trifluoromethyl-phenyl)-thiazol-4-yl]-propan-1-ol To a solution of 2-[5-Methyl-2-(4-trifluoromethyl-phenyl)-thiazol-4-yl]-propionic acid methyl ester and 2-Methyl-2-[5-methyl-2-(4-trifluoromethyl-phenyl)-thiazol-4-yl]-propionic acid methyl ester (10.6 g) in THF (50 mL) is added a solution of lithium aluminum hydride in THF (1.0 M, 33 mL) at 0° C. After 2 hrs, the reaction is quenched by water and sodium hydroxide, filtered, concentrated. Chromatography on silica gel yields 2-[5-Methyl-2-(4-trifluoromethyl-phenyl)-thiazol-4-yl]-propan-1-ol (4.3 g) and 2-Methyl-2-[5-methyl-2-(4-trifluoromethyl-phenyl)-thiazol-4-yl]-propan-1-ol (2.6 g).

Preparation 119

2-[5-Methyl-2-(4-trifluoromethyl-phenyl)-oxazol-4-yl]-propan-1-ol and 2-Methyl-2-[5-methyl-2-(4-trifluoromethyl-phenyl)-oxazol-4-yl]-propan-1-ol

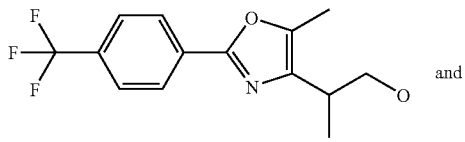

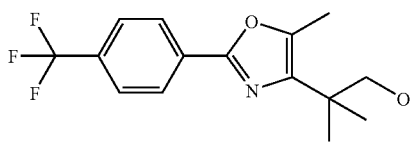

Step A

4-Bromo-2-methyl-3-oxo-pentanoic acid methyl ester and 4-Bromo-2,2-dimethyl-3-oxo-pentanoic acid methyl ester A solution of bromine (18.4 g, 115 mmol) in chloroform (20 mL) is added to a mixture of 2-methyl-3-oxo-pentanoic acid methyl ester and 2,2-dimethyl-3-oxo-pentanoic acid methyl ester (ca. 115 mmol) in chloroform (120 mL) at 0-5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration yields the title compounds, which is used for next step without further purification.

Step B

2-[5-Methyl-2-(4-trifluoromethyl-phenyl)-oxazol-4-yl]-propionic acid methyl ester and 2-Methyl-2-[5-methyl-2-(4-trifluoromethyl-phenyl)-oxazol-4-yl]-propionic acid methyl ester To a solution of 4-Trifluoromethyl-benzoic acid (7.6 g, 40 mmol) in methanol (100 mL) is added sodium hydroxide (1.6 g, 40 mmol), stirred for 30 min, methanol is evaporated. The residue is taken into DMF (50 mL) and the crude product from step A (10 g) is added. The mixture is stirred overnight, diluted with ethyl acetate, washed with water and brine, dried over sodium sulfate, concentrated. The residue is taken into ethanol (150 mL) and treated with ammonium acetate (6.17 g) and heated at 70° C. for 12 hrs. Ethanol is evaporated, the residue is mixed with ammonium acetate (12.3 g) in glacial acid (750 mL) and heated at 100° C. for 2 days. Solvent is evaporated and the residue is taken into ethyl acetate, washed with water and brine, dried. Chromatography on silica gel yields 2-[5-Methyl-2-(4-trifluoromethyl-phenyl)-oxazol-4-yl]-propionic acid methyl ester (3.40 g) and 2-Methyl-2-[5-methyl-2-(4-trifluoromethyl-phenyl)-oxazol-4-yl]-propionic acid methyl ester (2.80 g).

Step C

2-[5-Methyl-2-(4-trifluoromethyl-phenyl)-oxazol-4-yl]-propan-1-ol

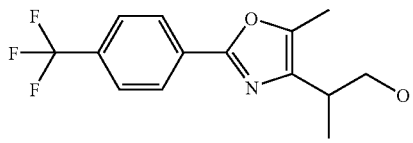

To a solution of 2-[5-methyl-2-(4-trifluoromethyl-phenyl)-ozazol-4-yl]-propionic acid methyl ester (3.4 g) from step B in THF (20 mL) is added a solution of lithium aluminum hydride in THF (1.0 M, 14 mL) at 0° C. After 2 hrs, the reaction is quenched by water and sodium hydroxide, filtered, concentrated. Chromatography on silica gel yields 2-[5-Methyl-2-(4-trifluoromethyl-phenyl)-oxazol-4-yl]-propan-1-ol (0.88 g).

Step D and 2-Methyl-2-[5-methyl-2-(4-trifluoromethyl-phenyl)-oxazol-4-yl]-propan-1-ol

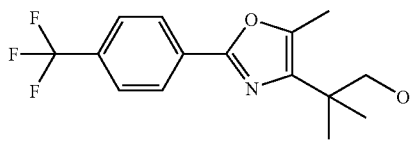

To a solution of 2-methyl-2-[5-methyl-2-(4-trifluoromethyl-phenyl)-oxiazol-4-yl]-propionic acid methyl ester (2.8 g) from step B in THF (14 mL) is added a solution of lithium aluminum hydride in THF (1.0 M, 13 mL) at 0° C. After 2 hrs, the reaction is quenched by water and sodium hydroxide, filtered, concentrated. Chromatography on silica gel yields 2-Methyl-2-[5-methyl-2-(4-trifluoromethyl-phenyl)-oxazol-4-yl]-propan-1-ol (2.3 g).

Preparation 120

2-Methyl-2-[5-ethyl-2-(4-trifluoromethyl-phenyl)-thiazol-4-yl]-propan-1-ol

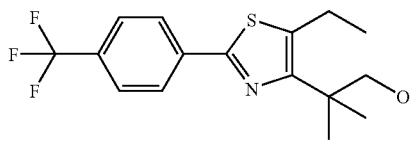

Step A

4-Bromo-2,2-dimethyl-3-oxo-hexanoic acid methyl ester

A solution of bromine (24 g, 150 mmol) in chloroform (30 mL) is added to 2,2-dimethyl-3-oxo-hexanoic acid methyl ester (25.9 g, 150 mmol) in chloroform (126 mL) at 0-5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration yields the title compounds (36.9 g), which is used for next step without further purification.

Step B

2-Methyl-2-[5-ethyl-2-(4-trifluoromethyl-phenyl)-thiazol-4-yl]-propionic acid methyl ester A mixture of 4-Trifluoromethyl-thiobenzamide (12.3 g, 60 mmol) and the crude product from step A (16.6 g, 66 mmol) in ethanol (600 mL) is heated to reflux for 3 days. Solvent is evaporated and the residue is purified by chromatography on silica gel yielding the title compounds (14.5 g).

Step C

2-Methyl-2-[5-ethyl-2-(4-trifluoromethyl-phenyl)-thiazol-4-yl]-propan-1-ol

To a solution of 2-Methyl-2-[5-ethyl-2-(4-trifluoromethyl-phenyl)-thiazol-4-yl]-propionic acid methyl ester (14.5 g, 40.6 mmol) in THF (100 mL) is added a solution of lithium aluminum hydride in THF (1.0 M, 41 mL) at 0° C. After 2 hrs, the reaction is quenched by water and sodium hydroxide, filtered, concentrated. Chromatography on silica gel yields 2-Methyl-2-[5-ethyl-2-(4-trifluoromethyl-phenyl)-thiazol-4-yl]-propan-1-ol (12.3 g).

Preparation 121

2-[4-Methyl-2-(4-trifluoromethyl-phenyl)-thiazol-5-yl]-propan-1-ol

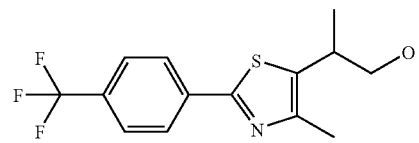

Step A

1-[4-Methyl-2-(4-trifluoromethyl-phenyl)-thiazol-5-yl]-ethanone

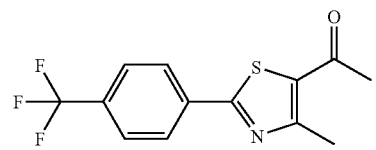

A mixture of 1-[4-Methyl-2-(4-trifluoromethyl-phenyl)-thiazol-5-yl]-ethanol (1.0 g, 3.48 mmol) and MnO2 (0.45 g, 5.22 mmol) in chloroform (30 mL) is heated to reflux, after 24 hrs, additional MnO2 (300 mg) is added and refluxed for another 9 hrs, the reaction mixture is filtered through celite. Concentration of filtrate yields the title compound (1.0 g).

Step B 5-(2-Methoxy-1-methyl-vinyl)-4-methyl-2-(4-trifluoromethyl-phenyl)-thiazole

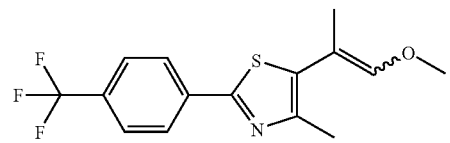

To a solution of (methoxymethyl)triphenyl phosphonium chloride (15.5 g, 45.2 mmole) in toluene (330 mL) is added potassium t-butoxide (5.07 g, 45.2 mmole) in one portion and stirred for 30 minutes, then a solution of 1-[4-Methyl-2-(4-trifluoromethyl-phenyl)-thiazol-5-yl]-ethanone (8.6 g, 30.1 mmole) in toluene (20 mL) is added. The reaction is stirred for 4 hours, quenched by NH4Cl aqueous solution, extracted with ethyl acetate and then concentrated on rota vapor. The residue is purified on a silica gel column, eluting with 0-10% ethyl acetate in hexane and concentrated to provide the title compound (7.0 g).

Step C

2-[4-Methyl-2-(4-trifluoromethyl-phenyl)-thiazol-5-yl]-propionaldehyde

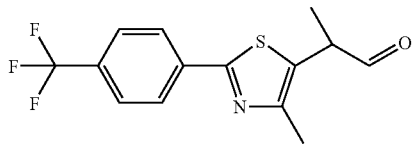

5-(2-Methoxy-1-methyl-vinyl)-4-methyl-2-(4-trifluoromethyl-phenyl)-thiazole (7.0 g, 22.3 mmol) in THF (200 mL) is treated with concentrated HCl aqueous solution (7 mL) at 50° C. for 2 hours. The reaction mixture is diluted with ethyl acetate, washed with sodium bicarbonate aqueous solution, dried over sodium sulfate. Concentration and column chromatography on silica gel provided the title compound (3.5 g).

Step D

2-[4-Methyl-2-(4-trifluoromethyl-phenyl)-thiazol-5-yl]-propan-1-ol

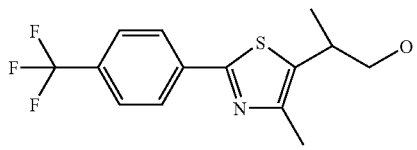

To a solution of 2-[4-methyl-2-(4-trifluoromethyl-phenyl)-thiazol-5-yl]-propionaldehyde (2.0 g, 6.68 mmol) in ethanol (30 mL) is added to NaBH4 (0.25 g, 6.6 mmol) in portions at 0° C. The reaction is kept at 0° C. for 15 minutes and warmed up to room temperature for 2 hours. The reaction is quenched using water, extracted with ethyl acetate, dried over sodium sulfate. Concentration and column chromatography on silica gel eluted with hexanes and ethyl acetate yields the title compound (2.0 g).

Preparation 122

2-[5-Ethyl-2-(4-trifluoromethyl-phenyl)-thiazol-4-yl]-propan-1-ol

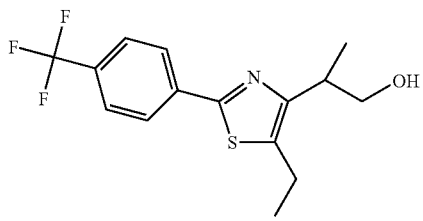

Step A

3-Oxo-hexanoic acid ethyl ester (29.5 g, 0.1865 Mol) is dissolved into anhydrous dichloromethane (DCM) (400 mL) and then cooled to 0° C.-5° C. while stirring. A solution of bromine (30.4 g, 0.190 Mol) in DCM (80 mL) is added dropwise over 2 h. to the solution of the beta keto-ester. After the addition, the mixture is allowed to stir 0.5 h. at 0° C., then the ice bath is removed and the mixture is allowed to stir at room temperature for 18 h. TLC will show complete consumption of starting material, then ice water (200 g) is added with stirring. The organic layer is collected and washed with cold water (2×) and brine. The filtered solution is dried over anhydrous sodium sulfate, then concentrated to a clear liquid. The crude 4-Bromo-3-oxo-hexanoic acid ethyl ester (40.2 g, 0.1695 Mol), 91% yield, is used without further purification.

Step B

4-Bromo-3-oxo-hexanoic acid ethyl ester (4.68 g, 20.98 mmol) is dissolved into denatured ethanol (100 mL) and para-trifluoromethyl thiobenzamide (4.31 g, 21 mmol) is added in one portion. The reaction is purged of air and flushed with nitrogen then heated to reflux. The reaction is monitored by TLC and HPLC and when complete, the reaction is allowed to cool to room temperature. The solvent is removed and the reaction is diluted with ethyl acetate (200 mL), followed by washes with saturated sodium bicarbonate solution, water, and brine. The ethyl acetate solution is dried over anhydrous sodium sulfate, then concentrated and further purified using flash column chromatography (10% EtOAc/Hexanes) to yield pure [5-Ethyl-2-(4-trifluoromethyl-phenyl)-thiazol-4-yl]-acetic acid ethyl ester (5.09 g, 14.82 mmol) or 71% yield.

Step C

[5-Ethyl-2-(4-trifluoromethyl-phenyl)-thiazol-4-yl]-acetic acid ethyl ester (2.02 g, 6.13 mmol) is dissolved into anhydrous tetrahydrofuran (THF) (10 mL) and lithium diisopropylamide (LDA) is slowly added at room temperature. This solution is allowed to stir at room temperature and monitored by TLC. After complete conversion, methyl iodide (582 mg, 4.00 mmol) is added slowly and the reaction is followed by TLC. After 18 h., the reaction is not complete, but is quenched with saturated ammonium chloride solution and diluted with diethyl ether. The two phases are separated and the organic layer is washed with water and brine, dried over anhydrous sodium sulfate, then concentrated and purified using flash column chromatography (10% EtOAc/Hexanes). The pure 2-[5-Ethyl-2-(4-trifluoromethyl-phenyl)-thiazol-4-yl]-propionic acid ethyl ester (1.30 g, 3.64 mmol) is obtained in 59% yield.

Step D

2-[5-Ethyl-2-(4-trifluoromethyl-phenyl)-thiazol-4-yl]-propionic acid ethyl ester (1.05 g, 3.06 mmol) is dissolved into anhydrous tetrahydrofuran (THF) (10 mL) and then cooled to 0° C. with stirring. Lithium aluminum hydride (3.10 mL, 1M in THF, 3.10 mmol) is slowly added by syringe and the reaction is monitored by TLC. Upon complete conversion, the reaction is carefully quenched using water, base, and water. Celite is added to the reaction, followed by diethyl ether and the mixture is then filtered through a celite plug. The two phases are then separated and the organic layer is washed using water and brine. The organic layer is the dried over anhydrous sodium sulfate and concentrated. The pure 2-[5-Ethyl-2-(4-trifluoromethyl-phenyl)-thiazol-4-yl]-propan-1-ol (0.930 g, 2.95 mmol) is obtained in 95% yield after flash column chromatography.

Preparation 123

2-[4-Isopropyl-2-(4-trifluoromethyl-phenyl)-thiazol-5-yl]-propan 1-ol

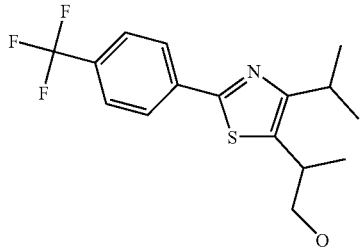

Step A

4-Isopropyl-2-(4-trifluoromethyl-phenyl)-thiazole-5-carboxylic acid methyl ester (14 g, 40.1 mmol) is dissolved into anhydrous tetrahydrofuran (THF) (200 mL) and then cooled to −30° C. while stirring under nitrogen. N-methyl, N-methoxy amine hydrochloride (0.881 g, 9.04 mmol) is then added to the solution in one portion. Isopropyl magnesium chloride (8.73 mL, 2M soln. in THF, 17.46 mmol) is slowly added to the cooled suspension over 1 h. TLC will show complete consumption of starting material, then 30% solution of ammonium chloride is added with stirring. The reaction is diluted with diethyl ether and extracted. The organic layer is collected and washed with cold water (2×) and brine. The solution is then dried over anhydrous sodium sulfate, filtered, and concentrated. The 4-Isopropyl-2-(4-trifluoromethyl-phenyl)-thiazole-5-carboxylic acid methoxy-methyl-amide (0.705 g, 1.97 mmol) is obtained in pure form after flash column chromatography.

Step B

4-Isopropyl-2-(4-trifluoromethyl-phenyl)-thiazole-5-carboxylic acid methoxy-methyl-amide (7.56 g, 21.09 mmol) is suspended in anhydrous tetrahydrofuran (100 mL), and cooled to 0° C. with stirring under nitrogen. Methyl magnesium bromide (28 mL, 3.0M in diethyl ether, 84.36 mmol) is slowly added to the reaction over 1 h. The reaction is allowed to warm slowly to room temperature and monitored by TLC. Upon complete consumption of starting material, the reaction is carefully neutralized with 1N hydrochloric acid, extracted with diethyl ether, washed, dried, and concentrated. The 1-[4-Isopropyl-2-(4-trifluoromethyl-phenyl)-thiazol-5-yl]-ethanone (5.4 g, 17.23 mmol) 82% yield, is used without further purification.

Step C (Methoxymethyl)triphenylphosphinium chloride (8.86 g, 25.84 mmol) is suspended in anhydrous toluene (75 mL) and potassium tert-butoxide (2.90 g, 25.84 mmol) is carefully added. The solution is allowed to cool and stir at room temperature for 1 h. 1-[4-Isopropyl-2-(4-trifluoromethyl-phenyl)-thiazol-5-yl]-ethanone (5.4 g, 17.23 mmol) is then dissolved into anhydrous toluene (25 mL) and added to the reaction mixture by syringe. The reaction is allowed to stir at room temperature for several hours and is monitored by TLC. Upon complete consumption of starting material, the reaction is carefully quenched with saturated ammonium chloride solution, extracted with diethyl ether, washed, dried, and concentrated. The 4-Isopropyl-5-(2-methoxy-1-methyl-vinyl)-2-(4-trifluoromethyl-phenyl)-thiazole is used in the next step without further purification.

Step D

4-Isopropyl-5-(2-methoxy-1-methyl-vinyl)-2-(4-trifluoromethyl-phenyl)-thiazole is dissolved into anhydrous tetrahydrofuran (100 mL) and concentrated hydrochloric acid (5 mL) is added with stirring under nitrogen. The reaction is heated to 50° C. and monitored by TLC. Upon complete consumption of starting material, the reaction is carefully neutralized with sodium hydroxide, extracted with diethyl ether, washed, dried, and concentrated. The 2-[4-Isopropyl-2-(4-trifluoromethyl-phenyl)-thiazol-5-yl]-propionaldehyde (4.6 g, 14.05 mmol), 82% two steps, is obtained in pure form after flash column chromatography.

Step E

2-[4-Isopropyl-2-(4-trifluoromethyl-phenyl)-thiazol-5-yl]-propionaldehyde (4.05 g, 12.5 mmol) is dissolved into denatured ethanol (60 mL) at room temperature then cooled to 0° C. in an ice bath. Sodium borohydride (0.467 g, 12.5 mmol) is then carefully added in small portions. The reaction is allowed to warm slowly to room temperature and is monitored by TLC. Upon complete consumption of starting material, the reaction is carefully quenched with water and diluted with ethyl acetate. The ethanol is removed and the residue is extracted with ethyl acetate, washed, dried, and concentrated. The 2-[4-Isopropyl-2-(4-trifluoromethyl-phenyl)-thiazol-5-yl]-propan-1-ol (4.0 g, 12.14 mmol), 97%, is obtained in pure form after flash column chromatography.

Preparation 124

Toluene-4-sulfonic acid 2-[5-ethyl-2-(4-trifluoromethyl-phenyl)-oxazol-4-yl]-ethyl ester

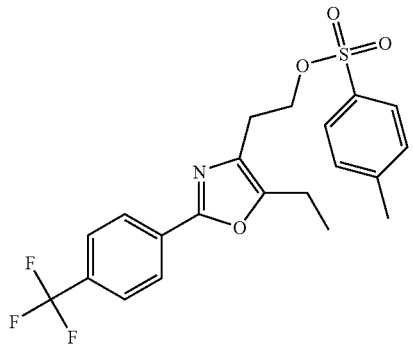

Step A

To a solution of α,α,α-trifluoromethyl-para-toluic acid (5.0 g, 26.3 mmol) in anhydrous acetone (100 mL) at 0° C. under nitrogen is added 4-bromo-3-oxo-hexanoic acid ethyl ester (6.4 g, 27 mmol) and triethyl amine (3.5 mL, 27 mmol). The mixture is allowed to stir 0.5 h. at 0° C., then the ice bath is removed and the mixture allowed to stir at room temperature for 18 h. The reaction is monitored by TLC and HPLC until complete consumption of starting material, then ice water added with stirring and the mixture is extracted. The organic layer is collected and washed with brine, then dried over anhydrous sodium sulfate. The crude 4-Trifluoromethylbenzoic acid 3-ethoxycarbonyl-1-ethyl-2-oxo-propyl ester is used in the next step without further purification.

Step B

4-Trifluoromethyl-benzoic acid 3-ethoxycarbonyl-1-ethyl-2-oxo-propyl ester (25 mmol) is dissolved in acetic acid (100 mL) and dry ammonium acetate (10 g, 100 mmol) is added, then the reaction is heated under nitrogen to reflux. The reaction is monitored by TLC and HPLC but complete consumption of the starting material is never observed, and then allowed to cool. The cooled reaction is concentrated and diluted with 250 mL ethyl acetate. The residue is washed with 100 mL saturated sodium bicarbonate followed by water and brine. The organic layer is dried over anhydrous sodium sulfate, then concentrated and purified by column chromatrography. The fractions that contained pure product are concentrated to yield [5-Ethyl-2-(4-trifluoromethyl-phenyl)-oxazol-4-yl]-acetic acid ethyl ester (4.0 g, 12.22 mmol) or 50% yield.

Step C

[5-Ethyl-2-(4-trifluoromethyl-phenyl)-oxazol-4-yl]-acetic acid ethyl ester (4.0 g, 12.22 mmol) in anhydrous tetrahydrofuran (100 mL) is cooled to 0° C. and a 1M LiAlH$_4$ (12.2 mL, 12.2 mmol) solution is added slowly. The reaction is monitored by TLC until complete consumption of the starting material. The reaction is then carefully quenched with 2.4 mL water, 2.4 mL 5N NaOH and 7 mL water. The light tan solid is filter through celite and dried to give crude 2-[5-Ethyl-2-(4-trifluoromethyl-phenyl)-oxazol-4-yl]-ethanol (2.74 g, 9.60 mmol) or 79% yield.

Step D

To a solution of 2-[5-Ethyl-2-(4-trifluoromethyl-phenyl)-oxazol-4-yl]-ethanol 2.74 g, 9.60 mmol) in anhydrous dichloromethane (50 mL) is added dimethylamino pyridine (0.500 g, 4.00 mmol), tosic anhydride (8.4 g, 24 mmol), and pyridine (3.4 mL, 42 mmol) at room temperature. The reaction is monitored by TLC, and upon complete consumption of the starting alcohol, the reaction is diluted with DCM and extracted against saturated sodium bicarbonate solution. The organic layer is washed with water and brine, then dried over anhydrous sodium sulfate and concentrated. The pure toluene-4-sulfonic acid 2-[5-ethyl-2-(4-trifluoromethyl-phenyl)-oxazol-4-yl]-ethyl ester (3.0 g, 6.82 mmol) is obtained after flash column chromatography.

Preparation 125

Toluene-4-sulfonic acid 2-methyl-2-[5-methyl-2-(4-trifluoromethyl-phenyl)-thiazol-4-yl]-propyl ester

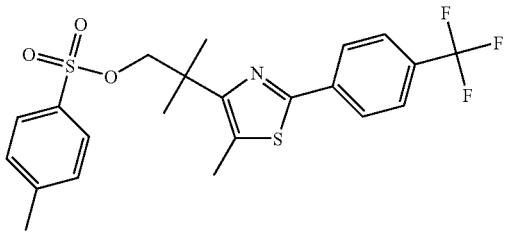

Preparation 126

Toluene-4-sulfonic acid 2-methyl-2-[5-methyl-2-(4-trifluoromethyl-phenyl)-oxazol-4-yl]-propyl ester

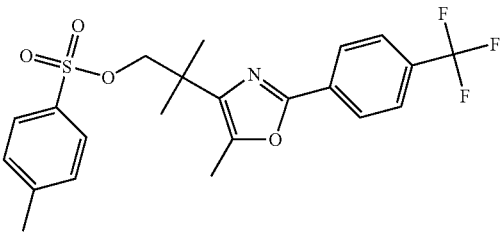

Preparation 127

1-[5-Ethyl-2-(4-trifluoromethyl-phenyl)-thiazol-4-yl]-propan-2-ol

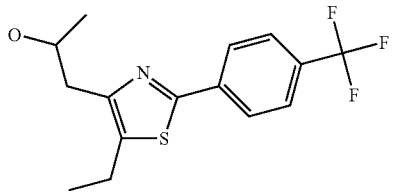

Step A

To a solution of 2-[5-Ethyl-2-(4-trifluoromethyl-phenyl)-thiazol-4-yl]-ethanol (1.25 g, 4.16 mmol) in anhydrous dichloromethane (25 mL) at 0° C. under nitrogen is slowly added Dess-Martin periodinane (2.6 g, 6.24 mmol). The reaction is allowed to warm slowly to room temperature and monitored by TLC. After complete consumption of the starting material, the reaction is diluted with dichloromethane and the two phases are separated. The organic layer is washed, dried, filtered and concentrated. The crude [5-Ethyl-2-(4-trifluoromethyl-phenyl)-thiazol-4-yl]-acetaldehyde (0.253 g, 0.840 mmol), 21% yield, is further purified using flash column chromatography.

Step B

[5-Ethyl-2-(4-trifluoromethyl-phenyl)-thiazol-4-yl]-acetaldehyde (0.253 g, 0.840 mmol), is dissolved in anhydrous tetrahydrofuran (5 mL) and cooled to 0° C. with stirring under nitrogen. Methylmagnesium bromide, 3.0M in ether, (0.300 mL, 1.00 mmol) is added and the ice bath removed. After slowly warming to room temperature, the reaction is monitored by TLC. After the starting material is completely consumed, the reaction is quenched with saturated ammonium chloride solution and diluted with ether. The two phases are separated and the organic washed with water and brine, dried over sodium sulfate, then concentrated. The residue is further purified using flash column chromatography. The 1-[5-Ethyl-2-(4-trifluoromethyl-phenyl)-thiazol-4-yl]-propan-2-ol (0.222 g, 0.7049 mmol) is formed in 70% yield.

Preparation 128

C-[5-Methyl-2-(4-trifluoromethyl-phenyl)-oxazol-4-yl]-methylamine

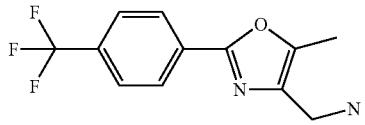

Step A

4-Azidomethyl-5-methyl-2-(4-trifluoromethyl-phenyl)-oxazole

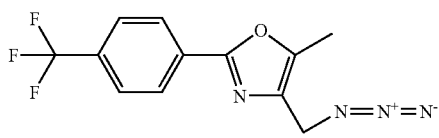

To a solution of 4-chloromethyl-5-methyl-2-(4-trifluoromethyl-phenyl)-oxazole (2.4 g, 8.71 mmol) in methanol (13 mL) is added sodium azide (1.13 g, 17.4 mmol) in water (10 mL). The mixture is heated to reflux for 3 hrs, cooled to room temperature, majority of the methanol is evaporated, the residue is extracted with ethyl acetate, dried, concentrated and column chromatography on silica gel yields the title compound (2.10 g).

Step B

C-[5-Methyl-2-(4-trifluoromethyl-phenyl)-oxazol-4-yl]-methylamine

A mixture of 4-azidomethyl-5-methyl-2-(4-trifluoromethyl-phenyl)-oxazole (1.70 g) and PtO2 (0.106 g) in ethyl acetate (50 mL) at room temperature under 60 psi of hydrogen for 5 hrs, the reaction mixture is filtered through celite and filtrate is concentrated giving the title compound (1.3 g, 84.2% yield).

Preparation 129

2R-[5-Methyl-2-(4-trifluoromethyl-phenyl)-thiazol-4-yl]-propan-1-ol

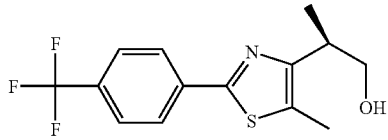

The racemic alcohol 2-[5-methyl-2-(4-trifluoromethyl-phenyl)-thiazol-4-yl]-propan-1-ol is resolved on a Chiralpak AD column (4.6×250 mm). Eluted with ethanol in heptane and concentrated the fractions to provide pure enantiomers.

Preparation 130

2S-[5-Methyl-2-(4-trifluoromethyl-phenyl)-oxazol-4-yl]-propan-1-ol

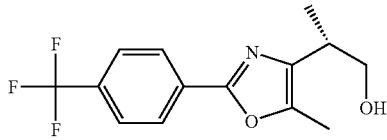

This compound is obtained in 129.

Preparation 131

(5-Hydroxy-indol-1-yl)-acetic acid ethyl ester

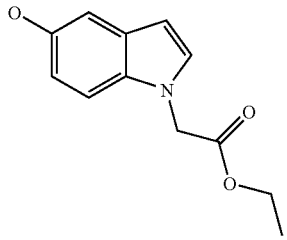

Step A 5-benzyloxyindole (10.0 g, 44.79 mmol) is dissolved into anhydrous DMF (100 mL) and cooled to 0° C. in an ice water bath. Sodium hydride (2.6 g, 67.18 mmol) is dissolved into anhydrous DMF (100 mL), then slowly added to the indole solution using an addition funnel. The reaction is allowed to stir at 0° C. for 1 h., then the ice bath is removed and the solution is allowed to warm slowly to room temperature. The solution is then cooled back down to 0° C. and ethyl bromoacetate (11.2 g, 67.18 mmol) is then added in one portion. The reaction is allowed to stir at 0° C. for 1 h., then the ice bath is removed and the solution is allowed to warm slowly to room temperature. Upon completion, the reaction is quenched carefully using water, then diluted with EtOAc (300 mL). Brine (100 mL) is added and the two layers are separated in a separatory funnel. The organic layer is rinsed with water (2×75 mL) and then dried over anhydrous magnesium sulfate. The organic layer is then concentrated and purified using flash column chromatography (5% EtOAc/Hexanes) to yield 11.86 g (86%) of (5-Benzyloxy-indol-1-yl)-acetic acid ethyl ester.

Step B (5-Benzyloxy-indol-1-yl)-acetic acid ethyl ester (3.49 g, 11.31 mmol) is dissolved in EtOH (50 mL) and glacial acetic acid is added (2.0 mL). Palladium on carbon (20% by wt., 0.700 g) is then added to the homogenous solution, and a hydrogen filled balloon is connected to the round bottom flask. A vacuum is created within the flask until the ethanol began to bubble, and the hydrogen allowed to enter the flask; this procedure is repeated three times, then the reaction is left to stir at room temperature overnight. Upon completion, the reaction is diluted with DCM (200 mL), and water (100 mL) is added. The mixture is filtered through a celite plug and the two phases are separated. The organic layer is washed with brine (2×75 mL), then dried over anhydrous magnesium sulfate, and concentrated to yield the title compound (2.42 g) in 98% yield. The residual acetic acid is removed by flash column chromatography. $^1$H NMR (DMSO-$d_6$, 400 MHz): δ 1.18 (t, J=7.34 Hz, 3H), 4.12 (q, J=6.85 Hz, 2H), 4.99 (s, 2H), 5.73 (s, 1H), 6.23 (d, J=2.94 Hz, 1H), 6.60 (dd, $J_1$=1.96 Hz, $J_2$=8.80 Hz, 1H), 6.84 (d, J=2.45 Hz, 1H), 7.12 (d, J=8.80 Hz, 1H), 7.19 (d, J=2.94 Hz, 2H); MS (ES, m/z):$C_{12}H_{13}NO_3$: 220.21(M$^+$+1), 218.7(M$^+$−1).

The following compounds are prepared in a manner substantially similar to that used to prepare the compound of preparation 21.

Preparation 132

3-(5-Hydroxy-indol-1-yl)-propionic acid ethyl ester

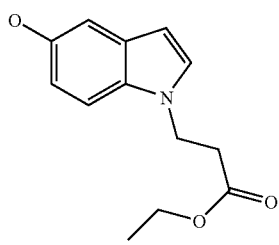

Preparation 133

4-(5-Hydroxy-indol-1-yl)-butyric acid ethyl ester

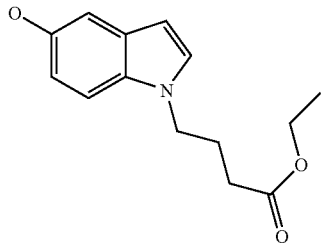

Preparation 134

S-(5-Hydroxy-indol-1-yl)-pentanoic acid ethyl ester

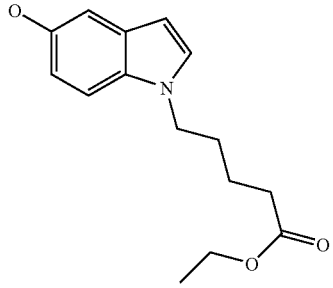

Preparation 135

2-(5-Hydroxy-indol-1-yl)-propionic acid ethyl ester

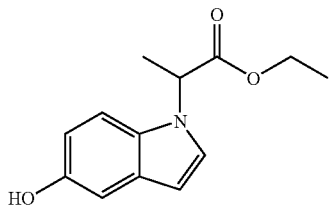

Step A 2-(5-Benzyloxy-indol-1-yl)-propionic acid ethyl ester

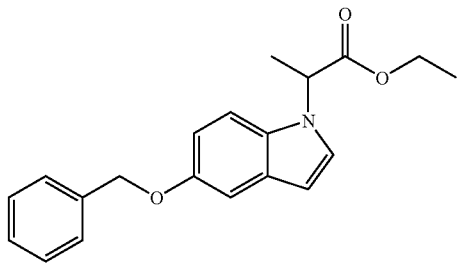

To a mixture of NaH (60%, 4.92 g, 0.205 mol) in DMF (60 mL) is added 5-benzoxyindole at 0~5° C., then stirred 30 min. ethyl 2-bromopropionate is added dropwise, the mixture is allowed to warm to room temperature and heated at 70° C. overnight, cooled to room temperature, diluted with ethyl acetate, washed with water and brine, dried over sodium sulfate. Concentration and column chromatography on silica gel eluted with hexanes and ethyl acetate yields the title compound (29 g).

Step B 2-(5-Hydroxy-indol-1-yl)-propionic acid ethyl ester

A mixture of 2-(5-Benzyloxy-indol-1-yl)-propionic acid ethyl ester (16 g) and Pd/C (5%, 1.93 g) in ethanol (190 mL) is stirred under 60 PSI of hydrogen overnight. Filtration and concentration yields the title compound.

Preparation 136

2-(5-Hydroxy-indol-1-yl)-2-methyl-propionic acid ethyl ester

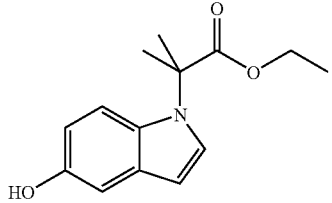

Step A

2-(5-Benzyloxy-indol-1-yl)-2-methyl-propionic acid ethyl ester

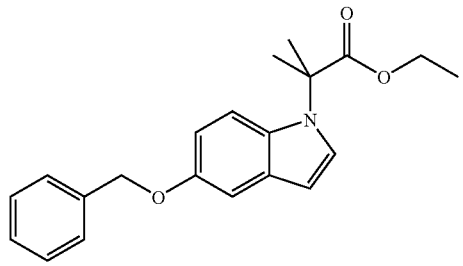

To a solution of 2-(5-benzyloxy-indol-1-yl)-propionic acid ethyl ester (20 g, 61.5 mmol) in THF (180 mL) is added LDA (2.0 M toluene, 37 mL) dropwise at −78° C. After the addition of LDA, the mixture is stirred for 30 min, then methyl iodide (8.77 g, 122.6 mmol) is added. The reaction mixture is allowed to warm to room temperature, after stirred for 2 hrs, quenched by water, extracted with ethyl acetate, dried over sodium sulfate. Concentration yields the title compound.

Step B

2-(5-Hydroxy-indol-1-yl)-2-methyl-propionic acid ethyl ester

A mixture of 2-(5-benzyloxy-indol-1-yl)-2-methyl-propionic acid ethyl ester (15.6 g) and Pd/C (5%, 1.93 g) in ethanol (190 mL) is stirred under 60 PSI of hydrogen overnight. Filtration and concentration yields the title compound (11 g).

Preparation 137

(5-Hydroxy-2-methyl-indol-1-yl)-acetic acid ethyl ester

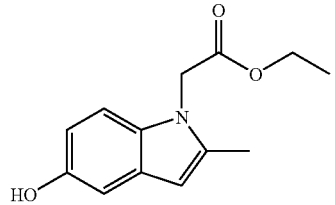

Step A

(5-Methoxy-2-methyl-indol-1-yl)-acetic acid ethyl ester

To a solution of 2-methyl-5-methoxyindole (5.10 g, 31.6 mmol) in DMF (200 mL) is added sodium hydride (60%, 1.9 g, 47.4 mmol) at 0~5° C., stirred for 30 min, ethyl 2-bromoacetate (8.35 g, 50 mmol) is added. After 2 hr at room temperature, the reaction is quenched by water, extracted with ether. Combined organic layers are washed with water and brine, dried over sodium sulfate. Concentration yields the crude title product, which is used for next step without further purification.

Step B

(5-hydroxy-2-methyl-indol-1-yl)-acetic acid ethyl ester

To a solution of (5-methoxy-2-methyl-indol-1-yl)-acetic acid ethyl ester (0.87 g, 3.51 mmol) in methylene chloride (25 mL) is added BBr3 (1.0 mL, 10.5 mmol) at −20° C. After stirred at −20° C. for 2 hrs, the reaction mixture is poured into ice, extracted with methylene chloride, dried over sodium sulfate. Concentration yields the crude title compound, which is used for next step without further purification.

Preparation 138

{5-[3-(Toluene-4-sulfonyloxy)-propoxy]-indol-1-yl}-acetic acid ethyl ester

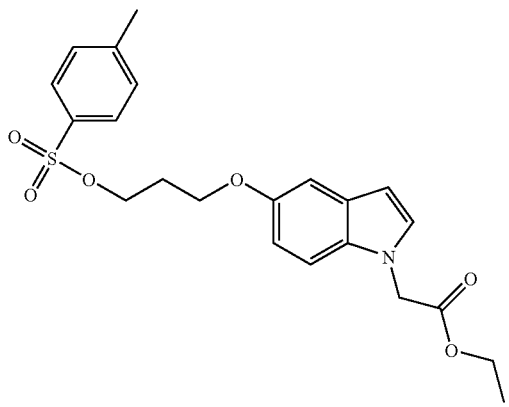

[5-(3-Hydroxy-propoxy)-indol-1-yl]-acetic acid ethyl ester (2.0 g, 6.55 mmol) is dissolved into anhydrous dichlormethane (DCM) (35 mL), then dimethylamino pyridine (300 mg, 1.965 mmol), tosic anhydride (4.3 g, 13.1 mmol), and pyridine (2.3 mL, 23 mmol) are added. The reaction allowed to stir at room temperature under nitrogen. Upon completion, the reaction is then diluted with DCM (100 mL) and saturated sodium bicarbonate solution (50 mL) is added and the two layers are separated in a separatory funnel. The organic layer is rinsed with water (2×75 mL) and brine (2×50 mL), then dried over anhydrous magnesium sulfate. The organic layer is then concentrated and purified using flash column chromatography (5% EtOAc/Hexanes) to yield 1.92 g (64%) of the title compound.

The following compounds are prepared in a similar manner:

Preparation 139

2-Methyl-2-{5-[3-(toluene-4-sulfonyloxy)-propoxy]-indol-1-yl}-propionic acid ethyl ester

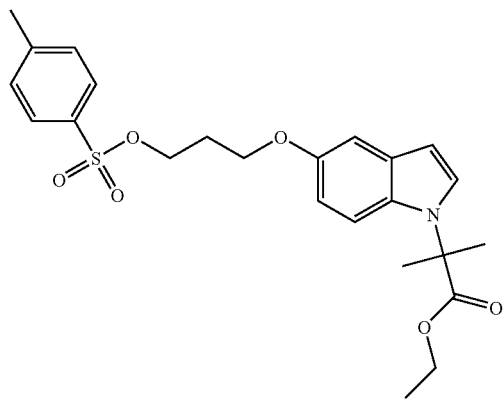

Preparation 140

{5-[2-(Toluene-4-sulfonyloxy)-ethoxy]-indol-1-yl}-acetic acid ethyl ester

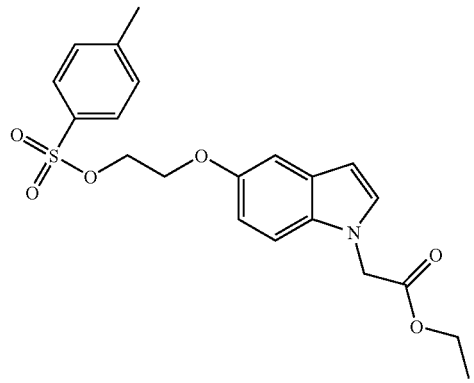

Preparation 141

(5-Mercapto-indol-1-yl)-acetic acid ethyl ester

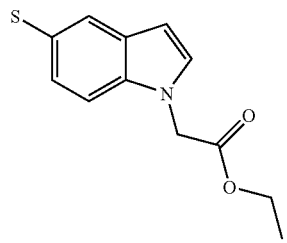

Step A (5-Bromo-indol-1-yl)-acetic acid ethyl ester (2.0 g, 7.09 mmol) is dissolved into anhydrous tetrahydrofuran (THF) (10 mL) and the reaction vessel purged with nitrogen a few times. Tetrakis triphenylphosphine palladium (175 mg, 0.15 mmol) is then added to the indole solution in one portion, purge again. Meanwhile, triisopropylsilylthiol (1.67 mL, 7.8 mmol) is dissolved in anhydrous TBF (20 mL) and potassium hydride (0.483 mg, 7.8 mmol) is then slowly added. This mixture is heated to 50° C. for 4 h. After this solution has cooled to room temperature, it is transferred to the indole solution via cannula. This solution is the heated to 70° C. until the reaction is complete. Upon completion, the reaction is quenched carefully using water, then diluted with EtOAc (300 mL). Brine (100 mL) is added and the two layers are separated in a separatory funnel. The organic layer is rinsed with water (2×75 mL) and then dried over anhydrous magnesium sulfate. The organic layer is then concentrated and purified using flash column chromatography (5% EtOAc/Hexanes) to yield 1.3 g (50%) of (5-Triisopropylsilanylsulfanyl-indol-1-yl)-acetic acid ethyl ester.

Step B (5-Triisopropylsilanylsulfanyl-indol-1-yl)-acetic acid ethyl ester (60 mg, 0.1621 mmol) is dissolved in n-methylpyrrolidinone (NMP) (5 mL) and cesium fluoride (0.243 mmol) is added. The reaction is allowed to stir at room temperature until complete. This solution may be used in the coupling step (next) without further purification.

Preparation 142

(6-Hydroxy-1H-indol-3-yl)-acetic acid methyl ester

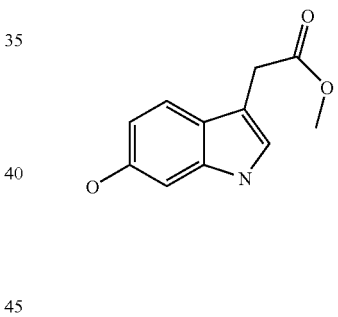

Step A (6-Benzyloxy-1H-indol-3-yl)-oxo-acetic acid methyl ester

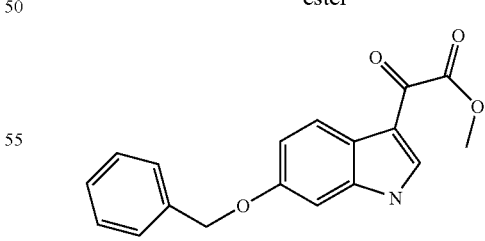

To a solution of 6-benzoxyindole (1.05 g, 4.7 mmol) in ether (8 mL) is added oxalyl chloride (0.45 mL) at 0~5° C., stirred for 2 hrs. The reaction mixture is cooled to −78° C., sodium methoxide (25% w/w in methanol, 2.4 mL) is added, warmed up to room temperature, quenched by water. Solid product is collected by filtration, washed by water and dried under vacuum.

Step B

(6-Hydroxy-1H-indol-3-yl)-acetic acid methyl ester

Preparation 146

(1-Ethyl-6-hydroxy-1H-indol-3-yl)-acetic acid ethyl ester

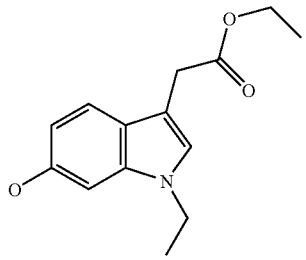

Step A

To a solution of (6-Benzyloxy-1H-indol-3-yl)-oxo-acetic acid ethyl ester (3.0 g, 9.7 mmol) in anhydrous dimethyl formamide (50 mL) at 0° C. under nitrogen is added sodium hydride (0.600 g, 14.5 mmol) in small portions. The reaction is allowed to warm to room temperature slowly and monitored by TLC. Upon complete conversion, the reaction is cooled back down to 0° C. and ethyl bromide (1.5 mL, 20 mmol) is slowly added to the slurry. The reaction is allowed to warm slowly to room temperature and monitored by TLC. After complete consumption of the starting material, the reaction is quenched with water, then diluted with ethyl acetate, and the two phases are separated. The organic layer is washed, dried, filtered and concentrated. The crude (6-Benzyloxy-1-ethyl-1H-indol-3-yl)-oxo-acetic acid ethyl ester (0.843 g, 2.40 mmol), 25% yield, is further purified using flash column chromatography.

Step B (6-Benzyloxy-1-ethyl-1H-indol-3-yl)-oxo-acetic acid ethyl ester (0.843 g, 2.40 mmol) is dissolved in anhydrous dioxane (10 mL) then purged and back filled with nitrogen a few times. Palladium on carbon (10%) (0.200 g, 20% by wt.) is added and the reaction followed by heating to reflux. Slow addition of a saturated solution of sodium hypophosphite is initiated and the reaction is monitored by TLC. After the starting material is completely consumed, the reaction is allowed to cool to room temperature, diluted with dichloromethane and celite added. The mixture is filtered through a plug of celite and the two phases are separated. The organic layer is washed with water and brine, dried over sodium sulfate, then concentrated. The residue is further purified using flash column chromatography. The (1-Ethyl-6-hydroxy-1H-indol-3-yl)-acetic acid ethyl ester (0.564 g, 2.28 mmol) is formed in 95% yield.

The following compound is made in a similar manner:

Preparation 147

(1-propyl-6-hydroxy-1H-indol-3-yl)-acetic acid ethyl ester

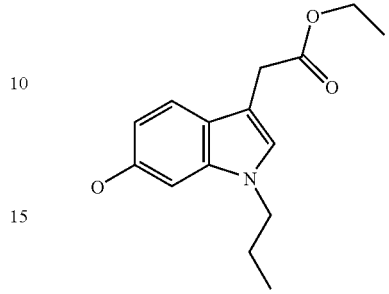

Preparation 148

(6-Hydroxy-benzo[b]thiophen-3-yl)-acetic acid ethyl ester

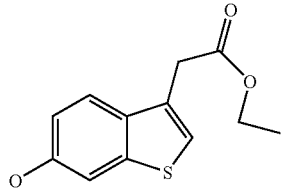

Step A 4-(3-Methoxy-phenylsulfanyl)-3-oxo-butyric acid ethyl ester

Ethyl 4-chloroacetoacetate (32.6 g, 0.188 mol), 3-methoxythiophenol (25.1 g, 0.179 mol) and DMF (700 mL) are combined and degassed by bubbling nitrogen through the stirred mixture for about 10 min, then potassium carbonate (50 g, 0.36 mol) is added to the stirred mixture in one batch. This mixture is stirred under nitrogen at room temperature for 2 h, the mixture is filtered to remove potassium carbonate, then diluted with ethyl acetate. The resulting solution is washed with water, then 5% aq. NaCl. The combined organics are washed with brine, dried over $Na_2SO_4$. Concentration yields the title compound as yellow liquid. This material is used without purification.

Step B (6-Methoxy-benzo[b]thiophen-3-yl)-acetic acid ethyl ester 4-(3-Methoxy-phenylsulfanyl)-3-oxo-butyric acid ethyl ester (10.0 g) is added to pre-cooled methanesulfonic acid (60 mL) at 0~5° C., then the reaction mixture is allowed to warm to room temperature. After 1 h, the mixture is diluted with ice water and extracted with ethyl acetate. The combined organics are washed with brine, dried over $Na_2SO_4$, A mixture of (6-benzyloxy-1H-indol-3-yl)-oxo-acetic acid methyl ester (1.45 g, 4.7 mmol) and Pd/C (10%, 0.9 g) in dioxane (38 mL) is degassed and filled with nitrogen for three times, then a solution of NaH2PO2 (6 g) in water (5 mL) is added dropwise at 100° C. The reaction mixture is heated overnight, filtered through celite and concentrated. The residue is taken into ethyl acetate, washed with water and brine, dried over sodium sulfate. Concentration and column chromatography on silica gel yields the title compound (600 mg).

The following compounds is made in a similar manner:

Preparation 143

(6-Hydroxy-1-methyl-1H-indol-3-yl)-acetic acid methyl ester

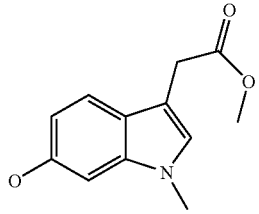

Preparation 144

(5-Hydroxy-1H-indol-3-yl)-acetic acid methyl ester

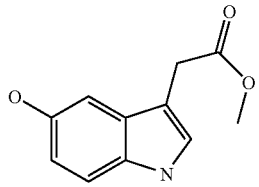

Preparation 145

(5-Hydroxy-1-methyl-1H-indol-3-yl)-acetic acid methyl ester

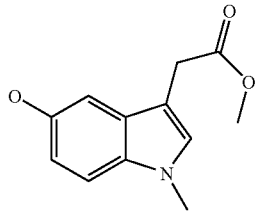

concentrated. Chromatography on silica gel elited with hexanes and ethyl acetate yields (6-methoxy-benzo[b]thiophen-3-yl)-acetic acid ethyl ester (4.8 g) and (4-methoxy-benzo[b]thiophen-3-yl)-acetic acid ethyl ester (0.8 g)

Step C (6-hydroxy-benzo[b]thiophen-3-yl)-acetic acid ethyl ester

To a solution of (6-Methoxy-benzo[b]thiophen-3-yl)-acetic acid ethyl ester (2.4 g, 9.6 mmol) in methylene chloride (60 mL) is added BBr3 (1.0 M, heptane, 29.4 mL, 29.4 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (2.2 g).

Preparation 149

(4-Hydroxy-benzo[b]thiophen-3-yl)-acetic acid ethyl ester

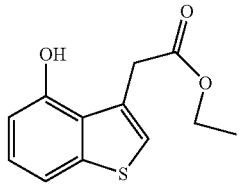

To a solution of (4-Methoxy-benzo[b]thiophen-3-yl)-acetic acid ethyl ester (0.7 g, 2.8 mmol) in methylene chloride (18 mL) is added BBr3 (1.0 M, heptane, 8.6 mL, 8.6 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (0.4 g).

Preparation 150

(6-Hydroxy-benzofuran-3-yl)-acetic acid methyl ester

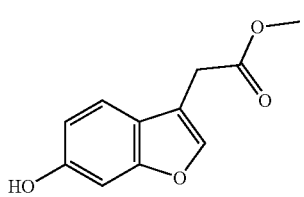

A mixture of 6-hydroxy-(2H)-benzofuran-3-one (5.0 g, 33.3 mmol), methyl (triphenylphosphoranylidene)acetate (25.0 g, 73 mmol), and xylenes (100 mL) is refluxed 6 hr. The reaction is concentrated and diluted with enough 1M aqueous hydrochloric acid to adjust pH to 2-3. The product is extracted into ethyl acetate (3×100 mL). The combined extracts are dried over anhydrous magnesium sulfate, filtered and concentrated. The residue is purified via silica chromatography eluting with 7:3 hexanes:ethyl acetate to afford the product as a orange oil, 1.3 g, 20%. MS M$^+$+1 207. The structure is confirmed by $^1$H NMR spectroscopy.

The following compound is made in a similar manner:

Preparation 151

2-(6-Hydroxy-benzofuran-3-yl)-propionic acid methyl ester

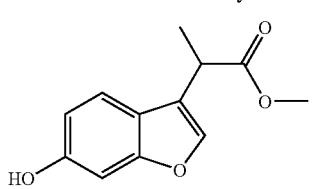

An orange oil. MS M$^+$+1 221. The structure is confirmed by $^1$H NMR spectroscopy.

Preparation 152

(5-Hydroxy-indol-1-yl)-acetic acid ethyl ester

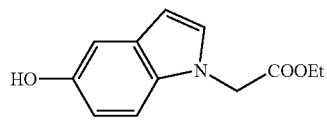

EXAMPLE 1

{6-[4-Isopropyl-2-(4-trifluoromethyl-phenyl)-thiazol-5-ylmethoxy]-benzo[b]thiophen-3-yl}-acetic acid

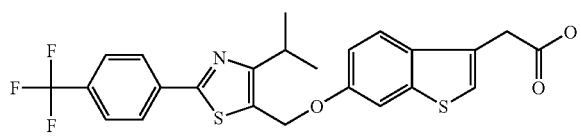

To a solution of 5-chloromethyl-4-isopropyl-2-(4-trifluoromethyl-phenyl)-thiazole (100 mg, 0.31 mmol) and (6-Hydroxy-benzo[b]thiophen-3-yl)-acetic acid ethyl ester (75 mg, 0.31 mmol) in acetonitrile (3 mL) is added Cs2CO3 (200 mg, 0.62 mmol). The mixture is stirred at room temperature overnight, ethanol (1 mL) is added, followed by NaOH (5 N, 1.0 mL). The mixture is heated at 50° C. for 2 hrs, solvent is evaporate, the residue is diluted with water, acidified by 5N HCl and extracted with ethyl acetate. Concentration and reversed phase HPLC purification yields the title product. MS (ES): 490.0 (M$^+$−1).

The following compound is made in a similar manner, all structures are confirmed by MS and proton NMR:

EXAMPLE 2

{6-[5-Methyl-2-(4-trifluoromethyl-phenyl)-oxazol-4-ylmethoxy]-benzo[b]thiophen-3-yl}-acetic acid

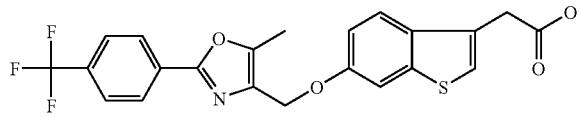

MS (ES): 446.0 (M$^+$−1).

EXAMPLE 3

{4-[4-Isopropyl-2-(4-trifluoromethyl-phenyl)-thiazol-5-ylmethoxy]-benzo[b]thiophen-3-yl}-acetic acid

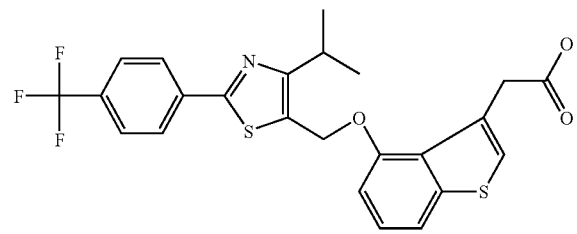

MS (ES): 492.0(M$^+$+1).

EXAMPLE 4

{4-[5-Methyl-2-(4-trifluoromethyl-phenyl)-oxazol-4-ylmethoxy]-benzo[b]thiophen-3-yl}-acetic acid

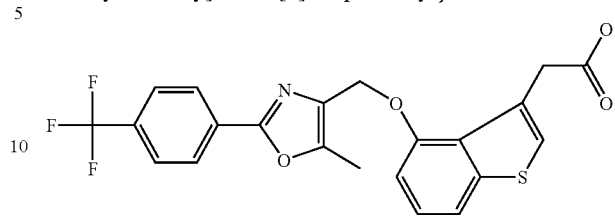

MS (ES): 448.2(M$^+$+1).

EXAMPLE 5

(6-{2-[5-Methyl-2-(4-trifluoromethyl-phenyl)-thiazol-4-yl]-propoxy}-benzo[b]thiophen-3-yl)-acetic acid

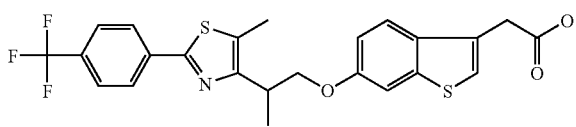

Step A (6-{2-[5-Methyl-2-(4-trifluoromethyl-phenyl)-thiazol-4-yl]-propoxy}-benzo[b]thiophen-3-yl)-acetic acid ethyl ester A solution of 2-[5-methyl-2-(4-trifluoromethyl-phenyl)-thiazol-4-yl]-propan-1-ol (226 mg, 0.75 mmol) in toluene (4.0 mL) is degassed and filled with nitrogen for 3 times. O this solution is added 1,1'-(azodicarbonyl)-dipiperidine (190 mg, 0.75 and mmol) and tributylphosphine (0.186 mL, 0.75 mmol) under nitrogen at 0° C., followed by addition of (6-hydroxy-benzo[b]thiophen-3-yl)-acetic acid ethyl ester (120 mg, 0.5 mmol). The reaction mixture is allowed to warm to room temperature and stirred overnight, the mixture is loaded on silica gel column. Chromatography yields the title compound (250 mg).

Step B (6-{2-[5-Methyl-2-(4-trifluoromethyl-phenyl)-thiazol-4-yl]-propoxy}-benzo[b]thiophen-3-yl)-acetic acid (6-{2-[5-Methyl-2-(4-trifluoromethyl-phenyl)-thiazol-4-yl]-propoxy}-benzo[b]thiophen-3-yl)-acetic acid ethyl ester (100 mg) is taken into ethanol (1 mL) and treated with NaOH (5.0 N, 1 mL) at 50° C. for 2 hrs. The reaction mixture is acidified with 5 N HCl, extracted with ethyl ether, dried over sodium sulfate. Concentration yields the title compound. MS (ES): 492.1(M$^+$+1), the structure is also confirmed by proton NMR.

The following compounds are made in a similar manner:

EXAMPLE 6

(6-{1-[4-Isopropyl-2-(4-trifluoromethyl-phenyl)-thiazol-5-yl]-ethoxy}-benzo[b]thiophen-3-yl)-acetic acid

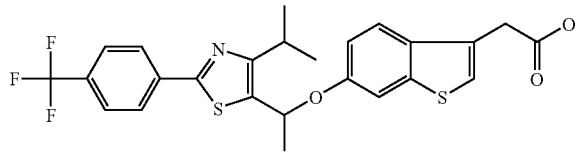

MS (ES): 506.1(M$^+$+1), the structure is also confirmed by proton NMR.

EXAMPLE 7

(6-{2-[5-Methyl-2-(4-trifluoromethyl-phenyl)-oxazol-4-yl]-ethoxy}-benzo[b]thiophen-3-yl)-acetic acid

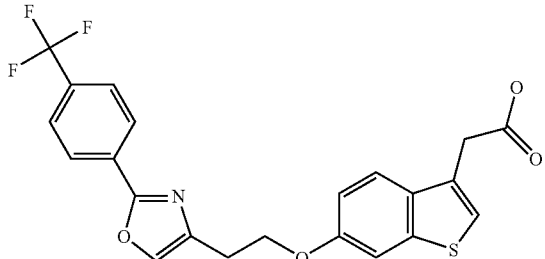

MS (ES): 462.09(M$^+$+1).

EXAMPLE 8

(6-{2-[5-Methyl-2-(4-trifluoromethyl-phenyl)-oxazol-4-yl]-propoxy}-benzo[b]thiophen-3-yl)-acetic acid

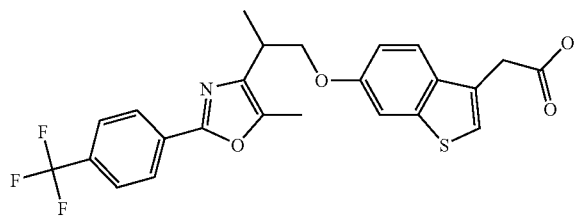

MS (ES): 476.1(M$^+$+1).

EXAMPLE 9

(6-{2-[4-Isopropyl-2-(4-trifluoromethyl-phenyl)-thiazol-5-yl]-propoxy}-benzo[b]thiophen-3-yl)-acetic acid

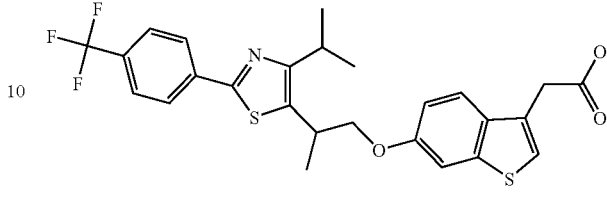

MS (ES): 520.07(M$^+$+1).

EXAMPLE 10

(R)-(6-{2-[4-Isopropyl-2-(4-trifluoromethyl-phenyl)-thiazol-5-yl]-propoxy}-benzo[b]thiophen-3-yl)-acetic acid

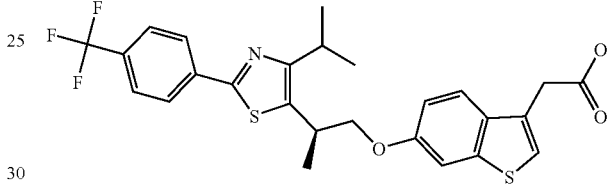

MS (ES): 520.03(M$^+$+1).

EXAMPLE 11

(S)-(6-{2-[4-Isopropyl-2-(4-trifluoromethyl-phenyl)-thiazol-5-yl]-propoxy}-benzo[b]thiophen-3-yl)-acetic acid

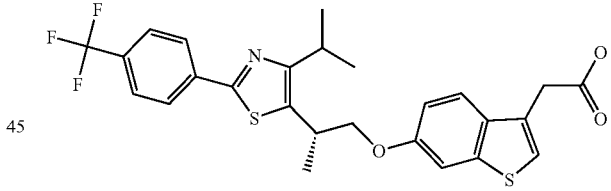

MS (ES): 520.03(M$^+$+1).

EXAMPLE 12

(R)-(4-{2-[5-Methyl-2-(4-trifluoromethyl-phenyl)-thiazol-4-yl]-propoxy}-benzo[b]thiophen-3-yl)-acetic acid

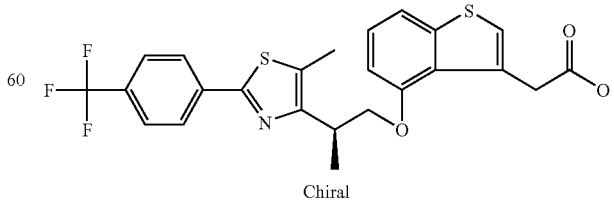

MS (ES):492.2(M$^+$+1).

EXAMPLE 13

(S)-(4-{2-[5-Methyl-2-(4-trifluoromethyl-phenyl)-thiazol-4-yl]-propoxy}-benzo[b]thiophen-3-yl)-acetic acid

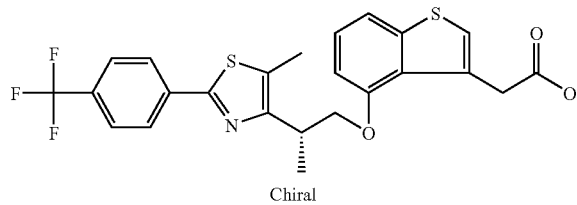

Chiral

MS (ES):492.2(M$^+$+1).

EXAMPLE 14

(4-{2-[5-Methyl-2-(4-trifluoromethyl-phenyl)-thiazol-4-yl]-ethoxy}-benzo[b]thiophen-3-yl)-acetic acid

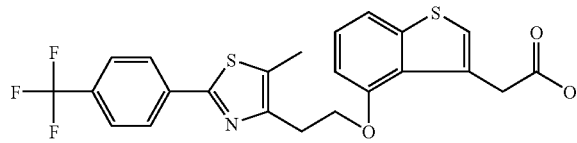

EXAMPLE 15

Racemic-(4-{1-[4-Isopropyl-2-(4-trifluoromethyl-phenyl)-thiazol-5-yl]-ethoxy}-benzo[b]thiophen-3-yl)-acetic acid

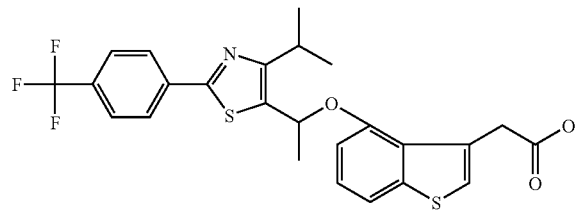

MS (ES):506.2(M$^+$+1).

EXAMPLE 16

3-{1-[4-Methyl-2-(4-trifluoromethyl-phenyl)-oxazol-5-yl]-ethoxy}-pyrido[1,2-a]indole-10-carboxylic acid

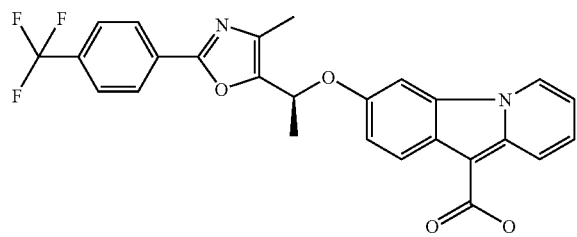

MS (ES): 481 (M$^+$+1). The structure is confirmed by $^1$H NMR spectroscopy.

EXAMPLE 17

5-{2-[4-Isopropyl-2-(4-trifluoromethyl-phenyl)-oxazol-5-yl]-propoxy}-1-methyl-1H-indole-2-carboxylic acid

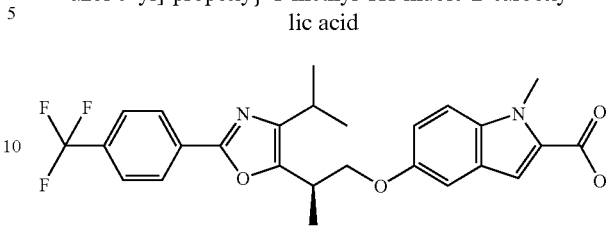

Step A

5-{2-[4-Isopropyl-2-(4-trifluoromethyl-phenyl)-oxazol-5-yl]-propoxy}-1-methyl-1H-indole-2-carboxylic acid ethyl ester 5-{2-[4-Isopropyl-2-(4-trifluoromethyl-phenyl)-oxazol-5-yl]-propoxy}-1H-indole-2-carboxylic acid ethyl ester (0.117 g, 0.234 mmol) is stirred with sodium hydride, 60% mineral oil (0.011 g, 0.28 mmol) and NN-dimethyl formamide (12 mL). Iodomethane (16 uL, 0.26 mmol) is added and the mixture is stirred at 80 deg C. 2 hr, and room temperature 18 hr. The mixture is diluted with water (50 mL), and the product is extracted into ethyl acetate (2×50 mL). The combined extracts are dried over anhydrous magnesium sulfate, filtered, concentrated, and purified via silica gel chromatography eluting with 8:2 hexanes:ethyl acetate to 6:4 hexanes:ethyl acetate to afford the title compound as a tan solid, 0.062 g, 51%). MS M$^+$+1 515. The structure is confirmed by $^1$H NMR spectroscopy.

Step B

5-{2-[4-Isopropyl-2-(4-trifluoromethyl-phenyl)-oxazol-5-yl]-propoxy}-1-methyl-1H-indole-2-carboxylic acid Hydrolysis of the ester from step A yields the title compound as a white solid. MS (ES) 487 (M$^+$+1). The structure is confirmed by $^1$H NMR spectroscopy.

The following compounds are made in similar manner:

EXAMPLE 18

(6-{2-[5-Methyl-2-(4-trifluoromethyl-phenyl)-oxazol-4-yl]-propoxy}-benzofuran-3-yl)-acetic acid

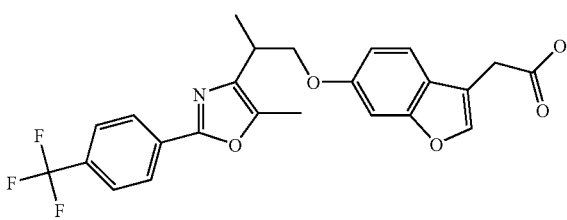

MS (ES): 460.13(M$^+$+1).

EXAMPLE 19

(6-{2-[4-Isopropyl-2-(4-trifluoromethyl-phenyl)-thiazol-5-yl]-propoxy}-benzofuran-3-yl)-acetic acid

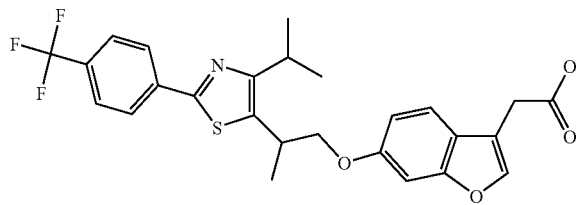

MS (ES): 504.11(M$^+$+1).

EXAMPLE 20

(6-{2-[4-Isopropyl-2-(4-trifluoromethyl-phenyl)-oxazol-5-yl]-propoxy}-benzofuran-3-yl)-acetic acid

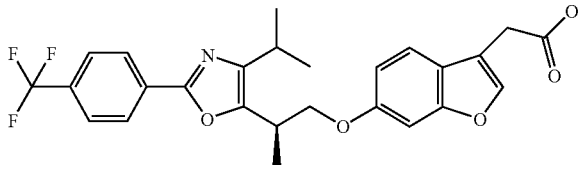

MS (ES): 488 (M$^+$+1). The structure is confirmed by $^1$H NMR spectroscopy.

EXAMPLE 21

(6-{2-[4-Isopropyl-2-(4-trifluoromethyl-phenyl)-oxazol-5-yl]-ethoxy}-benzofuran-3-yl)-acetic acid

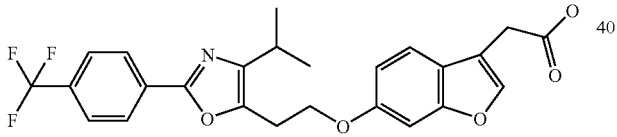

MS (ES): 474 (M$^+$+1).

EXAMPLE 22

{6-[4-Isopropyl-2-(4-trifluoromethyl-phenyl)-oxazol-5-ylmethoxy]-benzofuran-3-yl}-acetic acid

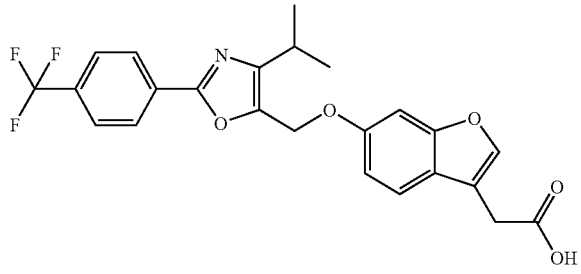

MS (ES): 460 (M$^+$+1).

EXAMPLE 23

(6-{1-Methyl-1-[4-methyl-2-(4-trifluoromethyl-phenyl)-oxazol-5-yl]-ethylsulfanyl}-benzofuran-3-yl)-acetic acid

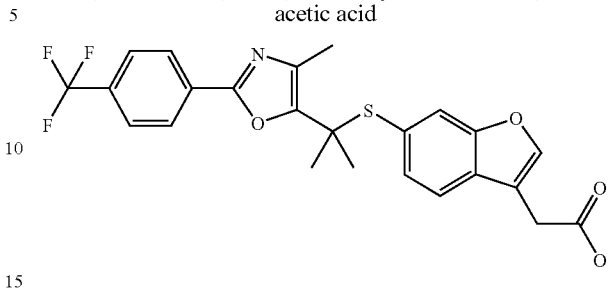

MS (ES): 476 (M$^+$+1). The structure is confirmed by $^1$H NMR spectroscopy.

EXAMPLE 24

{6-[4-Isopropyl-2-(4-trifluoromethyl-phenyl)-oxazol-5-ylmethylsulfanyl]-benzofuran-3-yl}-acetic acid

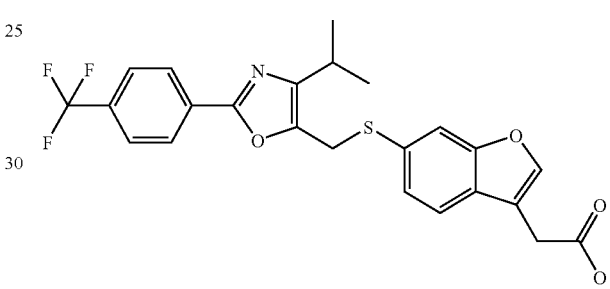

EXAMPLE 25

(6-{2-[4-Isopropyl-2-(4-trifluoromethyl-phenyl)-oxazol-5-yl]-ethylsulfanyl}-benzofuran-3-yl)-acetic acid

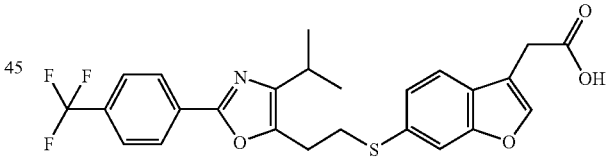

EXAMPLE 26

(6-{1-[4-Methyl-2-(4-trifluoromethyl-phenyl)-oxazol-5-yl]-ethylsulfanyl}-benzofuran-3-yl)-acetic acid

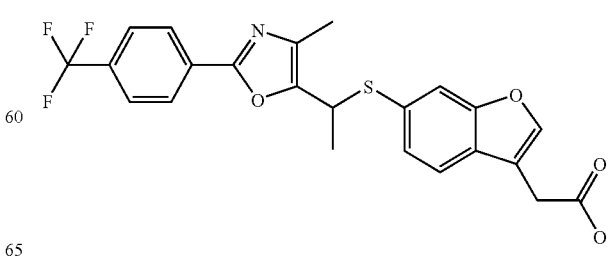

MS (ES): 462 (M$^+$+1).

EXAMPLE 27

2-{6-[4-Isopropyl-2-(4-trifluoromethyl-phenyl)-oxazol-5-ylmethoxy]-benzofuran-3-yl}-propionic acid

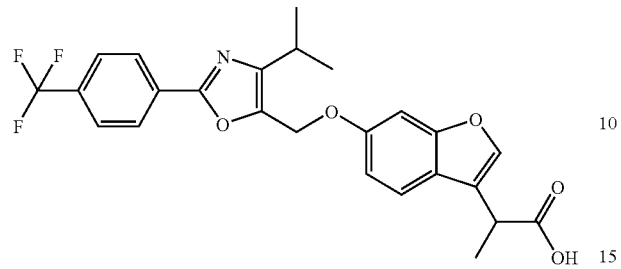

EXAMPLE 28

2-(6-{2-[4-Isopropyl-2-(4-trifluoromethyl-phenyl)-oxazol-5-yl]-ethoxy}-benzofuran-3-yl)-propionic acid

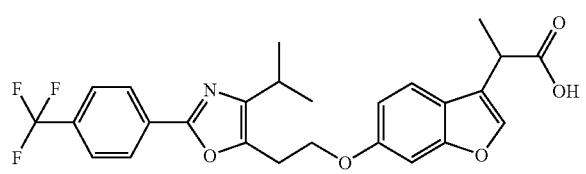

MS (ES): 488 (M$^+$+1).

EXAMPLE 29

(6-{2-[5-Methyl-2-(4-trifluoromethyl-phenyl)-thiazol-4-yl]-ethoxy}-benzofuran-3-yl)-acetic acid

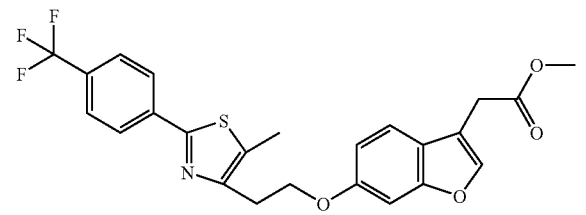

Step A (6-{2-[5-Methyl-2-(4-trifluoromethyl-phenyl)-thiazol-4-yl]-ethoxy}-benzofuran-3-yl)-acetic acid methyl ester To a solution of 2-[5-Methyl-2-(4-trifluoromethyl-phenyl)-thiazol-4-yl]-ethanol (0.12 g, 0.43 mmol) in toluene (3 mL) at 0° C. is added ADDP (0.14 g, 0.57 mmol) followed by tri-n-butylphosphine (0.14 mL, 0.56 mmol). A toluene solution of (6-Hydroxy-benzofuran-3-yl)-acetic acid methyl ester (0.52 g, 1.22 mmol) is added, and the mixture is allowed to warm to RT overnight. Water is added, and the aqueous phase is extracted with EtOAc. The organics are dried with MgSO$_4$ and purified by flash chromatography to yield the title compound (0.066 g, 33%).

Step B (6-{2-[5-Methyl-2-(4-trifluoromethyl-phenyl)-thiazol-4-yl]-ethoxy}-benzofuran-3-yl)-acetic acid (LY2110225)

A similar procedure is followed to yield the title compound. The material is purified by reverse phase chromatography (15 mg, 25%). MS (ES): 462 (M+); the structure is also confirmed by $^1$H NMR.

The following compounds are made in a similar manner:

EXAMPLE 30

(R)-(6-{2-[5-Methyl-2-(4-trifluoromethyl-phenyl)-thiazol-4-yl]-propoxy}-benzofuran-3-yl)-acetic acid (Isomer 2)

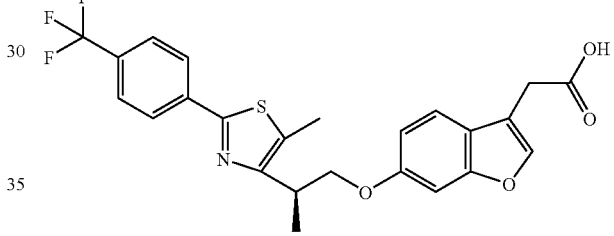

(24 mg, 77%). MS (ES): 476 (M+); the structure is also confirmed by $^1$H NMR.

EXAMPLE 31

(S)-(6-{2-[5-Methyl-2-(4-trifluoromethyl-phenyl)-thiazol-4-yl]-propoxy}-benzofuran-3-yl)-acetic acid

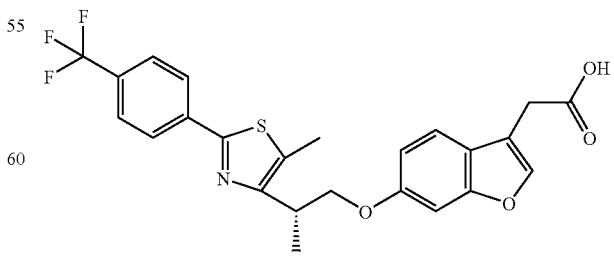

(29 mg, 66%). MS (ES): 476 (M$^+$); the structure is also confirmed by $^1$H NMR.

EXAMPLE 32

(6-{1-[4-Methyl-2-(4-trifluoromethyl-phenyl)-thiazol-5-yl]-ethoxy}-2-oxo-3,4-dihydro-2H-quinolin-1-yl)-acetic acid

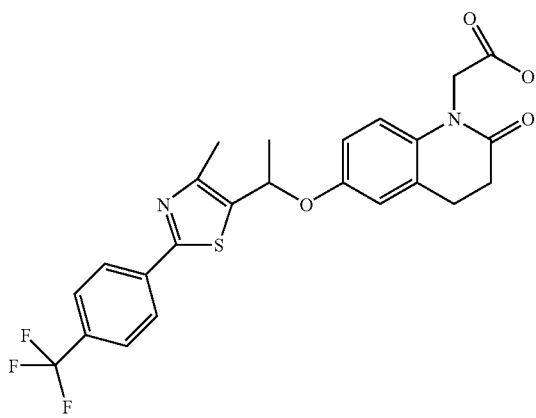

A solution of (6-hydroxy-2-oxo-3,4-dihydro-2H-quinolin-1-yl)-acetic acid tert-butyl ester (83 mg, 0.30 mmol) and 1-[4-methyl-2-(4-trifluoromethyl-phenyl)-thiazol-5-yl]-ethanol (58 mg, 0.20 mmol) in toluene (5.0 mL) is degassed and filled with nitrogen for 3 times. Tributylphosphine (60 mg, 0.30 mmol) is added to the reaction mixture under nitrogen at 0° C., followed by addition of of 1,1'-(azodicarbonyl)-dipiperidine (76 mg, 0.30 mmol). The reaction mixture is allowed to warm to room temperature and stirred overnight, the mixture is loaded directly on silica gel column chromatography to obtain the intermediate ester. The intermediate is then treated with TFA (1.0 ml), $CH_2Cl_2$ (1.0 ml), $H_2O$ (0.1 mL) and stirred for 2 hours, concentrated and purified on silica gel chromatography (Hexanes/EtOAc/HOAc, 5/5/0.02) afford the title compound (7 mg, 7%). MS (MH+): 491.2

The following compound is made in a similar manner:

EXAMPLE 33

{2-Oxo-6-[4-phenyl-2-(4-trifluoromethyl-phenyl)-thiazol-5-ylmethoxy]-3,4-dihydro-2H-quinolin-1-yl}-acetic acid

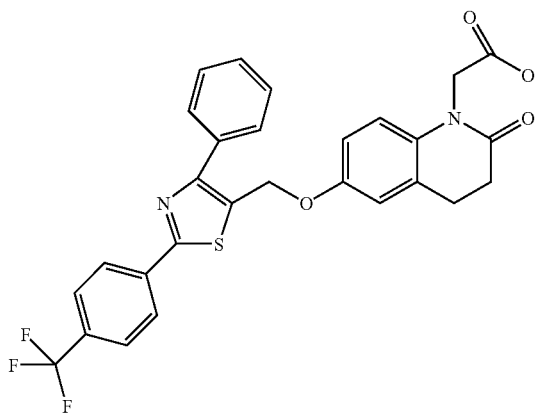

MS (MH+): 539.0; the structure is also confirmed by proton NMR.

EXAMPLE 34

{7-[4-Methyl-2-(4-trifluoromethyl-phenyl)-thiazol-5-ylmethoxy]-2-oxo-3,4-dihydro-2H-quinolin-1-yl}-acetic acid

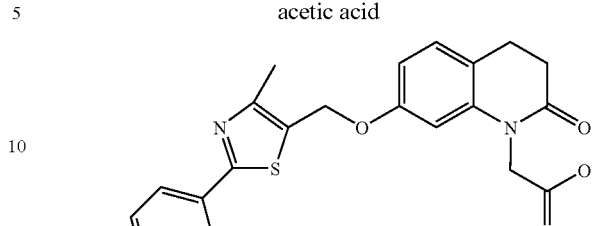

Step A

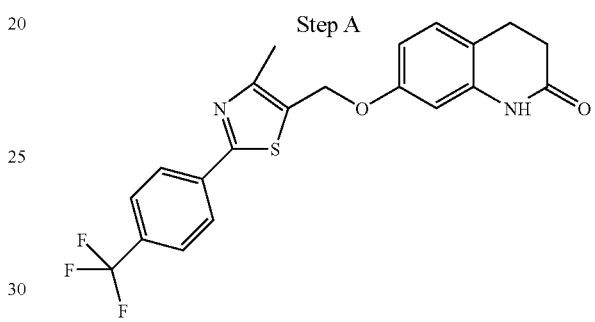

7-[4-Methyl-2-(4-trifluoromethyl-phenyl)-thiazol-5-ylmethoxy]-3,4-dihydro-1H-quinolin-2-one A solution of 7-hydroxy-3,4-dihydro-1H-quinolin-2-one (310 mg, 1.90 mmol) and 5-chloromethyl-4-methyl-2-(4-trifluoromethyl-phenyl)-thiazole (666 mg, 2.28 mmol) in DMF (3.0 mL) is treated with $Cs_2CO_3$ (1.25 g, 3.80 mmol). The resulting suspension is heated at 60° C. for 5 hours and then quenched with water dropwise. The mixture is extracted with EtOAc (40 mL×3) and the combined organics are dried ($Na_2SO_4$), concentrated to a suspension. It is then filtered and the solid is rinsed with EtOAc (2 mL) and dried under vacuum to obtain pure product (233 mg, 29%).

Step B

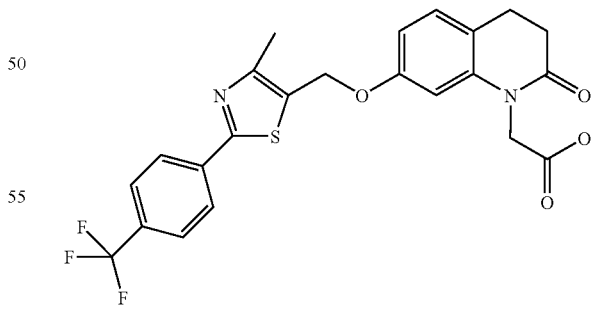

{7-[4-Methyl-2-(4-trifluoromethyl-phenyl)-thiazol5-ylmethoxy]-2-oxo-3,4-dihydro-2H-quinolin-1-yl}-acetic acid A solution of 7-[4-methyl-2-(4-trifluoromethyl-phenyl)-thiazol-5-ylmethoxy]-3,4-dihydro-1H-quinolin-2-one (233 - mg, 0.557 mmol) in DMF (3.0 mL) is treated with NaH (67 mg, 1.67 mmol, 60%). The resulting suspension is heated at 57° C. for 40 minutes and cooled to room temperature. The t-butyl bromoacetate (217 mg, 1.11 mmol) is added and the suspension is stirred for 2 hours and then quenched with water. The mixture is extracted with EtOAc (30 mL×2) and the combined organics are dried (Na$_2$SO$_4$), concentrated, and purified on silica gel chromatography column with 20% EtOAc/Hexanes to obtain the intermediate compound. The intermediate is then treated with TFA (1.0 ml), CH$_2$Cl$_2$ (1.0 ml), H$_2$O (0.1 mL) and stirred for 2 hours, concentrated and purified on silica gel chromatography (Hexanes/EtOAc/HOAc, 5/5/0.02) afford the title compound (65 mg, 25%). MS (MH+): 477.1; the structure is also confirmed by proton NMR.

The following compound is made in a similar manner:

EXAMPLE 35

{8-[4-Methyl-2-(4-trifluoromethyl-phenyl)-thiazol-5-ylmethoxy]-2-oxo-2,3,4,5-tetrahydro-benzo[b]azepin-1-yl}-acetic acid

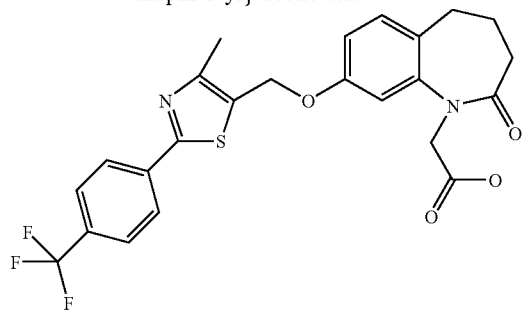

MS (MH+): 491.2; the structure is also confirmed by proton NMR.

EXAMPLE 36

(6-{1-[3-Methyl-1-(4-trifluoromethyl-phenyl)-1H-pyrazol-4-yl]-ethylsulfanyl}-benzofuran-3-yl)-acetic acid

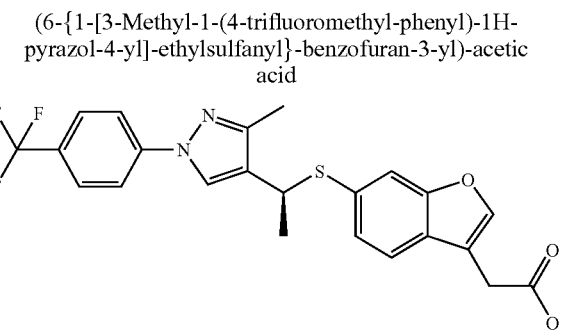

MS (ES) 474 (M$^+$+1). The structure is confirmed by $^1$H NMR spectroscopy.

EXAMPLE 37

{6-[3-Methyl-1-(4-trifluoromethyl-phenyl)-1H-pyrazol-4-ylmethylsulfanyl]-benzofuran-3-yl}-acetic acid

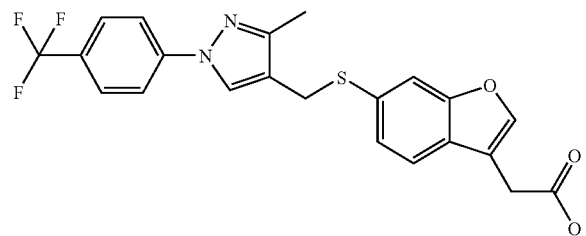

MS (ES): 447 (M$^+$+1). The structure is confirmed by $^1$H NMR spectroscopy.

EXAMPLE 38

(6-{1-[3-Methyl-1-(4-trifluoromethyl-phenyl)-1H-pyrazol-4-yl]-ethoxy}-benzofuran-3-yl)-acetic acid

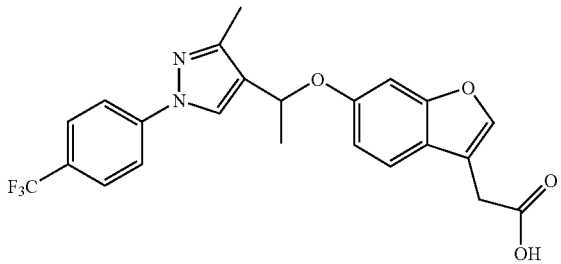

MS (ES): 445 (M$^+$+1). The structure is confirmed by $^1$H NMR spectroscopy.

EXAMPLE 39

2-{5-[1-(3,5-Bis-trifluoromethyl-phenyl)-5-methyl-1H-pyrazol-4-ylmethoxy]-indol-1-yl}-2-methyl-propionic acid

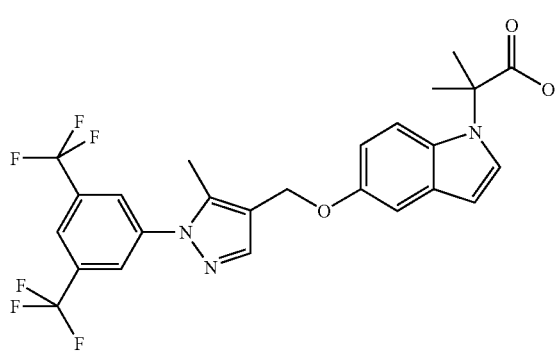

Step A

2-{5-[1-(3,5-Bis-trifluoromethyl-phenyl)-5-methyl-1H-pyrazol-4-ylmethoxy]-indol-1-yl}-2-methyl-propionic acid ethyl ester To a solution of 1-(3,5-bis-trifluoromethyl-phenyl)-4-chloromethyl-5-methyl-1H-pyrazole (170 mg, 0.5 mmol) and (2-(5-hydroxy-indol-1-yl)-2-methyl-propionic acid (150 mg) in acetonitrile (3 mL) is added Cs2CO3 (325 mg, 1 mmol). The mixture is stirred at room temperature overnight, quenched by water, extracted with ethyl acetate, dried over sodium sulfate. Concentration yields the crude product.

Step B

2-{5-[1-(3,5-Bis-trifluoromethyl-phenyl)-5-methyl-1H-pyrazol-4-ylmethoxy]-indol-1-yl}-2-methyl-propionic acid 2-{5-[1-(3,5-Bis-trifluoromethyl-phenyl)-5-methyl-1H-pyrazol-4-ylmethoxy]-indol-1-yl}-2-methyl-propionic acid ethyl ester from step A in ethanol (2 mL) is added NaOH (5.0 M, 1 mL). After heated at 50° C. for 2 hrs, ethanol is evaporated. The residue is diluted with water, acidified with 5 N HCl, extracted with ether, dried over sodium sulfate. Concentration and purification by reversed phase HPLC (acetone/ water/TFA as eluents) yields the title compound (60 mg). MS (ES): 525.96(M⁺−1); the structure is also confirmed by $^1$H NMR.

EXAMPLE 40

(1-Methyl-6-{2-[3-methyl-1-(4-trifluoromethyl-phenyl)-1H-pyrazol-4-yl]-propoxy}-1H-indol-3-yl)-acetic acid

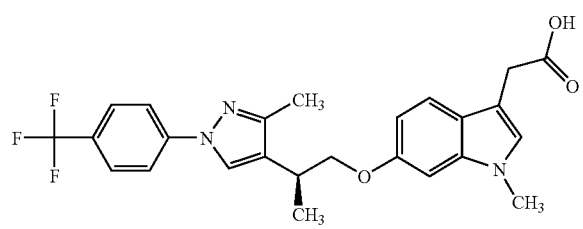

MS: m/z (M⁺+1) 472.2. The structure is also confirmed by proton NMR.

The following compounds are made in a substantially similar manner:

EXAMPLE 41

{5-[2-(5-Methyl-3-phenyl-pyrazol-1-yl)-ethoxy]-indol-1-yl}-acetic acid

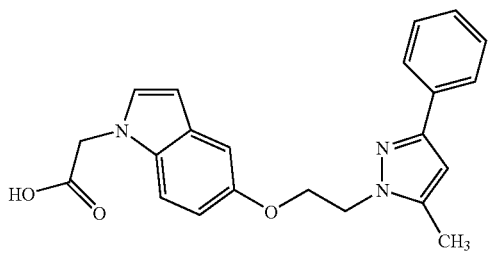

MS (ES): 374.04(M⁺−1).

EXAMPLE 42

(1-Methyl-6-{2-[3-methyl-1-(4-trifluoromethyl-phenyl)-1H-pyrazol-4-yl]-propoxy}-1H-indol-3-yl)-acetic acid

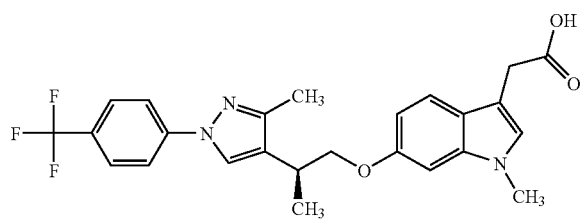

Step 1

2-[3-Methyl-1-(4-trifluoromethyl-phenyl)-1H-pyrazol-4-yl]-propan-1-ol (150 mg, 0.5276 mmol) is dissolved into anhydrous toluene (2 mL) and cooled in an ice bath to 0° C. with stirring under nitrogen. Tributyl phosphine (200 uL, 0.7914 mmol) is added by syringe followed by 1-1'-azodicarbonyl-dipiperidine (200 mg, 0.7914 mmol). Finally, (6-Hydroxy-1-methyl-1H-indol-3-yl)-acetic acid methyl ester (145 mg, 0.6596 mmol) is then added. The reaction is allowed to stir under nitrogen at 0° C. for 1 hour, then room temperature and monitored by TLC and HPLC. Upon completion, the reaction is diluted with hexanes and allowed to stir vigorously for 10 min. The resulting white precipitate is then filtered away and the solution is concentrated under vacuum. The residue is further purified using either EtOAc/Hexanes (1:9) or Acetone/Hexanes (1:9) gradients on silica gel chromatography to yield (1-Methyl-6-{2-[3-methyl-1-(4-trifluoromethyl-phenyl)-1H-pyrazol-4-yl]-propoxy}-1H-indol-3-yl)-acetic acid methyl ester (150 mg, 0.309 mmol) or 59%.

Step 2

(1-Methyl-6-{2-[3-methyl-1-(4-trifluoromethyl-phenyl)-1H-pyrazol-4-yl]-propoxy}-1H-indol-3-yl)-acetic acid methyl ester (150 mg, 0.309 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the pure (1-Methyl-6-{2-[3-methyl-1-(4-trifluoromethyl-phenyl)-1H-pyrazol-4-yl]-propoxy}-1H-indol-3-yl)-acetic acid (122 mg, 0.2586 mmol), or 84% yield.

EXAMPLE 43 (ISOMER II)

(1-Methyl-6-{2-[4-methyl-2-(4-trifluoromethyl-phenyl)-thiazol-5-yl]-propoxy}-1H-indol-3-yl)-acetic acid

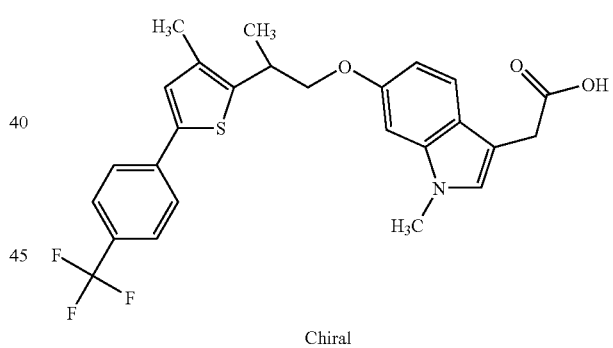

Chiral

MS (ES): 488.07 (M⁺+H), the structure is also confirmed by proton NMR.

EXAMPLE 44

{5-[5-(4-Trifluoromethyl-phenyl)-thiophen-2-yl-methoxy]-indol-1-yl}-acetic acid

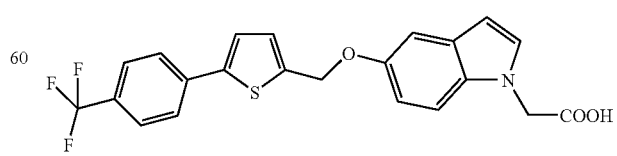

MS (ES): 430 (M+H)⁻, the structure is also confirmed by proton NMR.

Synthesis Method to Make Indoles Below

Step A

3-{2-Methyl-4-[5-(4-trifluoromethyl-phenyl)-thiophen-2-ylmethoxy]-phenyl}-propionic acid methyl ester To a solution of [5-(4-Trifluoromethyl-phenyl)-thiophen-2-yl]-methanol (0.063 g, 0.232 mmole) and 3-(4-Hydroxy-2-methyl-phenyl)-propionic acid methyl ester (0.045 g, 0.232 mmole) in toluene (2 mL) at room temperature, is added tributylphosphine (0.087 mL, 0.348 mmole) followed by a solution of 1,1'-(azodicarbonyl)-dipiperidine (0.088 g, 0.348 mmole) in toluene (2 mL). The reaction is stirred overnight, and then diluted with hexane (10 mL). The precipitate is removed through filtration and the filtrate is concentrated, loaded to a silica gel column, eluted with ethyl acetate in hexane (0-15%) and concentrated to provide the titled compound as white solid.

Step B

3-{2-Methyl-4-[3-methyl-5-(4-trifluoromethyl-phenyl)-thiophen-2-ylmethoxy]-phenyl}-propionic acid 3-{2-Methyl-4-[5-(4-trifluoromethyl-phenyl)-thiophen-2-ylmethoxy]-phenyl}-propionic acid methyl ester (0.043 g, 0.0959 mmole) is treated with a mixture of $NaOH_{(aq)}$ (1 mL)/THF (3 mL)/MeOH (3 mL) at room temperature overnight. The organic solvents are removed on rota-vapor. The residue is diluted with water (10 mL), acidified to pH=2 with 6N $HCl_{(aq)}$. The precipitate is collected through filtration, washed with cold water (30 mL) and dried to provide the titled compound as a white solid. MS (ES): 433 (M+H); the structure is also confirmed by proton NMR. A substantially similar process is used to make the following compound and the Compound of Example 45, below.

EXAMPLE 45

3-{4-[3-Isobutyl-5-(4-trifluoromethyl-phenyl)-thiophen-2-ylmethoxy]-2-methyl-phenyl}-propionic acid

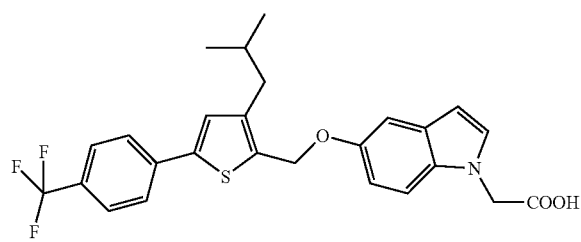

MS (ES): 488 $(M+H)^+$, 486 $(M+H)^-$, the structure is also confirmed by proton NMR.

EXAMPLE 46

(5-{2-[3-Methyl-5-(4-trifluoromethyl-phenyl)-thiophen-2-yl]-propoxy}-indol-1-yl)-acetic acid

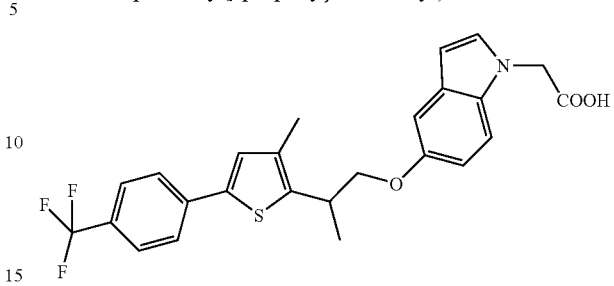

MS (ES): 474 $(M+H)^+$, 472 $(M+H)^-$; the structure is also confirmed by proton NMR.

EXAMPLE 47

(6-{1-[3-Methyl-1-(4-trifluoromethyl-phenyl)-1H-pyrazol-4-yl]-ethylsulfanyl}-benzofuran-3-yl)-acetic acid

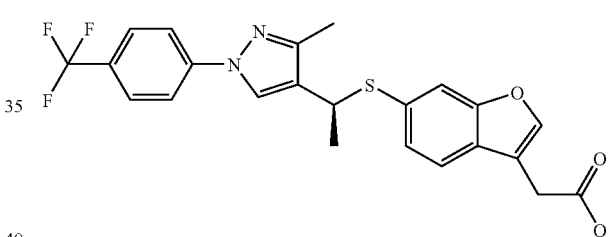

MS (ES) 474 $(M^++1)$. The structure is confirmed by $^1H$ NMR spectroscopy.

EXAMPLE 48

{6-[3-Methyl-1-(4-trifluoromethyl-phenyl)-1H-pyrazol-4-ylmethylsulfanyl]-benzofuran-3-yl}-acetic acid

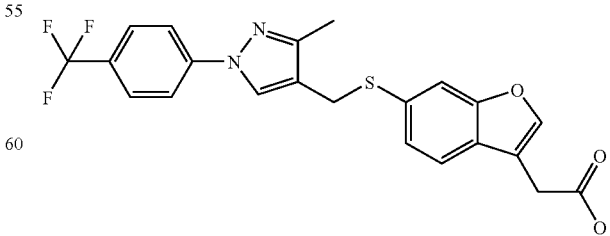

MS (ES): 447 (M++i). The structure is confirmed by $^1H$ NMR spectroscopy.

EXAMPLE 49

(6-{1-[3-Methyl-1-(4-trifluoromethyl-phenyl)-1H-pyrazol-4-yl]-ethoxy}-benzofuran-3-yl)-acetic acid

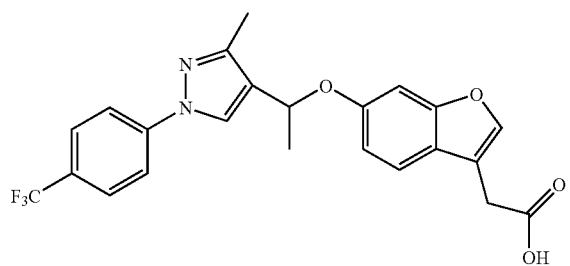

MS (ES): 445 (M$^+$+1). The structure is confirmed by 1H NMR spectroscopy.

EXAMPLE 50

2-{5-[1-(3,5-Bis-trifluoromethyl-phenyl)-5-methyl-1H-pyrazol-4-ylmethoxy]-indol-1-yl}-2-methyl-propionic acid

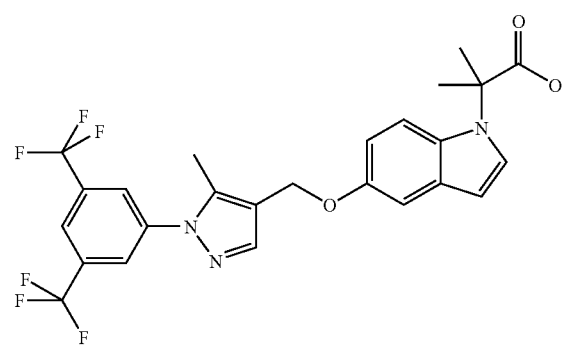

Step A

2-{5-[1-(3,5-Bis-trifluoromethyl-phenyl)-5-methyl-1H-pyrazol-4-ylmethoxy]-indol-1-yl}-2-methyl-propionic acid ethyl ester To a solution of 1-(3,5-bis-trifluoromethyl-phenyl)-4-chloromethyl-5-methyl-1H-pyrazole (170 mg, 0.5 mmol) and (2-(5-hydroxy-indol-1-yl)-2-methyl-propionic acid (150 mg) in acetonitrile (3 mL) is added Cs2CO3 (325 mg, 1 mmol). The mixture is stirred at room temperature over night, quenched by water, extracted with ethyl acetate, dried over sodium sulfate. Concentration yields the crude product.

Step B

2-{5-[1-(3,5-Bis-trifluoromethyl-phenyl)-5-methyl-1H-pyrazol-4-ylmethoxy]-indol-1-yl}-2-methyl-propionic acid 2-{5-[1-(3,5-Bis-trifluoromethyl-phenyl)-5-methyl-1H-pyrazol-4-ylmethoxy]-indol-1-yl}-2-methyl-propionic acid ethyl ester from step A in ethanol (2 mL) is added NaOH (5.0 M, 1 mL). After heated at 50° C. for 2 hrs, ethanol is evaporated. The residue is diluted with water, acidified with 5 N HCl, extracted with ether, dried over sodium sulfate. Concentration and purification by reversed phase HPLC (acetone/water/TFA as eluents) yields the title compound (60 mg). MS (ES): 525.96(M$^+$–1); the structure is also confirmed by $^1$H NMR.

EXAMPLE 51

(1-Methyl-6-{2-[3-methyl-1-(4-trifluoromethyl-phenyl)-1H-pyrazol-4-yl]-propoxy}-1H-indol-3-yl)-acetic acid

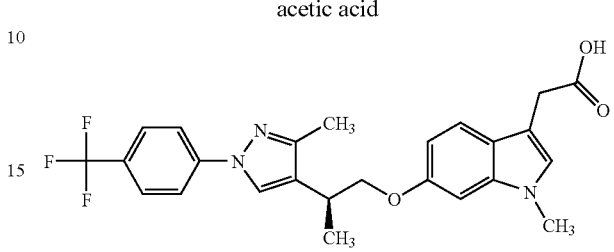

MS: m/z (M$^+$+1) 472.2. The structure is also confirmed by proton NMR.

The following compounds are made in a substantially similar manner:

EXAMPLE 52

{5-[2-(5-Methyl-3-phenyl-pyrazol-1-yl)-ethoxy]-indol-1-yl}-acetic acid

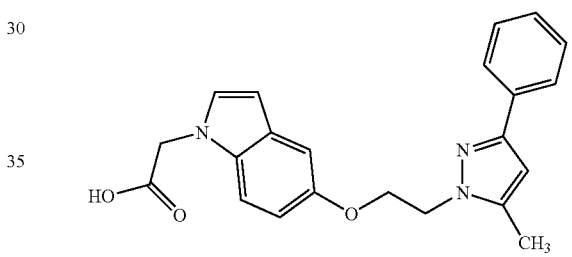

MS (ES): 374.04(M$^+$–1).

EXAMPLE 53

(1-Methyl-6-{2-[3-methyl-1-(4-trifluoromethyl-phenyl)-1H-pyrazol-4-yl]-propoxy}-1H-indol-3-yl)-acetic acid

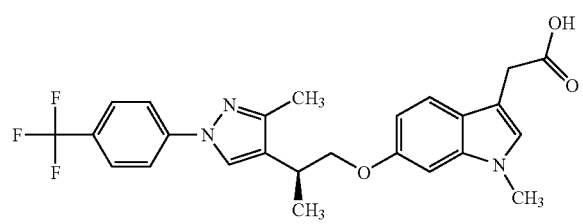

Step 1

2-[3-Methyl-1-(4-trifluoromethyl-phenyl)-1H-pyrazol-4-yl]-propan-1-ol (150 mg, 0.5276 mmol) is dissolved into anhydrous toluene (2 mL) and cooled in an ice bath to 0° C. with stirring under nitrogen. Tributyl phosphine (200 uL, 0.7914 mmol) is added by syringe followed by 1-1'-azodicarbonyl-dipiperidine (200 mg, 0.7914 mmol). Finally, (6-Hydroxy-1-methyl-1H-indol-3-yl)-acetic acid methyl ester (145 mg, 0.6596 mmol) is then added. The reaction is allowed to stir under nitrogen at 0° C. for 1 hour, then room temperature and monitored by TLC and HPLC. Upon completion, the reaction is diluted with hexanes and allowed to stir vigorously for 10 min. The resulting white precipitate is then filtered away and the solution is concentrated under vacuum. The residue is further purified using either EtOAc/Hexanes (1:9) or Acetone/Hexanes (1:9) gradients on silica gel chromatography to yield (1-Methyl-6-{2-[3-methyl-1-(4-trifluoromethyl-phenyl)-1H-pyrazol-4-yl]-propoxy}-1H-indol-3-yl)-acetic acid methyl ester (150 mg, 0.309 mmol) or 59%.

Step 2

(1-Methyl-6-{2-[3-methyl-1-(4-trifluoromethyl-phenyl)-1H-pyrazol-4-yl]-propoxy}-1H-indol-3-yl)-acetic acid methyl ester (150 mg, 0.309 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the pure (1-Methyl-6-{2-[3-methyl-1-(4-trifluoromethyl-phenyl)-1H-pyrazol-4-yl]-propoxy}-1H-indol-3-yl)-acetic acid (122 mg, 0.2586 mmol), or 84% yield.

EXAMPLE 54

Racemic-{5-[2-(4-Trifluoromethyl-phenyl)-5,6-dihydro-4H-cyclopentathiazol-4-ylmethoxy]-indol-1-yl}-acetic acid

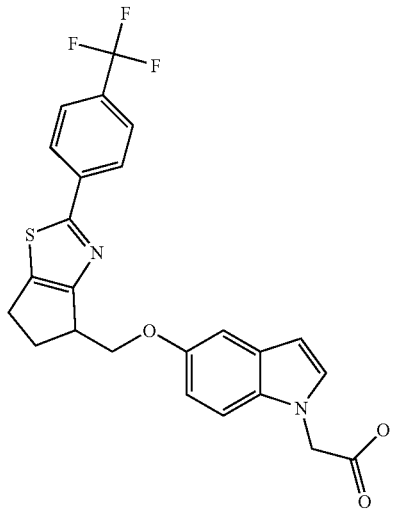

MS (ES): 473.45(M$^+$+1).

EXAMPLE 55

(S)-{6-[2-(4-Trifluoromethyl-phenyl)-5,6-dihydro-4H-cyclopentathiazol-4-ylmethoxy]-1H-indol-3-yl}-acetic acid

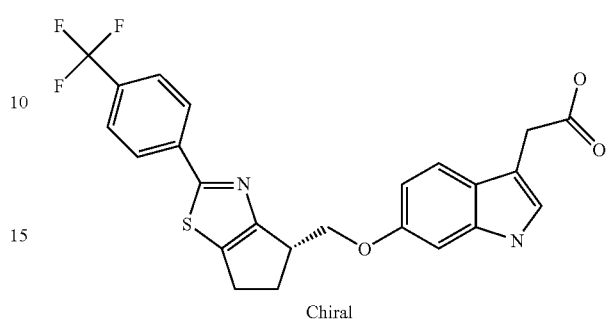

MS (ES): 473.11(M$^+$+1).

EXAMPLE 56

{1-Methyl-6-[2-(4-trifluoromethyl-phenyl)-5,6-dihydro-4H-cyclopentathiazo-4-ylmethoxy]-1H-indol-3-yl}-acetic acid

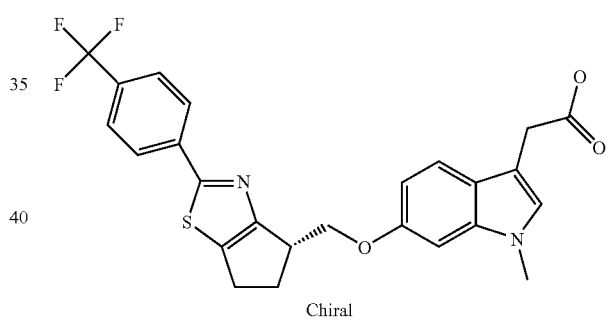

MS (ES): 487.09(M$^+$+1).

EXAMPLE 57

{5-[2-(4-Trifluoromethyl-phenyl)-4,5,6,7-tetrahydro-benzothiazol-4-ylmethoxy]-indol-1-yl}-acetic acid

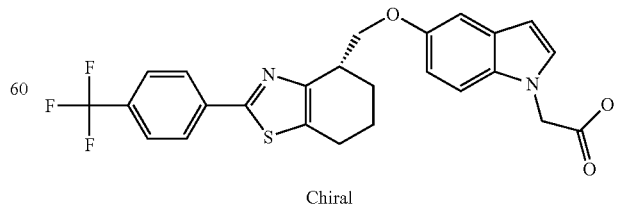

MS (ES): 485.06(M$^+$+1).

EXAMPLE 58

{6-[2-(4-Trifluoromethyl-phenyl)-4,5,6,7-tetrahydro-benzothiazol-4-ylmethoxy]-1H-indol-3-yl}-acetic acid

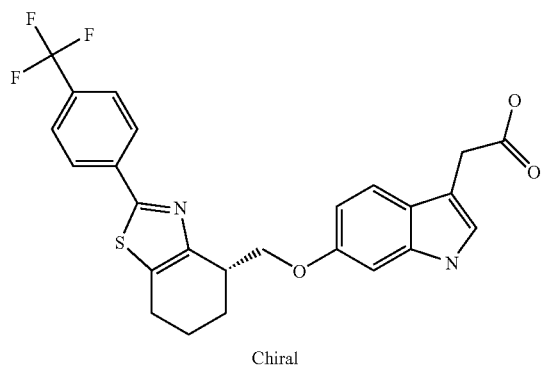

MS (ES): 487.06(M$^+$+1).

EXAMPLE 59

{6-[2-(4-Trifluoromethyl-phenyl)-4,5,6,7-tetrahydro-benzothiazol-4-ylmethoxy]-1H-indol-3-yl}-acetic acid

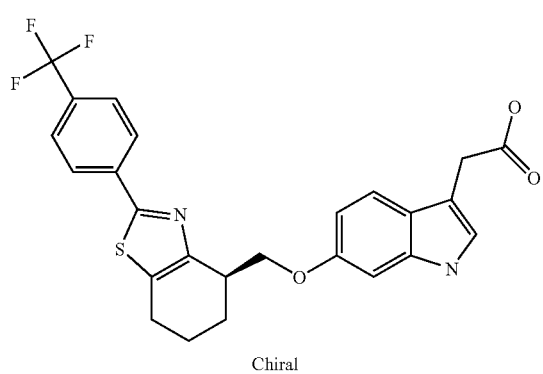

MS (ES): 487.08(M$^+$+1).

EXAMPLE 60

{-Methyl-6-[2-(4-trifluoromethyl-phenyl)-4,5,6,7-tetrahydro-benzothiazol-4-ylmethoxy]-1H-indol-3-yl}-acetic acid

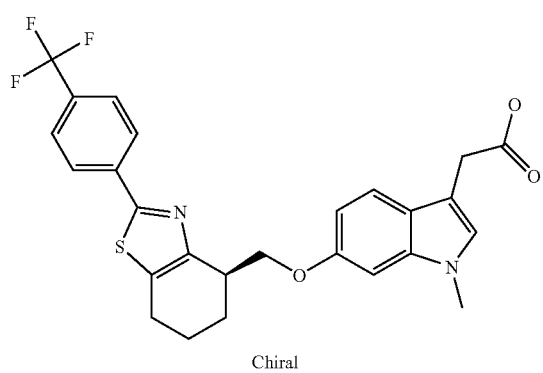

MS (ES): 501.08(M$^+$+1).

EXAMPLE 61

{5-[2-(4-Trifluoromethyl-phenyl)-4,5,6,7-tetrahydro-benzothiazol-4-ylmethoxy]-indol-1-yl}-acetic acid

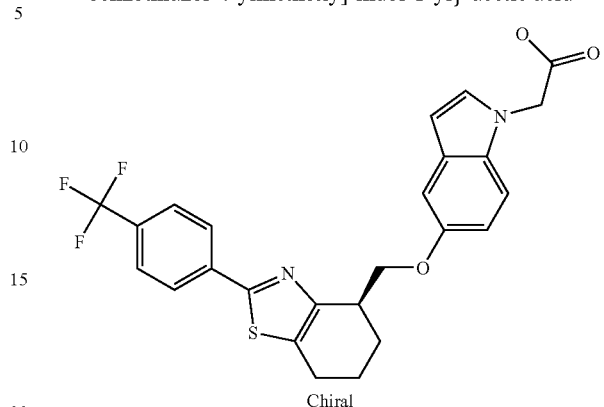

MS (ES): 487.12(M$^+$+1).

EXAMPLE 62

{1-Methyl-6-[2-(4-trifluoromethyl-phenyl)-5,6,7,8-tetrahydro-4H-cycloheptathiazol-4-ylmethoxy]-1H-indol-3-yl}-acetic acid

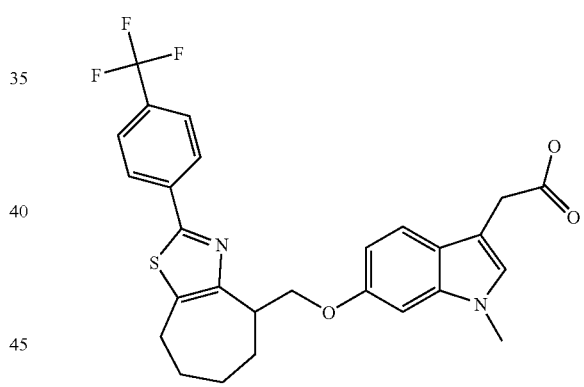

MS (ES): 515.13(M$^+$+1).

EXAMPLE 63

2-(6-((1-(4-(trifluoromethyl)phenyl)-3-methyl-1H-pyrazol-4-yl)methoxy)benzo[b]thiophen-3-yl)acetic acid

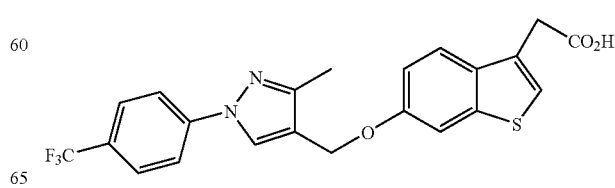

EXAMPLE 64

2-(6-(2-(1-(4-(trifluoromethyl)phenyl)-3-methyl-1H-pyrazol-4-yl)propoxy)benzo[b]thiophen-3-yl)acetic acid

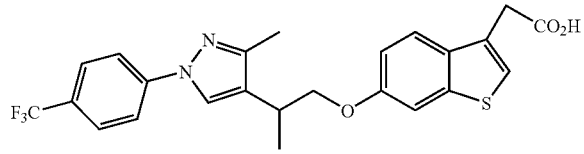

EXAMPLE 65

2-(6-(2-(1-(4-(trifluoromethyl)phenyl)-3-methyl-1H-pyrazol-4-yl)propoxy)benzo[b]thiophen-3-yl)acetic acid

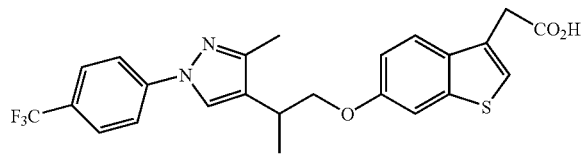

EXAMPLE 66

2-(6-((R)-2-(1-(4-(trifluoromethyl)phenyl)-3-methyl-1H-pyrazol-4-yl)propylthio)benzo[b]thiophen-3-yl)acetic acid

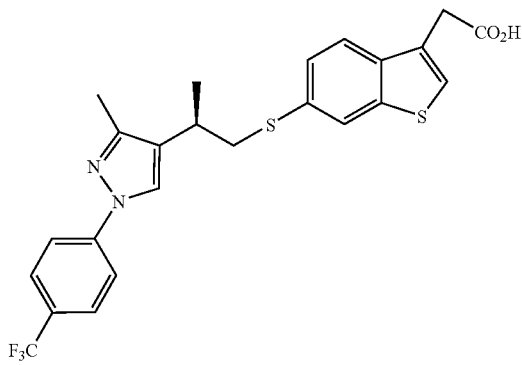

EXAMPLE 67

2-(6-((1-(4-(trifluoromethyl)phenyl)-3-isopropyl-1H-pyrazol-4-yl)methylthio)benzo[b]thiophen-3-yl)acetic acid

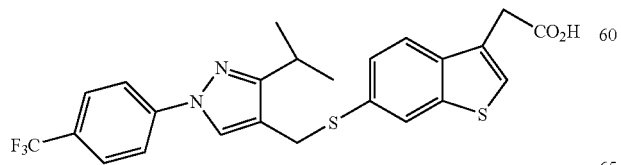

EXAMPLE 68

2-(6-((4-tert-butyl-2-(4-(trifluoromethyl)phenyl)thiazol-5-yl)methylthio)benzo[b]thiophen-3-yl)acetic acid

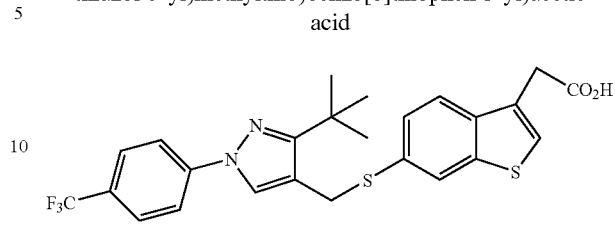

EXAMPLE 69

6-[2-(4-Trifluoromethylphenyl)benzooxazol-7-yl-methoxy]benzo[b]thiophen-3-ylacetic Acid

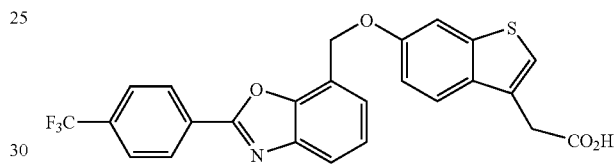

mp: 215-216° C.; $^1$H NMR (DMSO-$d_6$) □ 12.37 (s br, 1H), 8.41 (d, J=8.2 Hz, 2H), 7.98 (d, J=8.2 Hz, 2H), 7.86 (d, J=8.1 Hz, 1H), 7.79 (d, J=2.3 Hz, 1H), 7.70 (d, J=8.7 Hz, 1H), 7.62 (d, J=7.5 Hz, 1H), 7.48 (t, J=7.8 Hz, 1H), 7.39 (s, 1H), 7.18 (dd, J=8.7, 2.5 Hz, 1H), 5.58 (s, 2H), 3.79 (s, 2H); ESI MS m/z 484 $[C_{25}H_{16}F_3NO_4S+H]^+$. HPLC analysis (retention time=12.3 min) shows one peak, with a total purity of >99% (area percent).

EXAMPLE 70

6-[2-(4-Trifluoromethylphenyl)benzooxazol-7:ylm-ethylsulfanyl]benzo[b]thiophen 3-ylacetic Acid

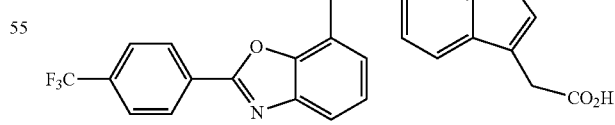

mp: 208-210° C.; $^1$H NMR (DMSO-$d_6$) δ 3.71 (s, 21), 4.62 (s, 2H), 7.22-7.44 (m, 3H), 7.50 (s, 1H), 7.66(d, 2H), 7.71 (dd, 1H), 7.92 (d, 2H), 8.03 (d, 1H), 8.22 (d, 2H), 12.42 (s, 1H); ESI MS m/z 500 $[C_{25}H_{16}F_3NO_3S_2+H]^+$. HPLC analysis (retention time=13.1 min) shows one peak, with a total purity of 97.4% (area percent).

EXAMPLE 71

2-(6-((2-(4-(trifluoromethyl)phenyl)-4-isopropylthiazol-5-yl)methoxy)benzo[b]thiophen-3-yl)acetic acid

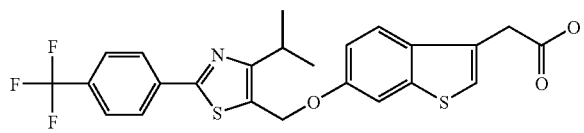

EXAMPLE 72

2-(6-((R)-2-(2-(4-(trifluoromethyl)phenyl)-4-isopropyloxazol-5-yl)propoxy)benzofuran-3-yl)acetic acid

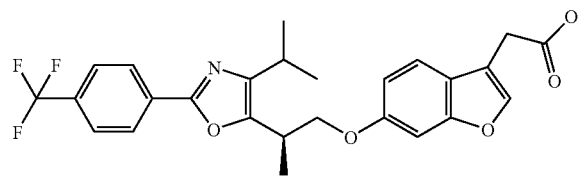

EXAMPLE 73

2-(6-(2-(2-(4-(trifluoromethyl)phenyl)4-isopropyloxazol-5-yl)propoxy)benzo[b]thiophen-3-yl)acetic acid

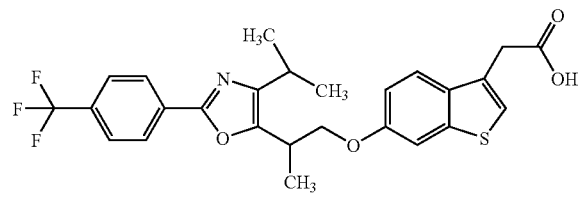

EXAMPLE 74

2-(6-(2-(2-(4-(trifluoromethyl)phenyl)-4-isopropyloxazol-5-yl)propoxy)benzofuran-3-yl)acetic acid

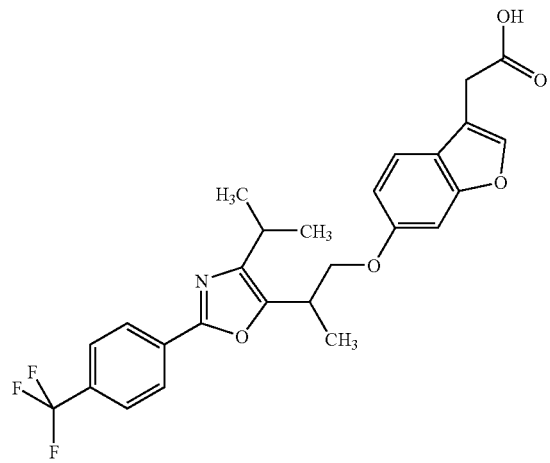

Biological Assays

Binding and Cotransfection Studies

The in vitro potency of compounds in modulating PPARα receptors are determined by the procedures detailed below. DNA-dependent binding (ABCD binding) is carried out using SPA technology with PPAR receptors. Tritium-labeled PPARα agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values for compounds of the invention which are especially useful for modulating a PPAR receptor, are <100 nM and >50%, respectively.

Evaluation of Triglyceride Reduction and HDL Cholesterol Elevation in HuapoAI Transgenic Mice Compounds of the present invention are studied for effects upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured colorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542,1983; Allain C. C. et al., Clin Chem 20:470-475, 1974. Commercially available standards for triglycerides and total cholesterol, respectively, commercial quality control plasma, and samples are measured in duplicate using 200 µl of reagent. An additional aliquot of sample, added to a well containing 200 µl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow stream at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects upon plasma glucose associated with administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, C57BIKs/j-m +/+ Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured colorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provided a blank for each specimen. Plates are incubated at room temperature for 18 minutes for glucose on a plate shaker (DPC Micromix 5) and absorbance read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7

A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealing a significant reduction in respiratory quotient (RQ) in treated animals during the dark cycle [0.864+0.013 (Control) vs. 0.803+0.007 (Treated); p<0.001] is indicative of an increased utilization of fat during the animals' active (dark) cycle and can be used to selected especially desired compounds of this invention. Additionally, treated animals displaying significantly higher rates of energy expenditure than control animals suggest such compounds of this invention can be especially desired.

Male KK/A$^y$ Mice

Male KK/A$^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-cholesterol Total-cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster received once a day approx. 1 ml of the solution by gavage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's procedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. Especially desired compounds are markedly more potent than fenofibrate in LDL-lowering efficacy. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPARModulators

Zucker Fatty Rat Model:

The life phase of the study on fibrinogen-lowering effect of compounds of this invention is part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a ½₀ dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples.

Compounds that lower fibrinogen level greater than vehicle can be especially desired.

Cholesterol and triglyceride lowering effects of compounds of this invention are also studied in Zucker rats.

Method to Elucidate the Anti-body Weight Gain and Anti-appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat received once a day approximately 1 ml of the solution by gavage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Using this assay, compounds of this invention are identified to determine which can be associated with a significant weight reduction.

Monkey Studies

Efficacy Studies

Compounds of the invention may be examined in a dyslipidemic rhesus monkey model. After an oral dose-escalation study for 28 days in obese, non-diabetic rhesus monkeys a determination of HDL-c elevation is made with each dose and compared with pretreatment levels. LDL cholesterol is also determined with each dose. C-reactive protein levels are measured and compared to pretreatment levels.

Compound of Formula 1 may be shown to elevate plasma HDL-cholesterol levels in an African Green Monkey model in a manner similar to that described above in rhesus monkeys. Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to measured, for example:
Bodyweight
Total plasma cholesterol
HDL
LDL
Triglycerides
Insulin
Glucose
PK parameters at week 4, 7, and 10 (plasma drug concentration at last week of each dose)
ApoAI
ApoAII
ApoB
ApoCIII
Liver enzymes (SGPT, SGOT, □GT)
Complete blood count Additionally, other measures may be made, as appropriate, and consistent with the stated study design.

Equivalents:

While this invention has been particularly shown and described with references to preferred embodiments thereof, it will be understood by those skilled in the art that various changes in form and details may be made therein without departing from the scope of the invention encompassed by the appended claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following Structural Formula:

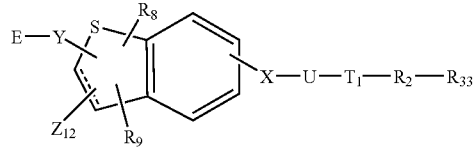

or a stereoisomer, pharmaceutically acceptable salt, or hydrate thereof, wherein:

(a) T1 is a moiety of formula

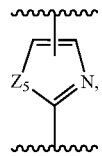

optionally substituted with
one substituent selected from $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, wherein $C_1$-$C_8$ alkyl, $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents independently selected from R1'; or
one substituent selected form $C_3$-$C_6$ alkyl, $C_1$-$C_6$ haloalkyl, and $C_1$-$C_6$ alkyloxo; and;

(b) R1', R26, R27, R28, R31, Z14', and Z15' are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2 is selected from the group consisting of $C_0$-$C_8$ alkyl and $C_{1-6}$-heteroalkyl;

(d) X is selected from the group consisting of a bond, O, S, S(O)$_2$ and N;

(e) U is an aliphatic linker wherein one carbon atom of the aliphatic linker may be replaced with O, NH or S, and wherein such aliphatic linker is optionally substituted with R30;

(f) Y is selected from the group consisting of C, O, S, NH and a single bond;

(g) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl-$C_0$-$C_4$ alkyl and $C_1$-$C_6$ alkyl, wherein such alkyl and arylalkyl are each optionally substituted with from one to two groups independently selected from R7'; each R7' is independently selected from halo, $C_1$-$C_6$ alkyl, and halo$C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of hydrogen, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(h) Z5 is S or O;

(i) Z12 is selected from the group consisting of hydrogen and -Z13$C_0$-$C_3$alkylZ14;

(j) Z13 is selected from the group consisting of a single bond, CO, $CO_2$, CONZ15, and $SO_2$;

(k) Z14 is selected from the group consisting of aryl and heteroaryl, wherein the aryl and heteroaryl is each optionally substituted with from one to three substituents independently selected from Z14';

(l) Z15 is selected from the group consisting of hydrogen, aryl, and heteroaryl, wherein the aryl and heteroaryl is each optionally substituted with from one to three substituents independently selected from Z15';

(m) R8 is selected from the group consisting of hydrogen, $C_1$-$C_4$ alkyl, $C_1$-$C_4$ alkylenyl, oxo, sulfo, and halo;

(n) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, oxo, sulfo, and OR29, and R8 and R9 together optionally combine to form a fused C5-C6 ring with the carbons to which they are attached, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(o) R10, R11 are each independently selected from the group consisting of hydrogen, hydroxy, cyano, nitro, halo, oxo, $C_1$-$C_6$ alkyl, $C_0$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-6}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three independently selected from R28;

(p) R12', R12", R13', R14', R15', R16', R17', R18', R19', R20', R21', R22', R23', R24', and R25' are each independently selected from the group consisting of hydrogen, $C_1$-$C_6$ alkyl and aryl;

(q) R30 is selected from the group consisting of $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(r) R33 is selected from the group consisting of phenyl, thiophene, pyridine, piperidine,

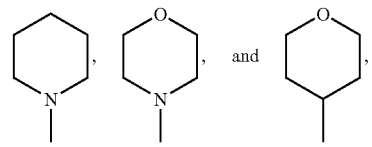

wherein the phenyl, thiophene, pyridine, piperidine,

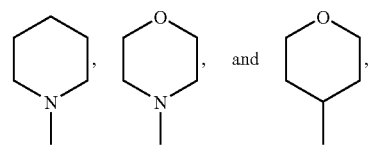

are each optionally substituted with R10 and R11;

wherein "- - - -" are each independently an optional bond to form a double bond at the indicated position.

2. The compound of claim 1, wherein the compound is represented by the following Structural Formula:

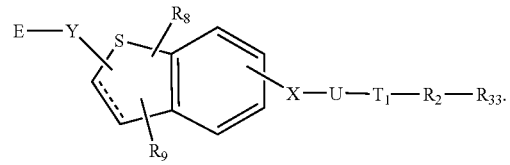

3. The compound of claim 2, wherein the compound is represented by the following Structural Formula:

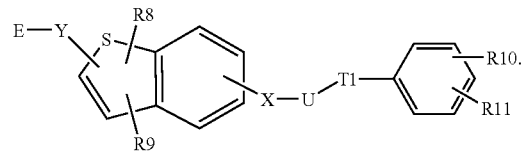

4. The compound of claim 3 wherein the compound is represented by the following Structural Formula:

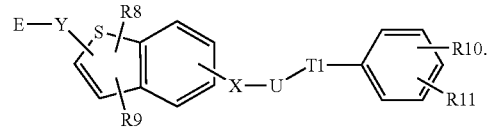

5. The compound of claim 4 wherein:
X is —O—;
E is C(R3)(R4)CO$_2$H or CO$_2$H;
R1, R3, and R4 are each independently selected from the group consisting of hydrogen and $C_1$-$C_2$ alkyl;
R10 and R11 are each independently selected from the group consisting of hydrogen, halo, oxo, $C_1$-$C_6$ alkyl, $C_1$-$C_6$ alkyl-COOR12", $C_1$-$C_6$ alkoxy, $C_1$-$C_6$ haloalkyl, and $C_1$-$C_6$ haloalkyloxy; and U is saturated $C_1$-$C_3$ alkyl optionally substituted with $C_1$-$C_3$ alkyl.

6. A compound selected from the group consisting of:
{6-[5-Methyl-2-(4-trifluoromethyl-phenyl)-oxazol-4-yl-methoxy]-benzo[b]thiophen-3-yl}-acetic acid;
{4-[4-Isopropyl-2-(4-trifluoromethyl-phenyl)-thiazol-5-ylmethoxy]-benzo[b]thiophen-3-yl}-acetic acid;
{4-[5-Methyl-2-(4-trifluoromethyl-phenyl)-oxazol-4-yl-methoxy]-benzo[b]thiophen-3-yl}-acetic acid;
(6-{2-[5-Methyl-2-(4-trifluoromethyl-phenyl)-thiazol-4-yl]-propoxy}-benzo[b]thiophen-3-yl)-acetic acid;
(6-{1-[4-Isopropyl-2-(4-trifluoromethyl-phenyl)-thiazol-5-yl]-ethoxy}-benzo[b]thiophen-3-yl)-acetic acid;
(6-{2-[5-Methyl-2-(4-trifluoromethyl-phenyl)-oxazol-4-yl]-ethoxy}-benzo[b]thiophen-3-yl)-acetic acid;
(6-{2-[5-Methyl-2-(4-trifluoromethyl-phenyl)-oxazol-4-yl]-propoxy}-benzo[b]thiophen-3-yl)-acetic acid;
(6-{2-[4-Isopropyl-2-(4-trifluoromethyl-phenyl)-thiazol-5-yl]-propoxy}-benzo[b]thiophen-3-yl)-acetic acid;
(R)-(6-{2-[4-Isopropyl-2-(4-trifluoromethyl-phenyl)-thiazol-5-yl]-propoxy}-benzo[b]thiophen-3-yl)-acetic acid;
(S)-(6-{2-[4-Isopropyl-2-(4-trifluoromethyl-phenyl)-thiazol-5-yl]-propoxy}-benzo[b]thiophen-3-yl)-acetic acid;
(R)-(4-{2-[5-Methyl-2-(4-trifluoromethyl-phenyl)-thiazol-4-yl]-propoxy}-benzo[b]thiophen-3-yl)-acetic acid;
(S)-(4-{2-[5-Methyl-2-(4-trifluoromethyl-phenyl)-thiazol-4-yl]-propoxy}-benzo[b]thiophen-3-yl)-acetic acid;
(4-{2-[5-Methyl-2-(4-trifluoromethyl-phenyl)-thiazol-4-yl]-ethoxy}-benzo[b]thiophen-3-yl)-acetic acid;
Racemic-(4-{1-[4-Isopropyl-2-(4-trifluoromethyl-phenyl)-thiazol-5-yl]-ethoxy}-benzo[b]thiophen-3-yl)-acetic acid;
{6-[4-Isopropyl-2-(4-trifluoromethyl-phenyl)-thiazol-5-ylmethoxy]-benzo[b]thiophen-3-yl}-acetic acid; and
2-(6-((4-tert-butyl-2-(4-(trifluoromethyl)phenyl)thiazol-5-yl)methylthio)-benzo[b]thiophen-3-yl)acetic acid.

7. A method of treating a mammal in need of treatment for a disease, wherein the disease is treatable by activating a peroxisome proliferator activated receptor, comprising the step of administering to the mammal in need thereof a therapeutically effective amount of the compound of claim 1, wherein the disease is selected from diabetes mellitus, Syndrome X, and atherosclerosis.

8. The method of claim 7, wherein the disease is diabetes mellitus.

9. The method of claim 7, wherein the disease is Syndrome X.

10. A compound, wherein the compound is:
{6-[4-Isopropyl-2-(4-trifluoromethyl-phenyl)-thiazol-5-ylmethoxy]-benzo[b]thiophen-3-yl}-acetic acid; or
2-(6-((4-tert-butyl-2-(4-(trifluoromethyl)phenyl)thiazol-5-yl)methylthio)benzo[b]thiophen-3-yl)acetic acid;
or a stereoisomer, pharmaceutically acceptable salt, or hydrate thereof.

11. A method of treating a human subject in need of treatment for a disease selected from the group consisting of diabetes mellitus, Syndrome X, and atherosclerosis, comprising the step of administering to the subject in need thereof a therapeutically effective amount of the compound of claim 10.

12. A method of treating a mammal in need of treatment for a disease, wherein the disease is treatable by activating a peroxisome proliferator activated receptor, comprising the step of administering to the mammal in need thereof a therapeutically effective amount of the compound of claim 6, disease selected from the group consisting of diabetes mellitus, Syndrome X, and atherosclerosis.

13. A compound represented by the following Structural Formula:

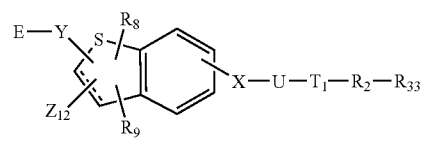

or a stereoisomer, pharmaceutically acceptable salt, or hydrate thereof, wherein:
(s) T1 is a moiety of formula

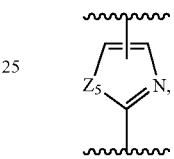

optionally substituted with
one substituent selected from $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, wherein $C_1$-$C_8$ alkyl, $C_1$-$C_8$ alkenyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents independently selected from R1'; or
one substituent selected form $C_1$-$C_6$ haloalkyl, and $C_1$-$C_6$ alkyloxo; and;

(t) R1', R26, R27, R28, R31, Z14', and Z15' are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(u) R2 is selected from the group consisting of $C_0$-$C_8$ alkyl and $C_{1-6}$-heteroalkyl;

(v) X is selected from the group consisting of a bond, O, S, S(O)$_2$ and N;

(w) U is an aliphatic linker wherein one carbon atom of the aliphatic linker may be replaced with O, NH or S, and wherein such aliphatic linker is optionally substituted with R30;

(x) Y is selected from the group consisting of C, O, S, NH and a single bond;

(y) E is C(R3)(R4)A or A and wherein
(i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl-$C_0$-$C_4$ alkyl and $C_1$-$C_6$ alkyl, wherein such alkyl and arylalkyl are each optionally substituted with from one to two groups independently selected from $R7'$; each $R7'$ is independently selected from halo, $C_1$-$C_6$ alkyl, and halo$C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of hydrogen, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(z) Z5 is S or O;

(aa) Z12 is selected from the group consisting of hydrogen and -Z13$C_0$-$C_3$alkylZ14;

(bb) Z13 is selected from the group consisting of a single bond, CO, $CO_2$, CONZ15, and $SO_2$;

(cc) Z14 is selected from the group consisting of aryl and heteroaryl, wherein the aryl and heteroaryl is each optionally substituted with from one to three substituents independently selected from Z14';

(dd) Z15 is selected from the group consisting of hydrogen, aryl, and heteroaryl, wherein the aryl and heteroaryl is each optionally substituted with from one to three substituents independently selected from Z15';

(ee) R8 is selected from the group consisting of hydrogen, $C_1$-$C_4$ alkyl, $C_1$-$C_4$ alkylenyl, oxo, sulfo, and halo;

(ff) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ alkyl, oxo, sulfo, and OR29, and R8 and R9 together optionally combine to form a fused C5-C6 ring with the carbons to which they are attached, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(gg) R10, R11 are each independently selected from the group consisting of hydrogen, hydroxy, cyano, nitro, halo, oxo, $C_1$-$C_6$ alkyl, $C_0$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-6}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three independently selected from R28;

(hh) R12', R12", R13', R14', R15', R16', R17', R18', R19', R20', R21', R22', R23', R24', and R25' are each independently selected from the group consisting of hydrogen, $C_1$-$C_6$ alkyl and aryl;

(ii) R30 is selected from the group consisting of $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-6}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(jj) R33 is selected from the group consisting of phenyl, thiophene, pyridine, piperidine,

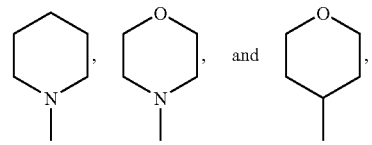

wherein the phenyl, thiophene, pyridine, piperidine,

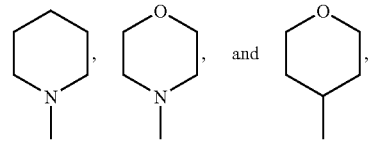

are each optionally substituted with R10 and R11;

wherein "- - - -" are each independently an optional bond to form a double bond at the indicated position.

* * * * *